United States Patent
Higgins et al.

(10) Patent No.: US 10,400,017 B2
(45) Date of Patent: *Sep. 3, 2019

(54) METHODS AND COMPOSITIONS FOR DELIVERING INTERLEUKIN-1 RECEPTOR ANTAGONIST

(71) Applicant: Biomet Biologics, LLC, Warsaw, IN (US)

(72) Inventors: Joel C. Higgins, Claypool, IN (US); Jennifer E. Woodell-May, Warsaw, IN (US); Jacy C. Hoeppner, Warsaw, IN (US)

(73) Assignee: Biomet Biologics, LLC, Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/616,548

(22) Filed: Jun. 7, 2017

(65) Prior Publication Data

US 2017/0334960 A1 Nov. 23, 2017

Related U.S. Application Data

(62) Division of application No. 14/808,828, filed on Jul. 24, 2015, now Pat. No. 9,701,728, which is a division of application No. 12/394,723, filed on Feb. 27, 2009, now Pat. No. 10,106,587.

(60) Provisional application No. 61/031,803, filed on Feb. 27, 2008, provisional application No. 61/116,940, filed on Nov. 21, 2008, provisional application No. 61/155,048, filed on Feb. 24, 2009.

(51) Int. Cl.
| | |
|---|---|
| C07K 14/47 | (2006.01) |
| C07K 1/34 | (2006.01) |
| A61K 38/17 | (2006.01) |
| A61K 45/06 | (2006.01) |
| A61K 9/00 | (2006.01) |
| A61K 47/34 | (2017.01) |

(52) U.S. Cl.
CPC ............ *C07K 14/47* (2013.01); *A61K 9/0019* (2013.01); *A61K 38/1709* (2013.01); *A61K 45/06* (2013.01); *A61K 47/34* (2013.01); *C07K 1/34* (2013.01)

(58) Field of Classification Search
CPC .......... C07K 14/47; C07K 1/34; A61K 45/06; A61K 38/1709; A61K 9/0019; A61K 47/34
See application file for complete search history.

(56) References Cited

U.S. PATENT DOCUMENTS

| | | |
|---|---|---|
| 593,333 A | 11/1897 | Park |
| 1,468,313 A | 9/1923 | Fritz |
| 1,593,814 A | 7/1926 | Robert |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt |
| 3,741,400 A | 6/1973 | Dick |
| 3,779,383 A | 12/1973 | Ayres |
| 3,785,549 A | 1/1974 | Latham |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |

(Continued)

FOREIGN PATENT DOCUMENTS

| | | |
|---|---|---|
| AU | 696278 B2 | 9/1998 |
| AU | 748575 B2 | 6/2002 |

(Continued)

OTHER PUBLICATIONS

"U.S. Appl. No. 12/394,723, Final Office Action dated May 18, 2018", 9 pgs.
"U.S. Appl. No. 12/394,723, Response filed Feb. 14, 2018 to Non Final Office Action dated Nov. 14, 2017", 27 pgs.
"U.S. Appl. No. 12/394,723, Response filed Jun. 18, 2018 to Final Office Action dated May 18, 2018", 7 pgs.
"U.S. Appl. No. 13/837,480, Response filed Mar. 8, 2018 to Non Final Office Action dated Dec. 8, 2017", 13 pgs.
"U.S. Appl. No. 13/839,280, Response filed Mar. 28, 2018 to Non Final Office Action dated Dec. 28, 2017", 13 pgs.
"U.S. Appl. No. 14/830,977, Final Office Action dated Feb. 23, 2018", 10 pgs.

(Continued)

*Primary Examiner* — Taeyoon Kim
(74) *Attorney, Agent, or Firm* — Schwegman Lundberg & Woessner, P.A.

(57) ABSTRACT

Methods and compositions generating and using an interleukin-1 receptor antagonist (IL-1ra)-rich solution. Methods for generating and isolating interleukin-1 receptor antagonist include incubating a liquid volume of white blood cells and platelets with polyacrylamide beads to produce interleukin-1 receptor antagonist. The interleukin-1 receptor antagonist is isolated from the polyacrylamide beads to obtain the solution rich in interleukin-1 receptor antagonist. Methods for treating a site of inflammation in a patient include administering to the site of inflammation the solution rich in interleukin-1 receptor antagonist.

13 Claims, 10 Drawing Sheets

(56) References Cited

U.S. PATENT DOCUMENTS

| | | |
|---|---|---|
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty |
| 4,146,172 A | 3/1979 | Cullis et al. |
| 4,152,270 A | 5/1979 | Cornell |
| 4,154,690 A | 5/1979 | Ballies |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. |
| 4,322,298 A | 3/1982 | Persidsky |
| 4,332,351 A | 6/1982 | Kellogg |
| 4,362,567 A | 12/1982 | Schwarz et al. |
| 4,364,832 A | 12/1982 | Ballies |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer |
| 4,417,981 A | 11/1983 | Nugent |
| 4,424,132 A | 1/1984 | Iriguchi |
| 4,427,650 A | 1/1984 | Stroetmann |
| 4,427,651 A | 1/1984 | Stroetmann |
| 4,442,655 A | 4/1984 | Stroetmann |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin |
| 4,627,879 A | 12/1986 | Rose et al. |
| 4,631,055 A | 12/1986 | Redl et al. |
| 4,632,761 A | 12/1986 | Bowers |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger |
| 4,708,799 A | 11/1987 | Gerlach et al. |
| 4,714,457 A | 12/1987 | Alterbaum |
| 4,722,790 A | 2/1988 | Cawley et al. |
| 4,724,317 A | 2/1988 | Brown |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani |
| 4,900,453 A | 2/1990 | Sedlmayer |
| 4,902,281 A | 2/1990 | Avoy |
| 4,909,251 A | 3/1990 | Seelich |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'donnell, Jr. |
| 5,019,243 A | 5/1991 | Mcewen et al. |
| 5,024,613 A | 6/1991 | Vasconcellos et al. |
| 5,030,215 A | 7/1991 | Morse et al. |
| 5,030,341 A | 7/1991 | Mcewen et al. |
| 5,039,401 A | 8/1991 | Columbus et al. |
| 5,045,048 A | 9/1991 | Kaleskas |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,075,222 A | 12/1991 | Hannum et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling |
| 5,178,602 A | 1/1993 | Wells |
| 5,185,001 A | 2/1993 | Galanakis |
| 5,188,583 A | 2/1993 | Guigan |
| 5,190,057 A | 3/1993 | Sarfarazi |
| 5,190,759 A | 3/1993 | Lindblad et al. |

(56) References Cited

U.S. PATENT DOCUMENTS

| | | |
|---|---|---|
| 5,197,985 A | 3/1993 | Caplan |
| 5,203,825 A | 4/1993 | Haynes |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-radosevich et al. |
| 5,269,927 A | 12/1993 | Fiehler |
| 5,271,852 A | 12/1993 | Luoma, II |
| 5,279,825 A | 1/1994 | Wehling |
| 5,281,342 A | 1/1994 | Biesel et al. |
| 5,290,552 A | 3/1994 | Sierra et al. |
| 5,290,918 A | 3/1994 | Bui-khac |
| 5,298,171 A | 3/1994 | Biesel |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh |
| 5,321,126 A | 6/1994 | Van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,359,032 A | 10/1994 | Dayer et al. |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-fogh et al. |
| 5,484,383 A | 1/1996 | Fitch, Jr. et al. |
| 5,486,359 A | 1/1996 | Caplan et al. |
| 5,494,578 A | 2/1996 | Brown |
| 5,494,592 A | 2/1996 | Latham, Jr. et al. |
| 5,501,371 A | 3/1996 | Schwartz-feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,571,418 A | 11/1996 | Lee et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,599,558 A | 2/1997 | Gordinier et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,792,450 A | 8/1998 | Wilson et al. |
| 5,795,489 A | 8/1998 | Holm |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,842,477 A | 12/1998 | Naughton et al. |
| 5,846,427 A | 12/1998 | Kessler et al. |
| 5,853,600 A | 12/1998 | Mcneal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,895,575 A | 4/1999 | Kraus et al. |
| 5,899,874 A | 5/1999 | Jonsson |
| 5,900,245 A | 5/1999 | Sawhney et al. |
| 5,906,934 A | 5/1999 | Grande et al. |
| 5,916,557 A | 6/1999 | Berlowitz-tarrant et al. |
| 5,916,743 A | 6/1999 | Lake et al. |
| 5,918,622 A | 7/1999 | Perez |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm |
| 5,961,210 A | 10/1999 | Mccardel et al. |
| 5,980,734 A | 11/1999 | Itoh |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |

(56) References Cited

U.S. PATENT DOCUMENTS

| | | |
|---|---|---|
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,096,728 A | 8/2000 | Collins et al. |
| 6,102,843 A | 8/2000 | Kelley et al. |
| 6,117,425 A | 9/2000 | Macphee et al. |
| 6,123,655 A | 9/2000 | Fell |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | Macphee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,287,558 B1 | 9/2001 | Lanza et al. |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,337,072 B1 | 1/2002 | Ford et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | Dicesare et al. |
| 6,409,528 B1 | 6/2002 | Bodnar |
| 6,410,344 B1 | 6/2002 | Chung |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | Dicesare et al. |
| 6,523,698 B1 | 2/2003 | Dennehey et al. |
| 6,544,162 B1 | 4/2003 | Van et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,599,873 B1 | 7/2003 | Sommer et al. |
| 6,623,472 B1 | 9/2003 | Reincke et al. |
| 6,623,959 B2 | 9/2003 | Harris |
| 6,629,919 B2 | 10/2003 | Egozy et al. |
| 6,638,503 B2 | 10/2003 | Chitte |
| 6,641,708 B1 | 11/2003 | Becker et al. |
| 6,645,388 B2 | 11/2003 | Sheikh-ali |
| 6,649,072 B2 | 11/2003 | Brandt et al. |
| 6,676,629 B2 | 1/2004 | Andrew et al. |
| 6,713,246 B1 | 3/2004 | Reinecke et al. |
| 6,716,187 B1 | 4/2004 | Jorgensen |
| 6,719,901 B2 | 4/2004 | Dolecek et al. |
| 6,733,471 B1 | 5/2004 | Ericson et al. |
| 6,758,978 B1 | 7/2004 | Bedell |
| 6,759,188 B2 | 7/2004 | Reinecke et al. |
| 6,764,531 B2 | 7/2004 | Hogan |
| 6,777,231 B1 | 8/2004 | Katz et al. |
| 6,790,371 B2 | 9/2004 | Dolecek |
| 6,803,022 B2 | 10/2004 | Dicesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Jakary et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Jakary et al. |
| 6,955,642 B1 | 10/2005 | Simon |
| 6,979,307 B2 | 12/2005 | Beretta et al. |
| 7,011,644 B1 | 3/2006 | Andrew et al. |
| 7,011,852 B2 | 3/2006 | Sukavaneshvar et al. |
| 7,077,273 B2 | 7/2006 | Ellsworth et al. |
| 7,077,827 B2 | 7/2006 | Greenfield |
| 7,148,209 B2 | 12/2006 | Hoemann et al. |
| 7,155,288 B2 | 12/2006 | Soykan et al. |
| 7,166,283 B2 | 1/2007 | Tsuji et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero |
| 7,302,882 B2 | 12/2007 | Reuter |
| 7,354,515 B2 | 4/2008 | Coull et al. |
| 7,374,678 B2 | 5/2008 | Leach et al. |
| 7,411,006 B2 | 8/2008 | Shanbrom |
| 7,465,293 B2 | 12/2008 | Reinecke et al. |
| 7,470,371 B2 | 12/2008 | Dorian et al. |
| 7,520,849 B1 | 4/2009 | Simon |
| 7,531,355 B2 | 5/2009 | Rodríguez et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,845,499 B2 | 12/2010 | Higgins et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,987,995 B2 | 8/2011 | Dorian et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota |
| 8,093,211 B2 | 1/2012 | Tennenbaum et al. |
| 8,202,539 B2 | 6/2012 | Behnam et al. |
| 8,567,609 B2 | 10/2013 | Landrigan et al. |
| 8,596,470 B2 | 12/2013 | Leach et al. |
| 8,753,690 B2 | 6/2014 | Higgins et al. |
| 8,783,470 B2 | 7/2014 | Hecker et al. |
| 8,801,586 B2 | 8/2014 | Dorian et al. |
| 8,808,551 B2 | 8/2014 | Leach et al. |
| 8,950,586 B2 | 2/2015 | Dorian et al. |
| 8,992,862 B2 | 3/2015 | Leach et al. |
| 9,011,800 B2 | 4/2015 | Leach et al. |
| 9,119,829 B2 | 9/2015 | Higgins et al. |
| 9,308,224 B2 | 4/2016 | Higgins et al. |
| 9,556,243 B2 | 1/2017 | Leach et al. |
| 9,701,728 B2 | 7/2017 | Higgins et al. |
| 9,758,806 B2 | 9/2017 | Woodell-May et al. |
| 9,763,875 B2 | 9/2017 | Higgins et al. |
| 9,878,011 B2 | 1/2018 | Landrigan et al. |
| 9,895,418 B2 | 2/2018 | Landrigan et al. |
| 10,106,587 B2 | 10/2018 | Higgins et al. |
| 10,143,725 B2 | 12/2018 | Toler et al. |
| 10,208,095 B2 | 2/2019 | Leach et al. |
| 2001/0009757 A1 | 7/2001 | Bischof et al. |
| 2001/0016195 A1 | 8/2001 | Tobinick |

(56) References Cited

U.S. PATENT DOCUMENTS

| | | |
|---|---|---|
| 2001/0053764 A1 | 12/2001 | Sims et al. |
| 2002/0009454 A1 | 1/2002 | Boone et al. |
| 2002/0032112 A1 | 3/2002 | Pages |
| 2002/0035820 A1 | 3/2002 | Farris |
| 2002/0076400 A1 | 6/2002 | Katz et al. |
| 2002/0077276 A1 | 6/2002 | Fredeking et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0119179 A1 | 8/2002 | Rezania et al. |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0055511 A1 | 3/2003 | Schryver et al. |
| 2003/0082152 A1 | 5/2003 | Hedrick et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0185803 A1 | 10/2003 | Kadiyala et al. |
| 2003/0191429 A1 | 10/2003 | Andrew et al. |
| 2003/0194397 A1 | 10/2003 | Mishra |
| 2003/0198687 A1 | 10/2003 | Bennett |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | Mcginnis et al. |
| 2004/0156823 A1 | 8/2004 | Reinecke et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0049640 A1 | 3/2005 | Gurtner et al. |
| 2005/0059589 A1 | 3/2005 | Mullarkey |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0100536 A1 | 5/2005 | Mishra |
| 2005/0109716 A1 | 5/2005 | Leach et al. |
| 2005/0130301 A1 | 6/2005 | Mckay et al. |
| 2005/0145187 A1 | 7/2005 | Gray |
| 2005/0152905 A1 | 7/2005 | Omoigui |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0186193 A1 | 8/2005 | Mishra |
| 2005/0196393 A1 | 9/2005 | Shanbrom |
| 2005/0196874 A1 | 9/2005 | Dorian et al. |
| 2005/0197293 A1 | 9/2005 | Mellis et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0271738 A1 | 12/2005 | Simon |
| 2005/0282275 A1 | 12/2005 | Katz et al. |
| 2006/0046960 A1 | 3/2006 | Mckay et al. |
| 2006/0051865 A1 | 3/2006 | Higgins et al. |
| 2006/0057223 A1 | 3/2006 | Dimauro et al. |
| 2006/0057693 A1 | 3/2006 | Simon |
| 2006/0083720 A1 | 4/2006 | Fraser et al. |
| 2006/0121002 A1 | 6/2006 | Rolland et al. |
| 2006/0140923 A1 | 6/2006 | Evangelista |
| 2006/0151384 A1 | 7/2006 | Ellsworth et al. |
| 2006/0171948 A1 | 8/2006 | Weinstein et al. |
| 2006/0175242 A1 | 8/2006 | Dorian et al. |
| 2006/0175244 A1 | 8/2006 | Dorian et al. |
| 2006/0175268 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0263407 A1 | 11/2006 | Mishra |
| 2006/0263408 A1 | 11/2006 | Rezania et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0092494 A1 | 4/2007 | Higgins et al. |
| 2007/0105769 A1 | 5/2007 | Simon |
| 2007/0207161 A1 | 9/2007 | Ralph |
| 2007/0208321 A1 | 9/2007 | Leach et al. |
| 2007/0299472 A1 | 12/2007 | Brighton |
| 2008/0011684 A1 | 1/2008 | Dorian et al. |
| 2008/0019964 A1 | 1/2008 | Olmarker et al. |
| 2008/0044852 A1 | 2/2008 | Kanayinkal et al. |
| 2008/0064626 A1 | 3/2008 | Zanella |
| 2008/0145834 A1 | 6/2008 | Ho et al. |
| 2008/0164204 A1 | 7/2008 | Hatamian et al. |
| 2008/0173593 A1 | 7/2008 | Coull et al. |
| 2008/0193424 A1 | 8/2008 | Mckale et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-may |
| 2008/0269762 A1 | 10/2008 | Simon et al. |
| 2008/0283474 A1 | 11/2008 | Leach et al. |
| 2008/0300181 A1 | 12/2008 | Wang et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | De Wildt et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0289014 A1 | 11/2009 | Hoeppner |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0186676 A1 | 7/2010 | Van Der |
| 2010/0198130 A1 | 8/2010 | Swift et al. |
| 2010/0206798 A1 | 8/2010 | Dorian et al. |
| 2010/0226909 A1 | 9/2010 | Hecker et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0052561 A1 | 3/2011 | Hoeppner |
| 2011/0056893 A1 | 3/2011 | Leach et al. |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0065183 A1 | 3/2011 | Dorian et al. |
| 2011/0077596 A1 | 3/2011 | Higgins et al. |
| 2011/0129441 A1 | 6/2011 | Lentz |
| 2011/0147929 A1 | 6/2011 | Mihir et al. |
| 2011/0168193 A1 | 7/2011 | Leach et al. |
| 2011/0189172 A1 | 8/2011 | Solinger et al. |
| 2011/0192804 A1 | 8/2011 | Landrigan et al. |
| 2011/0251041 A1 | 10/2011 | Chavarria et al. |

(56) References Cited

U.S. PATENT DOCUMENTS

| | | |
|---|---|---|
| 2011/0268708 A1 | 11/2011 | Lin et al. |
| 2011/0300102 A1 | 12/2011 | Chung et al. |
| 2012/0010559 A1 | 1/2012 | Higgins et al. |
| 2012/0015796 A1 | 1/2012 | Leach et al. |
| 2012/0027746 A1 | 2/2012 | Dorian et al. |
| 2012/0093936 A1 | 4/2012 | Lindenberg et al. |
| 2012/0145652 A1 | 6/2012 | Leach et al. |
| 2012/0150086 A1 | 6/2012 | Cohen |
| 2012/0172836 A1 | 7/2012 | Higgins et al. |
| 2012/0228203 A1 | 9/2012 | Hecker et al. |
| 2013/0068676 A1 | 3/2013 | Leach et al. |
| 2013/0102452 A1 | 4/2013 | Leach et al. |
| 2013/0119549 A1 | 5/2013 | Cheng et al. |
| 2013/0178425 A1 | 7/2013 | Higgins et al. |
| 2013/0196425 A1 | 8/2013 | Dorian et al. |
| 2013/0259951 A1 | 10/2013 | O'Connell |
| 2013/0294983 A1 | 11/2013 | Dorian et al. |
| 2014/0051061 A1 | 2/2014 | Landrigan et al. |
| 2014/0054246 A1 | 2/2014 | Landrigan et al. |
| 2014/0091048 A1 | 4/2014 | Leach et al. |
| 2014/0242045 A1 | 8/2014 | Higgins et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |
| 2014/0271870 A1 | 9/2014 | O'Shaughnessey et al. |
| 2014/0274893 A1 | 9/2014 | Woodell-May et al. |
| 2014/0274894 A1 | 9/2014 | Leach et al. |
| 2014/0274895 A1 | 9/2014 | Binder et al. |
| 2014/0275497 A1 | 9/2014 | Leach et al. |
| 2014/0349388 A1 | 11/2014 | Dorian et al. |
| 2014/0356446 A1 | 12/2014 | Leach et al. |
| 2015/0141332 A1 | 5/2015 | Toler |
| 2015/0147300 A1 | 5/2015 | Woodell-May et al. |
| 2016/0000870 A1 | 1/2016 | Higgins et al. |
| 2016/0017010 A1 | 1/2016 | Higgins et al. |
| 2016/0074479 A1 | 3/2016 | Serbousek et al. |
| 2016/0136245 A1 | 5/2016 | Toler et al. |
| 2016/0166645 A1 | 6/2016 | Matuska et al. |
| 2018/0099026 A1 | 4/2018 | Landrigan et al. |

FOREIGN PATENT DOCUMENTS

| | | |
|---|---|---|
| BR | 9103724 A | 3/1993 |
| CA | 1321138 C | 8/1993 |
| CA | 2182862 A1 | 6/1996 |
| CA | 2448415 A1 | 12/2002 |
| CA | 2772084 C | 10/2016 |
| CN | 1074709 A | 7/1993 |
| CN | 1321103 A | 11/2001 |
| CN | 1322146 A | 11/2001 |
| CN | 101056613 A | 10/2007 |
| CN | 102573790 A | 7/2012 |
| CN | 102596173 A | 7/2012 |
| CN | 103702729 A | 4/2014 |
| CN | 105209478 A | 12/2015 |
| CN | 105338990 A | 2/2016 |
| CN | 105339007 A | 2/2016 |
| CN | 105358161 A | 2/2016 |
| CN | 105358162 A | 2/2016 |
| CN | 105492015 A | 4/2016 |
| DE | 56103 C | 10/1960 |
| DE | 1443359 A1 | 11/1968 |
| DE | 4202667 C1 | 5/1993 |
| EP | 090997 A2 | 10/1983 |
| EP | 0102773 A2 | 3/1984 |
| EP | 0109374 A1 | 5/1984 |
| EP | 0142339 A1 | 5/1985 |
| EP | 0244834 A2 | 11/1987 |
| EP | 0253198 A1 | 1/1988 |
| EP | 0295771 A2 | 12/1988 |
| EP | 0417818 A1 | 3/1991 |
| EP | 0534178 A2 | 3/1993 |
| EP | 0592242 A1 | 4/1994 |
| EP | 1005910 A2 | 6/2000 |
| EP | 1006360 A2 | 6/2000 |
| EP | 1289618 A1 | 3/2003 |
| EP | 1427279 A1 | 6/2004 |
| EP | 1467746 A2 | 10/2004 |
| EP | 1509326 A2 | 3/2005 |
| EP | 1652538 A2 | 5/2006 |
| EP | 1670315 A2 | 6/2006 |
| EP | 1716901 A1 | 11/2006 |
| EP | 1406492 B1 | 12/2009 |
| EP | 2186877 A2 | 5/2010 |
| EP | 2259774 A | 12/2010 |
| EP | 2259774 B1 | 12/2012 |
| EP | 2567692 A1 | 3/2013 |
| EP | 2620139 A1 | 7/2013 |
| EP | 2968409 A1 | 1/2016 |
| EP | 2968412 A1 | 1/2016 |
| EP | 2470163 B1 | 9/2016 |
| GB | 854715 A | 11/1960 |
| JP | 60053845 A | 3/1985 |
| JP | 60250014 A | 12/1985 |
| JP | 2036872 A | 2/1990 |
| JP | 02071747 A | 3/1990 |
| JP | 02129224 A | 5/1990 |
| JP | 069684 A | 1/1994 |
| JP | 07101874 A | 4/1995 |
| JP | 1045616 A | 2/1998 |
| JP | 2000189407 A | 7/2000 |
| JP | 2000199760 A | 7/2000 |
| JP | 2001500472 A | 1/2001 |
| JP | 2001515088 A | 9/2001 |
| JP | 2002509529 A | 3/2002 |
| JP | 2002540818 A | 12/2002 |
| JP | 2003525696 A | 9/2003 |
| JP | 2004305439 A | 11/2004 |
| JP | 2005013783 A | 1/2005 |
| JP | 2005098704 A | 4/2005 |
| JP | 2005524451 A | 8/2005 |
| JP | 2006305365 A | 11/2006 |
| JP | 2006527025 A | 11/2006 |
| JP | 2007105186 A | 4/2007 |
| JP | 2007509601 A | 4/2007 |
| JP | 2008104789 A | 5/2008 |
| JP | 2009155234 A | 7/2009 |
| JP | 5551250 B2 | 7/2014 |
| WO | WO-8400905 A1 | 3/1984 |
| WO | WO-8802259 A1 | 4/1988 |
| WO | WO-9010031 A1 | 9/1990 |
| WO | WO-9108285 A1 | 6/1991 |
| WO | WO-9222312 A1 | 12/1992 |
| WO | WO-9305067 A1 | 3/1993 |
| WO | WO-9308904 A1 | 5/1993 |
| WO | WO-9407548 A1 | 4/1994 |
| WO | WO-9617871 A1 | 6/1996 |
| WO | WO-9824477 A1 | 6/1998 |
| WO | WO-1998024477 A1 | 6/1998 |
| WO | WO-9848938 A1 | 11/1998 |
| WO | WO-9905989 A2 | 2/1999 |
| WO | WO-9967277 A1 | 12/1999 |
| WO | WO-0046249 A1 | 8/2000 |
| WO | WO-0061256 A1 | 10/2000 |
| WO | WO-0074713 A1 | 12/2000 |
| WO | WO-0103756 A1 | 1/2001 |
| WO | WO-0183068 A1 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 A1 | 2/2003 |
| WO | WO-03024215 A1 | 3/2003 |
| WO | WO-03053362 A2 | 7/2003 |
| WO | WO-03063799 A2 | 8/2003 |
| WO | WO-03080104 A2 | 10/2003 |
| WO | WO-03088905 A2 | 10/2003 |
| WO | WO-03092894 A2 | 11/2003 |
| WO | WO-03099412 A1 | 12/2003 |
| WO | WO-2004009207 A1 | 1/2004 |
| WO | WO-2004065564 A2 | 8/2004 |
| WO | WO-2004104553 A2 | 12/2004 |
| WO | WO-2005034843 A2 | 4/2005 |
| WO | WO-2006041406 A1 | 4/2006 |
| WO | WO-2006043972 A1 | 4/2006 |

(56) References Cited

FOREIGN PATENT DOCUMENTS

| WO | WO-2007121538 A1 | 11/2007 |
|---|---|---|
| WO | WO-2007127834 A2 | 11/2007 |
| WO | WO-2007128973 A2 | 11/2007 |
| WO | WO-2007142908 A1 | 12/2007 |
| WO | WO-2008021237 A1 | 2/2008 |
| WO | WO-2008100442 A1 | 8/2008 |
| WO | WO-2008127639 A1 | 10/2008 |
| WO | WO-2008157733 A2 | 12/2008 |
| WO | WO-2009021257 A1 | 2/2009 |
| WO | WO-2009108890 A1 | 9/2009 |
| WO | WO-2009111338 A1 | 9/2009 |
| WO | WO-2010115190 A1 | 10/2010 |
| WO | WO-2010149164 A2 | 12/2010 |
| WO | WO-2011008836 A1 | 1/2011 |
| WO | WO-2011031524 A2 | 3/2011 |
| WO | WO-2011031524 A3 | 3/2011 |
| WO | WO-2011031525 A1 | 3/2011 |
| WO | WO-2011031553 A2 | 3/2011 |
| WO | WO-2011031553 A3 | 3/2011 |
| WO | WO-2012030593 A2 | 3/2012 |
| WO | WO-2012030593 A3 | 3/2012 |
| WO | WO-2014144505 A2 | 9/2014 |
| WO | WO-2014144505 A3 | 9/2014 |
| WO | WO-2014149266 A2 | 9/2014 |
| WO | WO-2014149266 A3 | 9/2014 |
| WO | WO-2014149270 A1 | 9/2014 |
| WO | WO-2014149300 A1 | 9/2014 |
| WO | WO-2014149301 A1 | 9/2014 |
| WO | WO-2014149979 A1 | 9/2014 |
| WO | WO-2014150375 A2 | 9/2014 |
| WO | WO-2014150375 A3 | 9/2014 |
| WO | WO-2015099684 A1 | 7/2015 |

OTHER PUBLICATIONS

"U.S. Appl. No. 14/830,977, Response filed May 23, 2018 to Final Office Action dated Feb. 23, 2018", 11 pgs.
"U.S. Appl. No. 14/973,913, Response filed Apr. 16, 2018 to Non Final Office Action dated Jan. 16, 2018", 12 pgs.
"U.S. Appl. No. 15/836,249, Non Final Office Action dated Apr. 6, 2018", 10 pgs.
"U.S. Appl. No. 15/836,249, Preliminary Amendment filed Mar. 9, 2018", 9 pgs.
"Australian Application Serial No. 2014237269, Response filed May 21, 2018 to First Examination Report dated Dec. 11, 2017", 25 pgs.
"Australian Application Serial No. 2014237679, Response filed Apr. 23, 2018 to First Examination Report dated Dec. 11, 2017".
"Australian Application Serial No. 2014237679, Subsequent Examiners Report dated May 29, 2018", 4 pgs.
"Australian Application Serial No. 2014238304, First Examination Report dated Jan. 29, 2018", 4 pgs.
"Australian Application Serial No. 2014238304, Response filed May 15, 2018 to First Examination Report dated Jan. 29, 2018", 50 pgs.
"Australian Application Serial No. 2014238363, First Examination Report dated Feb. 8, 2018", 3 pgs.
"Australian Application Serial No. 2014238363, Response filed May 14, 2018 to First Examination Report dated Feb. 8, 2018", 14 pgs.
"Australian Application Serial No. 2014238367, First Examination Report dated Feb. 16, 2018", 3 pgs.
"Australian Application Serial No. 2014238367, Response filed May 15, 2018 to First Examination Report dated Feb. 16, 2018", 23 pgs.
"Chinese Application Serial No. 201480027178.3, Response filed Feb. 26, 2018 to Office Action dated Oct. 10, 2017", (W/ English Claims), 10 pgs.
"Chinese Application Serial No. 201480027541.1, Office Action dated Mar. 14, 2018", (W/ English Translation), 14 pgs.
"Chinese Application Serial No. 201480027655.6, Office Action dated Feb. 23, 2018", (W/ English translation), 15 pgs.
"European Application Serial No. 10754613.7, Response filed Mar. 29, 2018 to Communication Pursuant to Article 94(3) EPC dated Nov. 28, 2017", 15 pgs.
"European Application Serial No. 14714491.9, Communication Pursuant to Article 94(3) EPC dated Feb. 8, 2018", 6 pgs.
"European Application Serial No. 14724817.3, Communication Pursuant to Article 94(3) EPC dated Apr. 5, 2018", 4 pgs.
"European Application Serial No. 18160602.1, Extended European Search Report dated Apr. 30, 2018", 9 pgs.
Botti, C, et al., "Autologous bone marrow cell therapy for peripheral arterial disease", Stem Cells and Cloning: Advances and Applications, No. 5, (2012), 5-14.
Kubis, N, et al., "Vasculogenesis and Angiogenesis: Molecular and Cellular Controls Part 1: Growth Factors", vol. 9, No. 3, (2003), 227-237.
Milkiewicz, M, et al., "Regulators of angiogenesis and strategies for their therapeutic manipulation", The International Journal of Biochemistry & Cell Biology, vol. 38, No. 3, (2006), 333-357.
Morishita, R, et al., "Safety evaluation of clinical gene therapy using hepatocyte growth factor to treat peripheral arterial disease", Hypertension, vol. 44, No. 2, (2004), 203-209.
Richard, J Powell, et al., "Safety and efficacy of patient specific intramuscular injection of HGF plasmid gene therapy on limb perfusion and wound healing in patients with ischemic lower extremity ulceration: Results of the HGF-0205 trial", Journal of Vascular Surgery, vol. 52, No. 6, (2010), 1525-1530.
"U.S. Appl. No. 12/394,723, Corrected Notice of Allowability dated Sep. 26, 2018", 5 pgs.
"U.S. Appl. No. 12/394,723, PTO Response to Rule 312 Communication dated Sep. 4, 2018", 2 pgs.
"U.S. Appl. No. 13/839,280, Notice of Allowance dated Oct. 2, 2018", 10 pgs.
"U.S. Appl. No. 13/839,280, Response filed Aug. 27, 2018 to Final Office Action dated Jul. 13, 2018", 9 pgs.
"U.S. Appl. No. 14/803,414, Non Final Office Action dated Oct. 4, 2018", 17 pgs.
"Australian Application Serial No. 2014237679, Subsequent Examiners Report dated Sep. 18, 2018", 7 pgs.
"Australian Application Serial No. 2014238304, Response filed Sep. 2, 2018 to Subsequent Examiners Report dated Jun. 9, 2018", 41 pgs.
"Canadian Application Serial No. 2,906,310, Examiner's Rule 30(2) Requisition dated Aug. 30, 2018", 6 pgs.
"Canadian Application Serial No. 2,916,080, Office Action dated Sep. 6, 2018", 4 pgs.
"Chinese Application Serial No. 201480027178.3, Response filed Sep. 29, 2018 to Office Action dated Jun. 15, 2018", w/English claims, 9 pgs.
"Chinese Application Serial No. 201480027408.6, Office Action dated Jul. 24, 2018", W/English Translation, 15 pgs.
"European Application Serial No. 14724817.3, Response filed Sep. 7, 2018 to Communication Pursuant to Article 94(3) EPC dated Apr. 5, 2018", 31 pgs.
"U.S. Appl. No. 12/394,723, Corrected Notice of Allowability dated Jul. 30, 2018", 5 pgs.
"U.S. Appl. No. 12/394,723, Notice of Allowance dated Jul. 17, 2018", 10 pgs.
"U.S. Appl. No. 13/837,480, Notice of Allowance dated Jun. 28, 2018", 7 pgs.
"U.S. Appl. No. 13/839,280, Final Office Action dated Jul. 13, 2018", 12 pgs.
"U.S. Appl. No. 14/973,913, Final Office Action dated Aug. 9, 2018", 11 pgs.
"U.S. Appl. No. 15/836,249, Response filed Jul. 2, 2018 to Non Final Office Action dated Apr. 6, 2018", 11 pgs.
"Australian Application Serial No. 2014237269, Response filed Jul. 28, 2018 to Subsequent Examiners Report dated Jun. 29, 2018", 15 pgs.
"Australian Application Serial No. 2014237269, Subsequent Examiners Report dated Jun. 29, 2018", 10 pgs.

(56) References Cited

OTHER PUBLICATIONS

"Australian Application Serial No. 2014237679, Response filed Jul. 19, 2018 to Subsequent Examiners Report dated May 29, 2018", 54 pgs.
"Australian Application Serial No. 2014238304, Subsequent Examiners Report dated Jun. 9, 2018", 3 pgs.
"Chinese Application Serial No. 201480027178.3, Office Action dated Jun. 15, 2018", w/ English translation, 9 pgs.
"Chinese Application Serial No. 201480027541.1, Response filed Jul. 27, 2018 to Office Action dated Mar. 14, 2018", W/English Claims, 16 pgs.
"Chinese Application Serial No. 201480028053.2, Office Action dated Jul. 3, 2018", W/English Translation, 6 pgs.
"European Application Serial No. 10754613.7, Communication Pursuant to Article 94(3) EPC dated Jun. 26, 2018", 3 pgs.
"U.S. Appl. No. 12/394,723, Final Office Action dated May 15, 2017", 14 pgs.
"U.S. Appl. No. 13/837,005, Notice of Allowance dated May 18, 2017", 10 pgs.
"U.S. Appl. No. 13/837,480, Final Office Action dated May 4, 2017", 12 pgs.
"U.S. Appl. No. 13/837,480, Response filed Aug. 7, 2017 to Final Office Action dated May 4, 2017", 12 pgs.
"U.S. Appl. No. 13/837,480, Response filed Dec. 12, 2016 to Non Final Office Action dated Sep. 13, 2016", 13 pgs.
"U.S. Appl. No. 13/839,280, Response filed Apr. 24, 2017 to Final Office Action dated Jan. 23, 2017", 12 pgs.
"U.S. Appl. No. 13/840,562, Non Final Office Action dated Mar. 7, 2017", 18 pgs.
"U.S. Appl. No. 13/841,083, Notice of Allowance dated Sep. 7, 2017", 8 pgs.
"U.S. Appl. No. 13/841,083, Response filed May 24, 2017 to Non Final Office Action dated Feb. 24, 2017", 18 pgs.
"U.S. Appl. No. 13/841,083, Supplemental Amendment filed Aug. 29, 2017 to Non Final Office Action dated Feb. 24, 2017", 9 pgs.
"U.S. Appl. No. 13/841,103, Examiner Interview Summary dated Jun. 8, 2017", 1 pg.
"U.S. Appl. No. 13/841,103, Non Final Office Action dated Jun. 8, 2017", 13 pgs.
"U.S. Appl. No. 13/841,103, Response filed Mar. 13, 2017 to Final Office Action dated Dec. 14, 2016", 14 pgs.
"U.S. Appl. No. 13/841,103, Response filed Sep. 8, 2017 to Non Final Office Action dated Jun. 8, 2017", 12 pgs.
"U.S. Appl. No. 13/841,103, Supplemental Preliminary Amendment filed Sep. 26, 2017", 7 pgs.
"U.S. Appl. No. 14/803,414, Non Final Office Action dated Apr. 19, 2017", 35 pgs.
"U.S. Appl. No. 14/803,414, Response filed Jul. 10, 2017 to Non Final Office Action dated Apr. 19, 2017", 15 pgs.
"U.S. Appl. No. 14/808,828, PTO Response to Rule 312 Communication dated Jun. 8, 2017", 2 pgs.
"U.S. Appl. No. 14/830,977, Non Final Office Action dated Aug. 7, 2017", 12 pgs.
"Application Serial No. 14714491.9, Non Final Office Action dated Mar. 6, 2017", 9 pgs.
"Chinese Application Serial No. 201480027157.1, Voluntary Amendment filed Jun. 6, 2016", w/English Claims, 63 pgs.
"Chinese Application Serial No. 201480027655.6, Office Action dated May 15, 2017", (W/ English Translation), 11 pgs.
"European Application No. 14707909.9, Summons to Attend Oral Proceedings mailed Aug. 10, 2017", 7 pgs.
"European Application Serial No. 10754613.7, Response filed Aug. 16, 2017 to Non Final Office Action dated Feb. 7, 2017", 20 pgs.
"European Application Serial No. 14707069.2, Response Filed Mar. 27, 2017 to Communication Pursuant to Article 94(3) EPC dated Nov. 15, 2016", 16 pgs.
"European Application Serial No. 14707909.9, Response filed Apr. 26, 2017 to Communication Pursuant to Article 94(3) EPC dated Dec. 16, 2016", 25 pgs.
"European Application Serial No. 14709014.6, Summons to Attend Oral Proceedings mailed Jun. 7, 2017", 8 pgs.
"European Application Serial No. 14709803.2, Communication Pursuant to Article 94(3) EPC dated Jul. 8, 2016", 7 pgs.
"European Application Serial No. 14709803.2, Response filed Nov. 15, 2016 to Communication Pursuant to Article 94(3) EPC dated Jul. 8, 2016", 18 pgs.
"European Application Serial No. 14714491.9, Communication Pursuant to Article 94(3) EPC dated Feb. 28, 2017", 9 pgs.
"European Application Serial No. 14724817.3, Office Action dated Jun. 29, 2017", 5 pgs.
"European Application Serial No. 15184504.7, Communication Pursuant to Article 94(3) EPC dated Jul. 28, 2017", 13 pgs.
"European Application Serial No. 15184504.7, Response filed Jun. 12, 2017 to Communication Pursuant to Article 94(3) EPC dated Feb. 13, 2017", 10 pgs.
"Mexican Application Serial No. Mxa2013002488, Office Action dated Nov. 5, 2015", W/ English Translation, 7 pgs.
Abegao, K., et al., "Effects of heterologous platelet-rich plasma gel on standardized dermal wound healing in rabbits", Acta Cirurgica Brasileira—vol. 30(3), (2015), pp. 208-215.
Abramson, S. B., et al., "Blocking the effects o IL-1 in rheumatoid arthritis protects bone and cartilage", Rheumatology; 41, (2002), 972-980 pgs.
Greppi, N., et al., "Treatment of recalcitrant ulcers with allogeneic platelet gel from pooled platelets in aged hypomobile patients", Biologicals. Academic Press Ltd. vol. 39. No. 2, (Jan. 6, 2011), 73-80 pgs.
Ma, Chaoyong, "Animal Models of Disease: These systems are becoming increasingly important secondary screes of in vitro hits.", Modern Drug Discovery, (Jun. 2004), pp. 30-36.
Matras, Helene, et al., "Zur nahtlosen interfaszikularen Nerventransplantation im Tierexperiment", Wein Med Woschtr 122:37— Not in English, (1972), 517-523.
Nakajima, et al., "Bioactivity of freeze-dried platelet-rich plasma in an adsorbed form on a biodegradable polymer material.", Platelets, (2012), 594-603.
Pettit, et al., "The development of site-specific drug-delivery systems for protein and peptide biopharmaceuticals", Trends in Biotechnology, (1998), 343-349.
Stankiewicz, W., et al., "Low energy electromagnetic fields and immunity", Int. Rev. Allergol. Clin. Immunol, vol. 15, No. 1-2, (2009), pp. 36-41.
Xie, X., et al., "Biology of platelet-rich plasma and its clinical application in cartilage repair", Arthritis Research & Therapy, 16:204, (2014), 15 pgs.
"U.S. Appl. No. 12/394,723, Non Final Office Action dated Nov. 14, 2017", 18 pgs.
"U.S. Appl. No. 12/394,723, Response filed Oct. 16, 2017 to Final Office Action dated May 15, 2017", 18 pgs.
"U.S. Appl. No. 13/837,480, Non Final Office Action dated Dec. 8, 2017", 9 pgs.
"U.S. Appl. No. 13/839,280, Non Final Office Action dated Dec. 28, 2017", 13 pgs.
"U.S. Appl. No. 13/841,103, Notice of Allowance dated Oct. 11, 2017", 8 pgs.
"U.S. Appl. No. 14/803,414, Final Office Action dated Oct. 18, 2017", 26 pgs.
"U.S. Appl. No. 14/803,414, Response field Dec. 18, 2017 to Final Office Action dated Oct. 18, 2017", 13 pgs.
"U.S. Appl. No. 14/830,977, Response filed Nov. 6, 2017 to Non Final Office Action dated Aug. 7, 2017", 13 pgs.
"U.S. Appl. No. 14/973,913, Non Final Office Action dated Jan. 16, 2018", 7 pgs.
"U.S. Appl. No. 14/973,913, Response filed Dec. 20, 2017 to Restriction Requirement dated Oct. 20, 2017", 8 pgs.
"U.S. Appl. No. 14/973,913, Restriction Requirement dated Oct. 20, 2017", 7 pgs.
"Australian Application Serial No. 2014229070, First Examination Report dated Nov. 24, 2017", 3 pgs.
"Australian Application Serial No. 2014229070, Response filed Jan. 15, 2018 to First Examination Report dated Nov. 24, 2017", 25 pgs.

(56) References Cited

OTHER PUBLICATIONS

"Australian Application Serial No. 2014237269, First Examination Report dated Dec. 11, 2017", 6 pgs.
"Australian Application Serial No. 2014237679, First Examination Report dated Dec. 11, 2017", 4 pgs.
"Chinese Application Serial No. 201480027178.3, Office Action dated Oct. 10, 2017", W/ English Translation, 14 pgs.
"Chinese Application Serial No. 201480027655.6, Response filed Oct. 9, 2017 to Office Action dated May 15, 2017", W/ English Translation of Claims, 9 pgs.
"European Application Serial No. 10754613.7, Communication Pursuant to Article 94(3) EPC dated Nov. 28, 2017", 3 pgs.
"European Application Serial No. 14707909.9, Summons to Attend Oral Proceedings mailed Oct. 18, 2017", 2 pgs.
"European Application Serial No. 14709014.6, Summons to Attend Oral Proceedings mailed Oct. 18, 2017", 2 pgs.
"European Application Serial No. 14714491.9, Response filed Oct. 16, 2017 to Non Final Office Action dated Feb. 28, 2017", 18 pgs.
"European Application Serial No. 14724817.3, Response filed Nov. 9, 2017 to Office Action dated Jun. 29, 2017", 19 pgs.
"European Application Serial No. 14729994.5, Communication Pursuant to Article 94(3) EPC dated Oct. 10, 2017", 8 pgs.
Bendinelli, Paola, et al., "Molecular Basis of Anti-Inflammatory Action of Platelet-Rich Plasma on Human Chondrocytes: Mechanisms of NF-kB Inhibition Via HGF", Journal of Cellular Physiology 225, (2010), 757-766.
Le Meur, Yannick, et al., "Whole blood production of monocytic cytokines (IL-1β, IL-6, TNF-a, sIL-6R, IL-1Ra) in haemodialysed patients", Nephrology Dialysis Transplantation; 14, (1999), pp. 2420-2426.
Ulich, Thomas R., et al., "Endotoxin-induced Cytokine Gene Expression In Vivo: IV. Expression of Interleukin-1 a/β and Interleukin-1 Receptor Antagonist mRNA During Endotoxemia and During Endotoxin-initiated Local Acute Inflammation", American Journal of Pathology, vol. 141, No. 1, (Jul. 1992), pp. 61-68.
"A phase I safety study of combination treatment with pegylated soluble tumor necrosis factor receptor type I (PET STNF-RI) and anakinra (interleukin-1 receptor antagonist, IL-1RA) in patients with rheumatoid arthritis", Prous integrity, (Jun. 12, 2002), 1-1.
"U.S. Appl. No. 12/101,586, Final Office Action dated Feb. 3, 2011", 11 pgs.
"U.S. Appl. No. 12/101,586, Non Final Office Action dated Sep. 20, 2010", 12 pgs.
"U.S. Appl. No. 12/101,586, Notice of Allowance dated Mar. 24, 2011", 5 pgs.
"U.S. Appl. No. 12/101,594, Final Office Action dated Mar. 18, 2010", 8 pgs.
"U.S. Appl. No. 12/101,594, Non Final Office Action dated Oct. 16, 2009", 8 pgs.
"U.S. Appl. No. 12/101,594, Notice of Allowance dated May 27, 2010", 7 pgs.
"U.S. Appl. No. 12/394,723, Advisory Action dated Dec. 19, 2014", 3 pgs.
"U.S. Appl. No. 12/394,723, Appeal Brief filed Jun. 15, 2015", 42 pgs.
"U.S. Appl. No. 12/394,723, Decision on Pre-Appeal Brief dated Feb. 13, 2015", 2 pgs.
"U.S. Appl. No. 12/394,723, Examiner's Answer to Appeal Brief dated Sep. 9, 2015", 11 pgs.
"U.S. Appl. No. 12/394,723, Final Office Action dated Apr. 19, 2016", 13 pgs.
"U.S. Appl. No. 12/394,723, Final Office Action dated Jun. 26, 2012", 11 pgs.
"U.S. Appl. No. 12/394,723, Final Office Action dated Sep. 8, 2014", 8 pgs.
"U.S. Appl. No. 12/394,723, Non Final Office Action dated Feb. 7, 2014", 8 pgs.
"U.S. Appl. No. 12/394,723, Non Final Office Action dated Oct. 5, 2016", 16 pgs.
"U.S. Appl. No. 12/394,723, Non Final Office Action dated Oct. 31, 2011", 11 pgs.
"U.S. Appl. No. 12/394,723, Non Final Office Action dated Dec. 24, 2015", 9 Pgs.
"U.S. Appl. No. 12/394,723, Response filed Jan. 8, 2015 to Pre-Appeal Brief Request dated Dec. 19, 2014", 4 pgs.
"U.S. Appl. No. 12/394,723, Response filed Mar. 6, 2017 to Non Final Office Action dated Oct. 5, 2016", 25 pgs.
"U.S. Appl. No. 12/394,723, Response filed Mar. 24, 2016 to Non Final Office Action dated Dec. 24, 2015", 18 pgs.
"U.S. Appl. No. 12/394,723, Response filed Apr. 30, 2012 to Non Final Office Action dated Oct. 31, 2011", 16 pgs.
"U.S. Appl. No. 12/394,723, Response filed Jul. 23, 2014 to Non Final Office Action dated Feb. 7, 2014", 19 pgs.
"U.S. Appl. No. 12/394,723, Response filed Aug. 19, 2016 to Final Office Action dated Apr. 19, 2016", 23 pgs.
"U.S. Appl. No. 12/394,723, Response filed Aug. 22, 2011 to Restriction Requirement dated Jul. 20, 2011", 2 pgs.
"U.S. Appl. No. 12/394,723, Response filed Nov. 9, 2015 to Final Office Action dated Sep. 8, 2014", 19 pgs.
"U.S. Appl. No. 12/394,723, Response filed Dec. 10, 2014 to Final Office Action dated Sep. 8, 2014", 18 pgs.
"U.S. Appl. No. 12/394,723, Response filed Dec. 19, 2012 to Final Office Action dated Jun. 26, 2012", 16 pgs.
"U.S. Appl. No. 12/394,723, Restriction Requirement dated Jul. 20, 2011", 7 pgs.
"U.S. Appl. No. 12/549,015, Examiner Interview Summary dated Dec. 3, 2012", 3 pgs.
"U.S. Appl. No. 12/549,015, Final Office Action dated Aug. 16, 2012", 8 pgs.
"U.S. Appl. No. 12/549,015, Non Final Office Action dated Mar. 9, 2012", 8 pgs.
"U.S. Appl. No. 12/549,015, Notice of Allowance dated Feb. 3, 2014", 9 pgs.
"U.S. Appl. No. 12/549,015, Response filed Feb. 9, 2012 to Restriction Requirement dated Jan. 9, 2012", 2 pgs.
"U.S. Appl. No. 12/549,015, Response filed Jul. 6, 2012 to Non Final Office Action dated Mar. 9, 2012", 12 pgs.
"U.S. Appl. No. 12/549,015, Response filed Dec. 17, 2012 to Final Office Action dated Aug. 16, 2012", 17 pgs.
"U.S. Appl. No. 12/549,015, Restriction Requirement dated Jan. 9, 2012", 5 pgs.
"U.S. Appl. No. 12/549,116, Decision on Pre-Appeal Brief dated Feb. 5, 2015", 2 pgs.
"U.S. Appl. No. 12/549,116, Examiner Interview Summary dated Dec. 5, 2012", 3 pgs.
"U.S. Appl. No. 12/549,116, Final Office Action dated Jan. 4, 2016", 15 pgs.
"U.S. Appl. No. 12/549,116, Final Office Action dated Aug. 8, 2012", 20 pgs.
"U.S. Appl. No. 12/549,116, Final Office Action dated Oct. 8, 2014", 12 pgs.
"U.S. Appl. No. 12/549,116, Non Final Office Action dated Feb. 24, 2012", 16 pgs.
"U.S. Appl. No. 12/549,116, Non Final Office Action dated Jun. 4, 2015", 12 pgs.
"U.S. Appl. No. 12/549,116, Non Final Office Action dated Jun. 5, 2014", 15 pgs.
"U.S. Appl. No. 12/549,116, Non Final Office Action dated Oct. 6, 2016", 15 pgs.
"U.S. Appl. No. 12/549,116, Pre-Appeal Brief Request filed Jan. 8, 2015", 5 pgs.
"U.S. Appl. No. 12/549,116, Response filed Jan. 8, 2013 to Final Office Action dated Aug. 8, 2012", 14 pgs.
"U.S. Appl. No. 12/549,116, Response filed Jan. 13, 2012 to Restriction Requirement dated Dec. 13, 2011", 3 pgs.
"U.S. Appl. No. 12/549,116, Response filed Mar. 3, 2016 to Final Office Action dated Jan. 4, 2016", 11 pgs.
"U.S. Appl. No. 12/549,116, Response filed Jun. 25, 2012 to Non Final Office Action dated Feb. 24, 2012", 14 pgs.
"U.S. Appl. No. 12/549,116, Response filed Sep. 4, 2015 to Non Final Office Action dated Jun. 4, 2015", 9 pgs.

(56) References Cited

OTHER PUBLICATIONS

"U.S. Appl. No. 12/549,116, Response filed Sep. 5, 2014 to Non Final Office Action dated Jun. 5, 2014", 11 pgs.
"U.S. Appl. No. 12/549,116, Restriction Requirement dated Dec. 13, 2011", 6 pgs.
"U.S. Appl. No. 12/897,401, Non Final Office Action dated Nov. 16, 2010", 9 pgs.
"U.S. Appl. No. 12/897,401, Notice of Allowance dated Oct. 18, 2011", 6 pgs.
"U.S. Appl. No. 13/392,266, Advisory Action dated Jul. 31, 2014", 3 pgs.
"U.S. Appl. No. 13/392,266, Examiner Interview Summary dated Jul. 3, 2014", 3 pgs.
"U.S. Appl. No. 13/392,266, Examiner Interview Summary dated Nov. 15, 2013", 3 pgs.
"U.S. Appl. No. 13/392,266, Final Office Action dated May 8, 2014", 10 pgs.
"U.S. Appl. No. 13/392,266, Final Office Action dated Jul. 30, 2015", 12 pgs.
"U.S. Appl. No. 13/392,266, Final Office Action dated Sep. 3, 2013", 13 pgs.
"U.S. Appl. No. 13/392,266, Non Final Office Action dated Feb. 13, 2013", 12 pgs.
"U.S. Appl. No. 13/392,266, Non Final Office Action dated Feb. 26, 2015", 9 pgs.
"U.S. Appl. No. 13/392,266, Non Final Office Action dated Oct. 4, 2016", 21 pgs.
"U.S. Appl. No. 13/392,266, Non Final Office Action dated Dec. 31, 2013", 8 pgs.
"U.S. Appl. No. 13/392,266, Notice of Allowance dated Mar. 6, 2017", 8 pgs.
"U.S. Appl. No. 13/392,266, Preliminary Amendment filed Feb. 24, 2012", 3 pgs.
"U.S. Appl. No. 13/392,266, Preliminary Amendment filed Dec. 12, 2012", 7 pgs.
"U.S. Appl. No. 13/392,266, Response filed Jan. 4, 2017 to Non Final Office Action dated Oct. 4, 2016", 22 pgs.
"U.S. Appl. No. 13/392,266, Response filed Jan. 22, 2016 to Final Office Action dated Jul. 30, 2015", 24 pgs.
"U.S. Appl. No. 13/392,266, Response filed Apr. 18, 2014 to Non Final Office Action dated Dec. 31, 2013", 13 pgs.
"U.S. Appl. No. 13/392,266, Response filed Jul. 2, 2013 to Non Final Office Action dated Feb. 13, 2013", 15 pgs.
"U.S. Appl. No. 13/392,266, Response filed Jul. 8, 2015 to Non-Final Office Action dated Feb. 26, 2015", 13 pgs.
"U.S. Appl. No. 13/392,266, Response filed Jul. 11, 2014 to Final Office Action dated May 8, 2014", 14 pgs.
"U.S. Appl. No. 13/392,266, Response filed Dec. 3, 2013 to Final Office Action dated Sep. 3, 2013", 15 pgs.
"U.S. Appl. No. 13/392,266, Response filed Dec. 13, 2012 to Restriction Requirement dated Nov. 13, 2012", 5 pgs.
"U.S. Appl. No. 13/392,266, Restriction Requirement dated Nov. 13, 2012", 8 pgs.
"U.S. Appl. No. 13/782,421, Final Office Action dated Jan. 15, 2015", 30 pgs.
"U.S. Appl. No. 13/782,421, Non Final Office Action dated Jul. 3, 2014", 26 pgs.
"U.S. Appl. No. 13/782,421, Non Final Office Action dated Sep. 30, 2013", 30 pgs.
"U.S. Appl. No. 13/782,421, Notice of Allowance dated Apr. 27, 2015", 8 pgs.
"U.S. Appl. No. 13/782,421, Preliminary Amendment filed Mar. 1, 2013", 8 pgs.
"U.S. Appl. No. 13/782,421, Response filed Feb. 26, 2014 to Non Final Office Action dated Sep. 30, 2013", 21 pgs.
"U.S. Appl. No. 13/782,421, Response filed Apr. 15, 2015 to Final Office Action dated Jan. 15, 2015", 6 pgs.
"U.S. Appl. No. 13/782,421, Response filed Jul. 3, 2013 to Restriction Requirement dated Jun. 4, 2013", 2 pgs.
"U.S. Appl. No. 13/782,421, Response filed Oct. 3, 2014 to Non Final Office Action dated Jul. 3, 2014", 15 pgs.
"U.S. Appl. No. 13/782,421, Restriction Requirement dated Jun. 4, 2013", 6 pgs.
"U.S. Appl. No. 13/837,005, Advisory Action dated Dec. 2, 2016", 3 pgs.
"U.S. Appl. No. 13/837,005, Final Office Action dated Aug. 23, 2016", 9 pgs.
"U.S. Appl. No. 13/837,005, Final Office Action dated Dec. 5, 2014", 9 pgs.
"U.S. Appl. No. 13/837,005, Non Final Office Action dated Feb. 17, 2016", 13 pgs.
"U.S. Appl. No. 13/837,005, Non Final Office Action dated May 13, 2014", 10 pgs.
"U.S. Appl. No. 13/837,005, Non Final Office Action dated Jun. 9, 2015", 13 pgs.
"U.S. Appl. No. 13/837,005, Response filed Jan. 3, 2014 to Restriction Requirement dated Dec. 3, 2013", 4 pgs.
"U.S. Appl. No. 13/837,005, Response filed Mar. 5, 2015 to Final Office Action dated Dec. 5, 2014", 11 pgs.
"U.S. Appl. No. 13/837,005, Response filed May 17, 2016 to Non Final Office Action dated Feb. 17, 2016", 13 pgs.
"U.S. Appl. No. 13/837,005, Response filed Aug. 13, 2014 to Non Final Office Action dated May 13, 2014", 13 pgs.
"U.S. Appl. No. 13/837,005, Response filed Oct. 24, 2016 to Final Office Action dated Aug. 23, 2016", 9 pgs.
"U.S. Appl. No. 13/837,005, Response filed Nov. 9, 2015 to Non Final Office Action dated Jun. 9, 2015", 11 pgs.
"U.S. Appl. No. 13/837,005, Response filed Dec. 22, 2016 to Advisory Action dated Dec. 2, 2016", 10 pgs.
"U.S. Appl. No. 13/837,005, Restriction Requirement dated Dec. 3, 2013", 9 pgs.
"U.S. Appl. No. 13/837,480, Final Office Action dated May 23, 2016", 11 pgs.
"U.S. Appl. No. 13/837,480, Non Final Office Action dated Aug. 11, 2015", 10 pgs.
"U.S. Appl. No. 13/837,480, Non Final Office Action dated Sep. 13, 2016", 9 pgs.
"U.S. Appl. No. 13/837,480, Response filed Jan. 11, 2016 to Non Final Office Action dated Aug. 11, 2015", 14 pgs.
"U.S. Appl. No. 13/837,480, Response filed Jul. 25, 2016 to Final Office Action dated May 23, 2016", 13 pgs.
"U.S. Appl. No. 13/837,480, Response filed Nov. 5, 2014 to Restriction Requirement dated Sep. 16, 2014", 3 pgs.
"U.S. Appl. No. 13/837,480, Restriction Requirement dated Sep. 16, 2014", 6 pgs.
"U.S. Appl. No. 13/839,280, Final Office Action dated Jan. 23, 2017", 14 pgs.
"U.S. Appl. No. 13/839,280, Final Office Action dated Apr. 10, 2015", 17 pgs.
"U.S. Appl. No. 13/839,280, Non Final Office Action dated Apr. 7, 2016", 16 pgs.
"U.S. Appl. No. 13/839,280, Non Final Office Action dated Jul. 17, 2014", 12 pgs.
"U.S. Appl. No. 13/839,280, Response filed Mar. 17, 2014 to Restriction Requirement dated Jan. 15, 2014", 5 pgs.
"U.S. Appl. No. 13/839,280, Response filed Aug. 29, 2016 to Non Final Office Action dated Apr. 7, 2016", 15 pgs.
"U.S. Appl. No. 13/839,280, Response filed Oct. 12, 2015 to Final Office Action dated Apr. 10, 2015", 9 pgs.
"U.S. Appl. No. 13/839,280, Response filed Oct. 17, 2014 to Non Final Office Action dated Jul. 17, 2014", 19 pgs.
"U.S. Appl. No. 13/839,280, Restriction Requirement dated Jan. 15, 2014", 6 pgs.
"U.S. Appl. No. 13/840,129, Final Office Action dated Jun. 18, 2015", 9 pgs.
"U.S. Appl. No. 13/840,129, Non Final Office Action dated Oct. 23, 2014", 8 pgs.
"U.S. Appl. No. 13/840,129, Response filed Feb. 23, 2015 to Non Final Office Action dated Oct. 23, 2014", 15 pgs.
"U.S. Appl. No. 13/840,129, Restriction Requirement dated Mar. 14, 2014", 6 pgs.

(56) References Cited

OTHER PUBLICATIONS

"U.S. Appl. No. 13/840,562, Final Office Action dated Jan. 20, 2016", 14 pgs.
"U.S. Appl. No. 13/840,562, Non Final Office Action dated Apr. 24, 2015", 23 pgs.
"U.S. Appl. No. 13/840,562, Non Final Office Action dated Sep. 30, 2014", 19 pgs.
"U.S. Appl. No. 13/840,562, Response filed Mar. 21, 2014 to Restriction Requirement dated Jan. 23, 2014", 9 pgs.
"U.S. Appl. No. 13/840,562, Response filed Apr. 18, 2016 to Final Office Action dated Jan. 20, 2016", 18 pgs.
"U.S. Appl. No. 13/840,562, Response filed Jul. 29, 2015 to Non Final Office Action dated Apr. 24, 2015", 13 pgs.
"U.S. Appl. No. 13/840,562, Response filed Dec. 30, 2014 to Non Final Office Action dated Sep. 30, 2014", 17 pgs.
"U.S. Appl. No. 13/840,562, Restriction Requirement dated Jan. 23, 2014", 9 pgs.
"U.S. Appl. No. 13/841,083, Examiner Interview dated Feb. 24, 2017", 1 pg.
"U.S. Appl. No. 13/841,083, Examiner Summary", 1 pg.
"U.S. Appl. No. 13/841,083, Final Office Action dated Sep. 9, 2016", 10 pgs.
"U.S. Appl. No. 13/841,083, Non Final Office Action dated Jan. 29, 2016", 11 pgs.
"U.S. Appl. No. 13/841,083, Non Final Office Action dated Feb. 24, 2017", 12 pgs.
"U.S. Appl. No. 13/841,083, Non Final Office Action dated Jul. 15, 2015", 8 pgs.
"U.S. Appl. No. 13/841,083, Non Final Office Action dated Dec. 10, 2014", 12 pgs.
"U.S. Appl. No. 13/841,083, Response filed Apr. 10, 2015 to Non Final Office Action dated Dec. 10, 2014", 17 pgs.
"U.S. Appl. No. 13/841,083, Response filed Apr. 28, 2016 to Non Final Office Action dated Jan. 29, 2016", 11 pgs.
"U.S. Appl. No. 13/841,083, Response filed Aug. 27, 2014 to Restriction Requirement dated Jul. 21, 2014", 3 pgs.
"U.S. Appl. No. 13/841,083, Response filed Oct. 13, 2015 to Non Final Office Action dated Jul. 15, 2015", 10 pgs.
"U.S. Appl. No. 13/841,083, Response filed Nov. 29, 2016 to Final Office Action dated Sep. 9, 2016", 12 pgs.
"U.S. Appl. No. 13/841,083, Restriction Requirement dated Jul. 21, 2014", 6 pgs.
"U.S. Appl. No. 13/841,103, Final Office Action dated Aug. 13, 2015", 13 pgs.
"U.S. Appl. No. 13/841,103, Final Office Action dated Dec. 14, 2016", 24 pgs.
"U.S. Appl. No. 13/841,103, Non Final Office Action dated Jun. 7, 2016", 16 pgs.
"U.S. Appl. No. 13/841,103, Non Final Office Action dated Dec. 4, 2014", 10 pgs.
"U.S. Appl. No. 13/841,103, Response filed Jan. 13, 2016 to Final Office Action dated Aug. 13, 2015", 11 pg.
"U.S. Appl. No. 13/841,103, Response filed Apr. 18, 2016 to Restriction Requirement dated Feb. 19, 2016", 8 pgs.
"U.S. Appl. No. 13/841,103, Response filed May 4, 2015 to Non Final Office Action dated Dec. 4, 2014", 18 pgs.
"U.S. Appl. No. 13/841,103, Response filed Aug. 27, 2014 to Restriction Requirement dated Jul. 21, 2014", 3 pgs.
"U.S. Appl. No. 13/841,103, Response filed Aug. 31, 2016 to Non Final Office Action dated Jun. 7, 2016", 15 pgs.
"U.S. Appl. No. 13/841,103, Restriction Requirement dated Feb. 19, 2016", 7 pgs.
"U.S. Appl. No. 13/841,103, Restriction Requirement dated Jul. 21, 2014", 6 pgs.
"U.S. Appl. No. 14/050,950, Final Office Action dated Jun. 17, 2016", 9 pgs.
"U.S. Appl. No. 14/050,950, Non Final Office Action dated Nov. 19, 2015", 13 pgs.
"U.S. Appl. No. 14/050,950, Notice of Allowance dated Oct. 6, 2016", 12 pgs.
"U.S. Appl. No. 14/050,950, Response filed Feb. 19, 2016 to Non Final Office Action dated Nov. 19, 2015", 11 pgs.
"U.S. Appl. No. 14/050,950, Response filed Jun. 23, 2015 to Restriction Requirement dated Apr. 23, 2015", 1 pgs.
"U.S. Appl. No. 14/050,950, Response filed Aug. 17, 2016 to Final Office Action dated Jun. 17, 2016", 8 pgs.
"U.S. Appl. No. 14/050,950, Restriction Requirement dated Apr. 23, 2015", 7 pgs.
"U.S. Appl. No. 14/271,722, Notice of Allowance dated Jan. 25, 2016", 13 pgs.
"U.S. Appl. No. 14/271,722, Preliminary Amendment filed May 7, 2014", 9 pgs.
"U.S. Appl. No. 14/803,414, Preliminary Amendment filed Sep. 16, 2015", 7 pgs.
"U.S. Appl. No. 14/803,414, Response filed Dec. 19, 2016 to Restriction Requirement dated Oct. 20, 2016", 7 pgs.
"U.S. Appl. No. 14/803,414, Restriction Requirement dated Oct. 20, 2016", 7 pgs.
"U.S. Appl. No. 14/803,414, Supplemental Preliminary Amendment Filed Feb. 3, 2016", 8 pgs.
"U.S. Appl. No. 14/808,828, Amendment Under 37 C.F.R. § 1.312 Filed", 6 pgs.
"U.S. Appl. No. 14/808,828, Non Final Office Action dated Dec. 8, 2016", 10 pgs.
"U.S. Appl. No. 14/808,828, Notice of Allowance dated May 19, 2017", 9 pgs.
"U.S. Appl. No. 14/808,828, Preliminary Amendment filed Jul. 24, 2015", 12 pgs.
"U.S. Appl. No. 14/808,828, Response filed Mar. 8, 2017 to Non Final Office Action dated Dec. 8, 2016", 9 pgs.
"U.S. Appl. No. 14/808,828, Response filed Oct. 3, 2016 to Restriction Requirement dated Aug. 2, 2016", 7 pgs.
"U.S. Appl. No. 14/808,828, Restriction Requirement dated Aug. 2, 2016", 6 pgs.
"U.S. Appl. No. 14/808,828, Supplemental Preliminary Amendment filed Jul. 27, 2015", 10 pgs.
"U.S. Appl. No. 14/808,828, Supplemental Preliminary Amendment filed Oct. 6, 2015", 7 pgs.
"U.S. Appl. No. 14/830,977, Final Office Action dated Oct. 20, 2016", 12 pgs.
"U.S. Appl. No. 14/830,977, Non Final Office Action dated Apr. 13, 2016", 16 pgs.
"U.S. Appl. No. 14/830,977, Response filed Jan. 20, 2017 to Final Office Action dated Oct. 20, 2016", 27 pgs.
"U.S. Appl. No. 14/830,977, Response filed Jul. 13, 2016 to Non Final Office Action dated Apr. 13, 2016", 10 pgs.
"U.S. Appl. No. 14/841,086, Examiners Interview Summary dated Nov. 7, 2016", 3 pgs.
"U.S. Appl. No. 14/973,913, Preliminary Amendment filed Mar. 2, 2016", 10 pgs.
"Application Serial No. 14709014.6, Response filed Feb. 27, 2017 to Non Final Office Action dated Oct. 20, 2016", 22 pgs.
"U.S. Appl. No. 13/840,129, Response filed May 14, 2014 to Restriction Requirement dated Mar. 14, 2014", 3 pgs.
"Arthritis", Mayo Clinic, (Jan. 22, 2013), 1-5.
"Arthritis", [Online]. Retrieved from the Internet: Wayback Machine <URL:http://www.mayoclinic.org/diseases-conditions/arthritis/basics/treatment/con-20034095 >, (2014), 5 pgs.
"Australian Application Serial No. 2010292553, First Examiner Report dated Feb. 7, 2014", 3 pgs.
"Australian Application Serial No. 2011296356, Amendment filed Jun. 3, 2014", 21 pgs.
"Australian Application Serial No. 2011296356, First Examiner Report dated Jun. 10, 2014", 7 pgs.
"Australian Application Serial No. 2011296356, Response filed Jun. 11, 2015 to First Examiner Report dated Jun. 10, 2014", 20 pgs.
"Bio-Gel P Polyacrylamide Gel", Instruction Manual, downloaded on Jun. 20, 2012 from [Online] retrieved from internet: <www.bio-rad.com/webmaster/pdfs/9154_Bio-Gel P.pdf>, 1-14.
"Bio-Rad Laboratories. Bio-Gel P Polyacrylamide Gel Instruction Manual", [Online]. Retrieved from the Internet: <www.bio-rad.com/webmaster/pdfs/9154 Bio-Gel P.pdf>, (Jun. 20, 2012), 14 pgs.
"BioCUE™ Platelet Concentration System", (Jun. 2010), 2 pgs.

(56) References Cited

OTHER PUBLICATIONS

"Canadian Application No. 2,810,202, Response filed Jan. 26, 2017 to Non Final Office Action dated Aug. 11, 2016", 8 pgs.
"Canadian Application Serial No. 2,772,067, Office Action dated Jan. 8, 2015", 3 pgs.
"Canadian Application Serial No. 2,772,067, Office Action dated Nov. 24, 2015", 3 pgs.
"Canadian Application Serial No. 2,772,067, Response filed Mar. 1, 2016 to Office Action dated Nov. 24, 2015", 7 pgs.
"Canadian Application Serial No. 2,772,067, Response filed Jul. 8, 2015 to Office Action dated Jan. 8, 2015", 24 pgs.
"Canadian Application Serial No. 2,772,069, Office Action dated Jul. 20, 2016", 5 pgs.
"Canadian Application Serial No. 2,772,069, Office Action dated Sep. 16, 2015", 3 pgs.
"Canadian Application Serial No. 2,772,084, Office Action dated Jun. 11, 2015", 3 pgs.
"Canadian Application Serial No. 2,810,202, Office Action dated Jul. 2, 2015", 5 pgs.
"Canadian Application Serial No. 2,810,202, Office Action dated Aug. 11, 2016", 4 pgs.
"Canadian Application Serial No. 2,810,202, Response filed Dec. 30, 2015 to Office Action dated Jul. 2, 2015", 19 pgs.
"Canadian Application Serial No. 2,810,202, Voluntary Amendment filed Jan. 13, 2014", 12 pgs.
"Canadian Application Serial No. 2,905,552, Voluntary Amendment filed Sep. 11, 2015".
"Canadian Application Serial No. 2,906,310, Voluntary Amendment filed Sep. 14, 2015", 2 pgs.
"Caps for Corning® and Costar® Plastic Labware", Technical Bulletin, (Dec. 2008), 2 pgs.
"Cell Isolation Techniques, Methods and Materials, Working with Enzymes", Worthington Biochemical Corp, (2004), 9 pgs.
"Cell Isolation Theory, Tissue Types", Worthington Biochemical Corp, (2004), 5 pgs.
"Centrifuge Tubes", Corning Costar, (1996/1997), 76-77.
"Chinese Application Serial No. 201080019707.7, Office Action dated Jun. 30, 2014", in English, 7 pgs.
"Chinese Application Serial No. 2010800428565, Non Final Office Action dated Jan. 22, 2013", W/ English Translation, 10 pgs.
"Chinese Application Serial No. 2010800428565, Non Final Office Action dated Feb. 14, 2014", W/ English Translation, 5 pgs.
"Chinese Application Serial No. 2010800428565, Non Final Office Action dated Sep. 10, 2013", W/ English Translation, 10 pgs.
"Chinese Application Serial No. 2010800428565, Response filed Apr. 29, 2014 to Non Final Office Action dated Feb. 14, 2014", W/ English Claims, 7 pgs.
"Chinese Application Serial No. 2010800428565, Response filed Aug. 6, 2013 to Non Final Office Action dated Jan. 22, 2013", W/ English Claims, 9 pgs.
"Chinese Application Serial No. 2010800428565,Response filed Nov. 25, 2013 to Non Final Office Action dated Sep. 10, 2013", W/ English Claims, 10 pgs.
"Chinese Application Serial No. 2010800447744, Decision on rejection dated Nov. 15, 2014", W/ English Translation, 10 pgs.
"Chinese Application Serial No. 2010800447744, Notification of Reexamination dated Feb. 23, 2016", W/ English Translation, 9 pgs.
"Chinese Application Serial No. 2010800447744, Office Action dated Jan. 31, 2013", W/ English Translation, 12 pgs.
"Chinese Application Serial No. 2010800447744, Office Action dated Apr. 30, 2014", W/ Machine Translation, 13 pgs.
"Chinese Application Serial No. 2010800447744, Office Action dated Oct. 22, 2013", W/ English Translation, 10 pgs.
"Chinese Application Serial No. 2010800447744, Response filed Jan. 6, 2014 to Office Action dated Oct. 22, 2013", with English translation of claims, 27 pgs.
"Chinese Application Serial No. 2010800447744, Response filed Feb. 19, 2015 to Decision on rejection dated Nov. 15, 2014", W/ English Translation, 13 pgs.
"Chinese Application Serial No. 2010800447744, Response filed Apr. 11, 2016 to Notification of Reexamination dated Feb. 23, 2016", W/ English Claims, 23 pgs.
"Chinese Application Serial No. 2010800447744, Response filed Jun. 17, 2013 to Office Action dated Jan. 31, 2013", W/ Machine Translation, 11 pgs.
"Chinese Application Serial No. 2010800447744, Response filed Jul. 15, 2014 to Office Action dated Apr. 30, 2014", with English translation of claims, 25 pgs.
"Chinese Application Serial No. 2011800457327, Office Action dated Mar. 26, 2015", W/ Machine Translation, 18 pgs.
"Chinese Application Serial No. 2011800457327, Office Action dated Jul. 16, 2014", W/ Machine Translation, 16 pgs.
"Chinese Application Serial No. 2011800457327, Office Action dated Sep. 28, 2015", W/ Machine Translation, 14 pgs pgs.
"Chinese Application Serial No. 2011800457327, Response filed Jun. 10, 2015 to Office Action dated Mar. 26, 2015", W/ English Claims, 22 pgs.
"Chinese Application Serial No. 2011800457327, Response filed Dec. 1, 2014 to Office Action dated Jul. 16, 2014", W/ English Claims, 19 pgs.
"Chinese Application Serial No. 201280030026.X, Office Action dated Nov. 21, 2014", w/ English Translation, 27 pgs.
"Chinese Application Serial No. 201480027178.3, Voluntary Amendment filed Jul. 15, 2016", w/English claims, 35 pgs.
"Chinese Application Serial No. 201480027408.6, Voluntary Amendment dated Jun. 8, 2016", W/ English Claims, 50 pgs.
"Chinese Application Serial No. 201480027541.1, Voluntary Amendment filed May 5, 2016", w/ English Claims, 15 pgs.
"Clotalyst® Autologous Clotting Factor", "Would you like to have an autologous thrombin for rapid clotting and haemostasis?" Biomet Biologics, (Jan. 2007), 16 pgs.
"Corning® 15 and 50 ml Centrifuge Tubes", Life Sciences. Corning Incorporated., (Jun. 2005), 2 pgs.
"Cytori Celution Cell Concentrate Device", Exhibit 14, 501(k) Summary, FDA approval K060482, (Sep. 28, 2006), 7 pgs.
"European Application No. 09715775.4, Non Final Office Action dated Apr. 26, 2011", 5 pgs.
"European Application No. 09715775.4, Preliminary Amendment filed Sep. 22, 2010", 9 pgs.
"European Application No. 09715775.4,Response filed Oct. 12, 2011 to Non Final Office Action dated Apr. 26, 2011", 20 pgs.
"European Application No. 09715775.4,Supplemental Preliminary Amendment filed Nov. 17, 2010", 12 pgs.
"European Application No. 15184504.7, Response filed Jan. 25, 2017 to Non Final Office Action dated Sep. 16, 2016", 10 pgs.
"European Application Serial No. 10712677.3, Examination Notification Art. 94(3) dated Jun. 5, 2013", 5 pgs.
"European Application Serial No. 10749582.2, Communication Pursuant to Article 94(3) EPC dated May 10, 2016", 4 pgs.
"European Application Serial No. 10749582.2, Communication Pursuant to Article 94(3) EPC dated Sep. 10, 2013", 5 pgs.
"European Application Serial No. 10749582.2, Examination Notification Art. 94(3) dated Dec. 8, 2014", 7 pgs.
"European Application Serial No. 10749582.2, Response filed Jan. 3, 2014 to Communication Pursuant to Article 94(3) EPC dated Sep. 10, 2013", 12 pgs.
"European Application Serial No. 10749582.2, Response filed Apr. 16, 2015 to Communication Pursuant to Article 94(3) EPC dated Dec. 8, 2014", 14 pgs.
"European Application Serial No. 10749582.2, Response filed Aug. 26, 2016 to Communication Pursuant to Article 94(3) EPC dated May 10, 2016", 13 pgs.
"European Application Serial No. 10749582.2, Response filed Sep. 28, 2012 to Communication pursuant to Rules 161(2) and 162 EPC dated Apr. 3, 2012", 19 pgs.
"European Application Serial No. 10754379.5, Examination Notification Art. 94(3) dated Aug. 16, 2013", 5 pgs.
"European Application Serial No. 10754379.5, Examination Notification Art. 94(3) dated Dec. 15, 2014", 4 pgs.
"European Application Serial No. 10754379.5, Office Action dated Apr. 3, 2012", 2 pgs.

(56) References Cited

OTHER PUBLICATIONS

"European Application Serial No. 10754379.5, Response filed Feb. 17, 2014 to Examination Notification Art. 94(3) dated Aug. 16, 2013", 13 pgs.
"European Application Serial No. 10754379.5, Response filed Apr. 13, 2015 to Examination Notification Art. 94(3) dated Dec. 15, 2014", 8 pgs.
"European Application Serial No. 10754379.5, Response filed Sep. 28, 2012 to Office Action dated Apr. 3, 2012", 11 pgs.
"European Application Serial No. 10754613.7, Communication Pursuant to Article 94(3) EPC dated Sep. 16, 2013", 4 pgs.
"European Application Serial No. 10754613.7, Communication Pursuant to Article 94(3) EPC dated Nov. 13, 2015", 4 pgs.
"European Application Serial No. 10754613.7, Non Final Office Action dated Feb. 7, 2017", 5 pgs.
"European Application Serial No. 10754613.7, Response filed Mar. 14, 2014 to Communication Pursuant to Article 94(3) EPC dated Sep. 16, 2013", 15 pgs.
"European Application Serial No. 10754613.7, Response filed Mar. 15, 2016 to Communication Pursuant to Article 94(3) EPC dated Nov. 13, 2015", 26 pgs.
"European Application Serial No. 10754613.7, Response filed Oct. 1, 2012 to Communication pursuant to Rules 161(1) and 162 EPC dated Mar. 4, 2012", 15 pgs.
"European Application Serial No. 11754786.9, Communication Pursuant to Article 94(3) EPC dated Feb. 19, 2014", 4 pgs.
"European Application Serial No. 11754786.9, Examination Notification Art. 94(3) dated Oct. 8, 2014", 5 pgs.
"European Application Serial No. 11754786.9, Grounds for the decision dated Oct. 13, 2015", 7 pgs.
"European Application Serial No. 11754786.9, Response filed Feb. 6, 2015 to Communication Pursuant to Article 94(3) EPC dated Oct. 8, 2014", 9 pgs.
"European Application Serial No. 11754786.9, Response filed Aug. 13, 2014 to Communication Pursuant to Article 94(3) EPC dated Feb. 19, 2014", 10 pgs.
"European Application Serial No. 11754786.9, Response filed Nov. 4, 2013 to Communication pursuant to Rules 161(1) and 162 EPC dated Apr. 24, 2013", 21 pgs.
"European Application Serial No. 11754786.9, Summons to Attend Oral Proceedings mailed Mar. 10, 2015", 3 pgs.
"European Application Serial No. 12195882.1, Extended European Search Report dated Jan. 31, 2013", 5 pgs.
"European Application Serial No. 12195882.1, Non Final Office Action dated Jun. 30, 2014", 4 pgs.
"European Application Serial No. 12195882.1, Response filed Sep. 11, 2013 to Extended European Search Report dated Jan. 31, 2013", 16 pgs.
"European Application Serial No. 12195882.1, Response filed Oct. 29, 2014 to Non Final Office Action dated Jun. 30, 2014", 18 pgs.
"European Application Serial No. 13165543.3, Extended European Search Report dated Jul. 1, 2013", 6 pgs.
"European Application Serial No. 13165543.3, Non Final Office Action dated Jun. 27, 2014", 5 pgs.
"European Application Serial No. 13165543.3, Response filed Jan. 14, 2014 to Extended European Search Report dated Jul. 1, 2013", 11 pgs.
"European Application Serial No. 13165543.3, Response filed Oct. 24, 2014 to Non Final Office Action dated Jun. 27, 2014", 6 pgs.
"European Application Serial No. 14707069.2, Communication Pursuant to Article 94(3) EPC dated Nov. 15, 2016", 7 pgs.
"European Application Serial No. 14707069.2, Response filed May 23, 2016 to Communication pursuant to Rules 161(1) and 162 EPC dated Nov. 12, 2015", 12 pgs.
"European Application Serial No. 14707909.9, Communication Pursuant to Article 94(3) EPC dated Jul. 22, 2016", 9 pgs.
"European Application Serial No. 14707909.9, Communication Pursuant to Article 94(3) EPC dated Dec. 16, 2016", 5 pgs.
"European Application Serial No. 14707909.9, Preliminary Amendment filed on May 13, 2016", 14 pgs.
"European Application Serial No. 14707909.9, Response filed Dec. 6, 2016 to Communication Pursuant to Article 94(3) EPC dated Jul. 22, 2016", 11 pgs.
"European Application Serial No. 14709014.6, Communication Pursuant to Article 94(3) EPC dated Oct. 20, 2016", 12 pgs.
"European Application Serial No. 14709014.6, Office Action dated Nov. 19, 2015", 2 pgs.
"European Application Serial No. 14709014.6, Response filed May 27, 2016 to Office Action dated Nov. 19, 2015", 15 pgs.
"European Application Serial No. 14709803.2, Response filed May 16, 2016 to Communication pursuant to Rules 161(1) and 162 EPC dated Nov. 5, 2015", 14 pgs.
"European Application Serial No. 14714491.9, Response filed Aug. 1, 2016 to Communication Pursuant to Rules 161 and 162 EPC dated Jan. 21, 2016", 11 pgs.
"European Application Serial No. 14724817.3, Office Action dated Oct. 27, 2015", 2 pgs.
"European Application Serial No. 14724817.3, Response filed May 6, 2016 to Communication pursuant to Rules 161(1) and 162 EPC dated Oct. 27, 2015", 13 pgs.
"European Application Serial No. 14729994.5, Response filed May 9, 2016 to Communication pursuant to Rules 161(1) and 162 EPC dated Oct. 30, 2015", 14 pgs.
"European Application Serial No. 15184504.7, Communication Pursuant to Article 94(3) EPC dated Feb. 13, 2016", 5 pgs.
"European Application Serial No. 15184504.7, Communication Pursuant to Article 94(3) EPC dated Feb. 13, 2017", 6 pgs.
"European Application Serial No. 15184504.7, Communication Pursuant to Article 94(3) EPC dated Sep. 16, 2016", 5 pgs.
"European Application Serial No. 15184504.7, Extended European Search Report dated Oct. 20, 2015", 7 pgs.
"Fibrostik™ Plasma Concentrator", Attention Operating Surgeon, Cell Factor Technologies, Inc., (Jul. 2003), 2 pgs.
"Frequently Asked Questions, 1. Kits, 2. Enzymes", Worthington Biochemical Corp, (2003), 3 pgs.
"GPS® II Platelet Concentrate System: The New Gold Standard", Product Brochure, (Sep. 2006), 14 pgs.
"GPS® II System, Gravitational Platelet Separation System", User Manual—Cell Factor Technologies, Inc., [Online]. Retrieved from the Internet: <http://www.cellfactortech.com/global_products.cfm,>, (Sep. 16, 2005), 13 pgs.
"GPS® II System, Gravitational Platelet Separation System, Accelerating the Body's Natural Healing Process", Cell Factor Technologies, Inc., [Online] retrieved form the internet: <http://www.cellfactortech.com/global_products.cfm>, printed Sep. 16, 2005, (2005), 16 pgs.
"GPS® III Platelet Separation System, Leadership through Technology", Biomet Biologics, Inc, (Jul. 2007), 8 pgs.
"GPS® Platelet Concentrate System", Cell Factor Technologies, Inc Biomet Orthopaedics, Inc., (Feb. 29, 2004), 9 pgs.
"Hemocor HPH® Hemoconcentrator", Minntech® Filtration Technologies Group, Minntech Corporation (2004), <http://www.minntech.com/ftg/products/hph/index.html>, (Jul. 15, 2004), 2 pgs.
"Increasing bone graft bioactivity through reproducible concentrations of natural growth factors", Symphony II Platelet Concentrate System/PCS brochure, (Jan. 2003), 8 pgs.
"International Application Serial No. PCT/US2003/016506, International Search Report dated Oct. 13, 2003", 2 pgs.
"International Application Serial No. PCT/US2007/012587, International Search Report dated Nov. 6, 2007", 2 pgs.
"International Application Serial No. PCT/US2008/004687, International Preliminary Report on Patentability dated Aug. 13, 2009", 19 pgs.
"International Application Serial No. PCT/US2008/004687, International Search Report dated Jul. 2, 2008", 3 pgs.
"International Application Serial No. PCT/US2008/004687, Written Opinion dated Mar. 17, 2009", 5 pgs.
"International Application Serial No. PCT/US2008/004687, Written Opinion dated Jul. 2, 2008", 5 pgs.
"International Application Serial No. PCT/US2009/035541, International Preliminary Report on Patentability dated Aug. 3, 2010", 8 pgs.

(56) References Cited

OTHER PUBLICATIONS

"International Application Serial No. PCT/US2009/035541, International Search Report dated Jun. 16, 2009", 3 pgs.
"International Application Serial No. PCT/US2009/035541, Written Opinion dated Jun. 16, 2009", 7 pgs.
"International Application Serial No. PCT/US2009/035564, International Preliminary Examination Report dated Aug. 31, 2010", 6 pgs.
"International Application Serial No. PCT/US2009/035564, International Search Report dated Jul. 3, 2009", 3 pgs.
"International Application Serial No. PCT/US2009/035564, Written Opinion dated Jul. 3, 2009", 5 pgs.
"International Application Serial No. PCT/US2010/029957, International Preliminary Report on Patentability dated Oct. 13, 2011", 10 pgs.
"International Application Serial No. PCT/US2010/029957, International Search Report dated Jul. 30, 2010", 6 pgs.
"International Application Serial No. PCT/US2010/029957, Written Opinion dated Jul. 30, 2010", 9 pgs.
"International Application Serial No. PCT/US2010/041942, International Preliminary Report on Patentability dated Jan. 26, 2012", 9 pgs.
"International Application Serial No. PCT/US2010/041942, International Search Report dated Oct. 8, 2010", 3 pgs.
"International Application Serial No. PCT/US2010/041942, Written Opinion dated Oct. 8, 2010", 8 pgs.
"International Application Serial No. PCT/US2010/046821, International Preliminary Report on Patentability dated Mar. 8, 2012", 6 pgs.
"International Application Serial No. PCT/US2010/046821, International Search Report dated Jul. 22, 2011", 4 pgs.
"International Application Serial No. PCT/US2010/046821, Written Opinion dated Jul. 22, 2011",4 pgs.
"International Application Serial No. PCT/US2011/031954, International Search Report dated Aug. 9, 2011", 4 pgs.
"International Application Serial No. PCT/US2011/031954, Written Opinion dated Aug. 9, 2011",9 pgs.
"International Application Serial No. PCT/US2011/045290, International Search Report dated Nov. 7, 2011", 5 pgs.
"International Application Serial No. PCT/US2011/045290, Written Opinion dated Nov. 7, 2011",5 pgs.
"International Application Serial No. PCT/US2012/034104, International Preliminary Report on Patentability dated Oct. 31, 2013", 7 pgs.
"International Application Serial No. PCT/US2012/034104, International Search Report dated Oct. 29, 2012", 5 pgs.
"International Application Serial No. PCT/US2012/034104, Written Opinion dated Oct. 29, 2012", 6 pgs.
"International Application Serial No. PCT/US2013/056793, International Preliminary Report on Patentability dated Mar. 12, 2015", 8 pgs.
"International Application Serial No. PCT/US2013/056793, International Search Report dated Dec. 5, 2013", 3 pgs.
"International Application Serial No. PCT/US2013/056793, Written Opinion dated Dec. 5, 2013", 6 pgs.
"International Application Serial No. PCT/US2014/016384, International Preliminary Report on Patentability dated Sep. 24, 2015", 16 pgs.
"International Application Serial No. PCT/US2014/016384, International Search Report dated Oct. 9, 2014", 10 pgs.
"International Application Serial No. PCT/US2014/016384, Written Opinion dated Oct. 9, 2014", 14 pgs.
"International Application Serial No. PCT/US2014/016421, International Preliminary Report on Patentability dated Sep. 24, 2015", 16 pgs.
"International Application Serial No. PCT/US2014/016421, International Search Report dated Jul. 24, 2014", 8 pgs.
"International Application Serial No. PCT/US2014/016421, Written Opinion dated Jul. 24, 2014", 14 pgs.
"International Application Serial No. PCT/US2014/016895, International Preliminary Report on Patentability dated Sep. 24, 2015", 16 pgs.
"International Application Serial No. PCT/US2014/016895, International Search Report dated Jul. 24, 2014", 9 pgs.
"International Application Serial No. PCT/US2014/016895, Written Opinion dated Jul. 24, 2014", 14 pgs.
"International Application Serial No. PCT/US2014/016900, International Preliminary Report on Patentability dated Sep. 24, 2015", 9 pgs.
"International Application Serial No. PCT/US2014/016900, International Search Report dated May 12, 2014", 5 pgs.
"International Application Serial No. PCT/US2014/016900, Written Opinion dated May 12, 2014", 8 pgs.
"International Application Serial No. PCT/US2014/021707, International Preliminary Report on Patentability dated Sep. 24, 2015", 16 pgs.
"International Application Serial No. PCT/US2014/021707, International Search Report dated Jul. 24, 2014", 8 pgs.
"International Application Serial No. PCT/US2014/021707, Written Opinion dated Jul. 24, 2014", 14 pgs.
"International Application Serial No. PCT/US2014/023091, International Preliminary Report on Patentability dated Sep. 24, 2015", 11 pgs.
"International Application Serial No. PCT/US2014/023091, International Search Report dated Oct. 9, 2014", 7 pgs.
"International Application Serial No. PCT/US2014/023091, Written Opinion dated Oct. 9, 2014", 9 pgs.
"International Application Serial No. PCT/US2014/028942, International Preliminary Report on Patentability dated Sep. 24, 2015", 15 pgs.
"Isolation of Granulocytes From Human Peripheral Blood by Density Gradient Centrifugation", Miltenyi Biotec GmbH, (2008), 2 pgs.
"Japanese Application Serial No. 2010-503066, Office Action dated Jan. 22, 2013", w/ English Translation, 17 pgs.
"Japanese Application Serial No. 2012-503768, Office Action dated May 20, 2014", w/ English Translation, 5 pgs.
"Japanese Application Serial No. 2012-520742, Office Action dated Sep. 9, 2014", w/ English Translation, 6 pgs.
"Japanese Application Serial No. 2012-526988, Office Action dated Oct. 1, 2013", W/ English Translation, 4 pgs.
"Japanese Application Serial No. 2012-526988, Response filed Mar. 3, 2014 to Office Action dated Oct. 1, 2013", W/ English Claims, 21 pgs.
"Japanese Application Serial No. 2012-526990, Examiners Decision of Final Refusal dated Jun. 3, 2016", W/ English Translation, 6 pgs.
"Japanese Application Serial No. 2012-526990, Office Action dated Jun. 26, 2015", W/ English Translation, 12 pgs.
"Japanese Application Serial No. 2012-526990, Office Action dated Aug. 5, 2014", W/ Machine Translation, 4 pgs.
"Japanese Application Serial No. 2012-526990, Response filed Dec. 5, 2014 to Office Action dated Aug. 5, 2014", W/ English Claims, 19 pgs.
"Japanese Application Serial No. 2012-526990, Response filed Dec. 25, 2015 to Office Action dated Jun. 26, 2015", W/ English Translation, 14 pgs.
"Japanese Application Serial No. 2012-527030, Office Action dated Jun. 12, 2015", W/ English Translation, 2 pgs.
"Japanese Application Serial No. 2013-174962, Notice of Reasons for Rejection dated Jul. 31, 2015", W/ English Translation, 10 pgs.
"Japanese Application Serial No. 2013-174962, Office Action dated Sep. 12, 2014", W/ English Translation, 6 pgs.
"Japanese Application Serial No. 2013-174962, Response filed Mar. 12, 2015 to Office Action dated Sep. 12, 2014", W/ English Translation, 18 pgs.
"Japanese Application Serial No. 2013-174962, Response filed Oct. 30, 2015 to Notice of Reasons for Rejection dated Jul. 31, 2015", W/ English Claims, 16 pgs.
"Japanese Application Serial No. 2013-527119, Examiners Decision of Final Refusal dated Oct. 18, 2016", W/ English Translation, 9 pgs.

(56) References Cited

OTHER PUBLICATIONS

"Japanese Application Serial No. 2013-527119, Office Action dated Mar. 1, 2016", W/ English Translation, 12 pgs.
"Japanese Application Serial No. 2013-527119, Office Action dated Jun. 12, 2015", W/ English Translation, 11 pgs.
"Japanese Application Serial No. 2013-527119, Response filed Aug. 1, 2016 to Office Action dated Mar. 1, 2016", W/ English Claims, 13 pgs.
"Japanese Application Serial No. 2013-527119, Response filed Oct. 1, 2015 to Office Action dated Jun. 12, 2015", W/ English Claims, 12 pgs.
"Japanese Application Serial No. 2014-024420, Preliminary Notice of Reasons for Rejection dated Feb. 24, 2015", w/ English Translation, 15 pgs.
"Knee Cartilage Implantation Carticel™, Autologous Cultured Chondrocyte Implantation", The Sports Medicine Center, [Online]. Retrieved from the Internet: <http://www.orthoassociates.com/carticel.htm>, (Apr. 6, 2006), 7 pgs.
"Letter CryoSeal FS System. Vaccines, Blood & Biologics", FDA U.S. Food and Drug Administation., http://www.fda.gov/BiologicsBioodVaccines/BioodBioodProducts/ApprovedProducts/Premarket ApprovalsPMAs/ucm091631.htm, (Jul. 26, 2007), 21 pgs.
"MarrowStim™ Concentration Kit Peripheral Arterial Disease (PAD) Study", Retriewed From Intenet : <http://www.biomet.com/patients/clinical recruitment padstudy.cfm>, (Jul. 2, 2009), 2 pgs.
"MarrowsTim™ Concentration System", Biomet Biologics, Inc, (Feb. 15, 2008), 20 pgs.
"Medical Applications: Blood Filtration", Minntech® Filtration Technologies Group, Minntech Corporation (2004), <http://www.minntech.com/ftg/industries/medical/blood_filter.html>, (Jul. 15, 2004), 1 pg.
"Minivalve international: duckbill valves—du 054.001 sd", [Online]. Retrieved from the Internet: <http://www.minivalve.com/htm/DV054.htm>, 1 pg.
"Momentive Silopren*LSR 2050", (Jun. 30, 2014), 3 pg.
"Plasmax Plasma Concentrate", Biomet Biologics, Inc, Brochure, (2006), 6 pgs.
"Plasmax® Plasma Concentration System", Biomet Biologics, (Mar. 2007), 18 pgs.
"Platelet Rich Plasma (PRP)", The Stone Clinic, (May 2006), 2 pgs.
"Prosys PRP Kit", Tozai Holdings, Inc. EC21 Global B2B Marketplace, Retrieved From Internet : <http://www.ec21.com/product-details/Prosys-PRP-Kit--5467061.html Printed from Web>, (Jul. 18, 2011), 5 pgs.
"Renaflo® II Hemofilter", Minntech® Filtration Technologies Group, Minntech Corporation (2004), <http://www.minntech.com/ftg/products/renaflo/index.html>, (Jul. 15, 2004), 2 pgs.
"Shoulder Recovery with the GPS® Platelet Concentrate System, Rotator Cuff Surgical Techniques", Biomet Biologics, Inc., (2004), 6 pgs.
"Sigma-Aldrich® Alkaline Phosphatase (Procedure No. 85), drug fact sheet", Sigma-Aldrich, (2003), 1-2.
"SmartPrep PRP-20 Procedure Pack—Instructions for Use", Harvest, 12 pgs.
"ThermoGenesis Corp. to Supply Autologous Thrombin Kits to Biomet, Inc", noblood: Transfusion Alternatives Patient Blood Mangement, [Online]. Retrieved from the Internet: <URL: http://noblood.org/forum/threads/2128-ThermoGenesis-Corp-to-Supply-Autologous-Thrombin-Kits-to-Biomet-Inc>, (Apr. 5, 2005), 3 pgs.
"Trypsinizing cells", Bart's Cook Book, 1 pg.
"Update for veterinarians", Anonymous, [Online]. Retrieved from the Internet: <URL:http://vet.osu.edu/sites/default/files/documents/pdf/news/vmc/ovmaVeterinarianUp/documents/pdf/news/vmc/ovmaVeterinarianUp>, (Dec. 2012).
"Vernay Product Information Sheet, Umbrella Check Valve", Part No. V251010200, (Jul. 2013), 2 pgs.
"Vortech Concentration System Product", Biomet Biologics, Inc., (Aug. 2005), 16 pgs.

Aaron, "Stimulation of Experimental Endochondral Ossification by Low-Energy Pulsing Electromagnetic Fields", Journal of Bone and Mineral Research, (1989), 227-233.
Aaron, et al., "Therapeutic Effects of Electromagnetic Fields in the Stimulation of Connective Tissue Repair", Journal of Cellular Biochemistry, (1993), 42-46.
Aaron, et al., "Upregulation of basal TGFb1 levels by EMF coincident with chondrogenesis—implications for skeletal repair and tissue engineering", Journal of Orthopaedic Research, (2002), 233-240.
Aaron, Roy K., et al., "Acceleration of Experimental Endochondral Ossification by Biophysical Stimulation of the Progenitor Cell Pool", Journal of Orthopaedic Research, (1996), 582-589.
Aaron, Roy K., et al., "Power Frequency Fields Promote Cell Differentiation Coincident With an Increase in Transforming Growth Factor-?1 Expression", Bioelectromagnetics, (1999), 453-458.
Agu, R. U., et al., "The lung as a route for systemic delivery of therapeutic proteins and peptides", Respir Res.; vol. 2, (2001), pp. 198-209.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andia, Isabel, et al., "Platelet-rich plasma for managing pain and inflammation in osteoarthritis", Nature Reviews Rheumatology, vol. 9. No. 12., (Oct. 1, 2013), 721-730.
Anitua, Eduardo, et al., "Autologous platelets as a source of proteins for healing and tissue regeneration", Thromb Haemost, vol. 91, (2004), 4-15.
Arend, W, et al., "Interleukin-1 Receptor Antagonist: Role in Biology", Annu. Rev. Immunol., vol. 16, (1998), 27-55.
Badiavas, Evangelos V., et al., "Treatment of Chronic Wounds With Bone Marrow-Derived Cells", Arch Dermatol. 139, (Apr. 2003), 510-516.
Baltzer, A W, et al., "Autologous conditioned serum (Orthokine) is an effective treatment for knee osteoarthritis. Osteoarthritis Cartilage", (Feb. 1, 2009), 152-60.
Bang, N U, et al., "Plasma Protein Requirements for Human Platelet Aggregation", Acad Sci, 201, (1972), 280-299.
Becker, C, et al., "Efficacy of epidural perineural injections with autologous conditioned serum for lumbar radicular compression an Investigator-initiated, prospective, double-blind, reference-controlled study", (2007), 1803-1808.
Belal, Mahmoud Helmy, "Recombinant Human Platelet-Derived Growth Factor-BB: a promising role for fibroblast cell attachment in chronic periodontitis. A concentration-dependent effect on human cell adhesion: SEM study", Rev. Clin. Pesq. Odontol., Curitiba, v. 5, n. 3, (2009), p. 225-240.
Bendele, Alison M, et al., "Combination Benefit of Treatment With the Cytoki Ne Inhibitors interleukin-1 Receptor Antagonist and Pegylated Soluble Tumor Necrosis Factor Receptor Type I in animal models of Rheumatoid Arthritis", Arthritis & Rheumatism, Wiley, US, vol. 43, No. 1, (Dec. 1, 2000), 2648-2659.
Bendele, Alison M, et al., "Combination Benefit of Treatment With the Cytokine Inhibitors Interleukin-1 Receptor Antagonist and Pegylated Soluble Tumor Necrosis Factor Receptor Type I in Animal Models of Rheumatoid Arthritis", Arthritis & Rheumatism, J.B. Lippincott vol. 43, No. 12, (Dec. 1, 2000), 2648-2659.
Berguer, R, et al., "Warning: fatal reaction to the use of fibrin glue in deep hepatic wounds. Case reports", J Trauma 31, (1991), 408-411.
Berruyer, M, et al., "Immunization by bovine thrombin used with fibrin glue during cardiovascular operations. Development of thrombin and factor V inhibitors", J Thorac Cardiovasc Sura 105, (1993), 892-7.
Bielecki, T, et al., "Antibacterial effect of autologous platelet gel enriched with growth factors and toher acive substances", J Bone Joint Surg, vol. 89-B, No. 3, (Mar. 2007), 417-420.
Boomgaard, et al., "Pooled Platelet Concentrates Prepared by the Platelet-Rich-Plasma Method and Filtered with Three Different Filters and Stored for 8 Days", Vox Sanq, vol. 68, (Feb. 1995), 82-89.

(56) References Cited

OTHER PUBLICATIONS

Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research, (May 2006), 857-866.

Burnouf, T, "Blood-derived, tissue engineering biomaterials", Biomedical Engineering—Applications, Basis & Communications, val. 16, No. 6, (Dec. 6, 2004), 294-304.

Carpenter, et al., "Long-term storage of proteins", Current Protocols in Protein Science, (2002), 6 pgs.

Carpenter, et al., "Rationale Design of stable protein formulations—theory and practice", Rationale design of stable lyophilized protein formulations: theory and practice,, (2002), 109-133.

Casali, B, et al., "Fibrin glue from single-donation autologous plasmapheresis", Transfusion 32, (1992), 641-643.

Clayden, J D, et al., "Improved segmentation reproducibility in group tractography using a quantitative tract similarity measure", Neuroimage, Academic Press, Orlando, FL, US vol. 33, No. 2, (Nov. 1, 2006), 482-492.

Collier, B S, et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda Blood, vol. 47, No. 5, (May 1976).

Connolly, John, et al., "Development of an Osteogenic Bone-Marrow Preparation", The Journal of Bone and Joint SurQery, Incorporated. vol. 71-A, No. 5, (Jun. 1989), 684-691.

Connolly, John F., "Injectable Bone Marrow Preparations to Stimulate Osteogenic Repair", Clinical Orthopaedics and Related Research 313, (Apr. 1995), 8-18.

Dallari, et al., "Enhanced Tibial Osteotomy Healing with Use of Bone Grafts Supplemented with Platelet Gel or Platelet Gel and Bone Marrow Stromal Cells", The Journal of Bone and Joint Surgery, vol. 89, (2007), 2413-2420.

Dallari, et al., "In Vivo Study on the Healing of Bone Defects Treated with Bone Marrow Stromal Cells, Platelet-Rich Plasma, and Freeze-Dried Bone Allografts, Alone and in Combination", Healing of Bone Defects, Journal of Orthopaedic Research, (May 2006), 877-888.

Danis, V. A., et al., "Cytokine production by normal human monocytes: inter-subject variation and relationship to an IL-1 receptor antagonist (IL-IRa) gene polymorphism", Clin Exp Immunol; (99), (1995), p. 303-310.

Dawson, J, et al., "Effects of soluble interleukin-1 type II receptor on rabbit antigen-induced arthritis: Clinical, biochemical and histological assessment", Rheumatology (Oxford) vol. 38, No. 5, (May 5, 1999), 401-406.

Dayer, Jean-Michel, et al., "Adipose tissue has anti-inflammatory properties: focus on IL-1 receptor antagonist (IL-1Ra)", Annals of the New York Academy of Sciences, vol. 1069, (Jun. 2006), 444-53.

De Ugarte, et al., "Comparison of Multi-Lineage Cells from Human Adipose Tissue and Bone Marrow", Cells Tissues Organs 174, (2003), 101-109.

De Ugarte, et al., "Differential Expression of Stem Cell Mobilization-Associated Molecules on Multi-Lineage Cells from Adipose Tissue and Bone Marrow", Immunology Letters 89, (2003), 267-270.

De Wit, et al., "Experiments on the Preparation of Blood Components with the IBM 2991 Blood Cell Processor", Vox Sang. 29, (Feb. 10, 1975), 352-362.

Delrossi, A, et al., "Platelet-rich plasma reduces postoperative blood loss after cardiopulmonary bypass", J Thorac Cardiovasc Sura 100, (Aug. 1990), 281-285.

Depalma, L, "The preparation of fibrinogen concentrate for use as fibrin glue by four different methods", Transfusion vol. 33, No. 9, (1993), 717-720.

Deugarte, M D, et al., "Future of Fat as Raw Material for Tissue Regeneration", Lippincott Williams & Wilkins, Inc., (2007), 215-219.

Dimuzio, Paul, et al., "Development of a Tissue-Engineered Bypass Graft Seeded with Stem Cells", Vasucular, vol. 14, No. 6, (2006), 338-342.

Dinarello, C, "Interleukin-1 and Interleukin-1 Antagonism", Blood, vol. 77, No. 8, (Apr. 1991), 1627-1652.

Dinarello, C A, "Interleukin-1 in the pathogenesis and treatment of inflammatory diseases", Blood, 2011, vol. 117(14),, (2011), 3720-3732.

Edlich, Richard F, et al., "Surgical Devices in Wound Healing Management", In Wound Healing: Biochemical & Clinical Aspects 1st ed., vol. Philadelphia: W.B. Saunders Company, (1992), 581-601.

Ehricke, H H, et al., "Visualizing MR diffusion tensor fields by dynamic fiber tracking and uncertainty mapping", Computers and Graphics, Elsevvier vol. 30, No. 2, (Apr. 1, 2006), 255-264.

Eppley, et al., "Platelet Quantification and Growth Factor Analysis from Platelet-Rich Plasma: Implications for Wound Healing", Plastic and Reconstructive Surgery, 114(6), (Nov. 2004), 1502-1508.

Epstein, G H, et al., "A new autologous fibrinogen-based adhesive for otologic surgery", Ann Otol Rhinol Laryngol 95, (May 25-26, 1985), 40-45.

Evans, C H, "Novel biological approaches to the intra-articular treatment of osteoarthritis", BioDrugs, (2005), 355-62.

Feige, U, et al., "Anti-interleukin-1 and anti-tumor necrosis factor-alpha synergistically inhibit adjuvant arthritis in Lewis rats", Cmls Cellular and Molecular Li Fe Sciences, Bi Rkhauser Verlag, Heidelberg, DE, vol. 57, No. 10, (Sep. 1, 2000), 1457-1470.

Fini, et al., "Effects of pulsed electromagnetic fields on articular hyaline cartilage: review of experimental and clinical studies", Biomedicine and Pharmacotherapy, Elsevier, FR, vol. 59, No. 7, (Aug. 1, 2005), 388-394.

Fini, M., et al., "Effects of pulsed electromagnetic fields on articular hyaline cartilage: review of experimental and clinical studies", Biomed Pharmacother; vol. 59, (2005), pp. 388-394.

Fiotti, et al., "Atherosclerosis and Inflammation. Patterns of Cytokine Regulation in Patients with Peripheral Arterial Disease", Atherosclerosis. Elsevier Ireland Ltd. IE, vol. 145, No. 1, (Jul. 1, 1999), 51-60.

Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.

Fraser, John K, et al., "Plasticity of human adipose stem cells toward endothelial cells and cardiomyocytes", Nature Clinical Practice Cardiovascular Medicine, vol. 3, Supplement 1, (Mar. 2006), S33-S37.

Friesen, Robert, et al., "Blood Conservation During Pediatric Cardiac Surgery: Ultrafiltration of the Extracorporeal Circuit Volume After Cardiopulmonary Bypass", ANESTH, ANALG, (1993), 702-707.

Galois, et al., "Cartilage Tissue Engineering: State-of-the-Art and Future Approaches", Pathol Bioi (Paris), 53—Abstract only, (Dec. 2005), 2 pgs.

Gerald, Marx, "Mechanism of Fibrin Coagulation Based on Selective, Cation-Driven, Protofibral Association", Biopolymers, vol. 27, (1988), 763-774.

Gibble, et al., "Fibrin glue: the perfect operative sealant", Transfusion, 1990, vol. 30, No. 8., (1990), 741-747.

Gimble, Jeffrey M, "Adipose-Derived Stem Cells for Regenerative Medicine", Circulation Research American Heart Association, Inc., (May 11, 2007), 1249-1260.

Gomillion, Cheryl T, et al., "Stem cells and adipose tissue engineering", Biomaterials 27, Science Direct Elsevier, (2006), 6052-6063.

Grove, et al., "Plasticity of Bone Marrow-Derived Stem Cells", Stem Cells: Concise Review, (Jan. 2004), 487-500.

Guilak, Farshid, et al., "Adipose-derived adult stem cells for cartilage tissue engineering", Biorheology 41, (2004), 389-399.

Gullung, Gregory B., et al., "Platelet-rich plasma effects on degenerative disc disease: analysis of histology and imaging in an animal model", Evidence-Based Spine-Care Journal, vol. 2, Issue 4, (2011), 13-18.

(56) References Cited

OTHER PUBLICATIONS

Harris, E. L.V, et al., "Protein Purification Methods—A Practical Approach", Clarification and Extraction, (1989), 7 pgs.
Hartman, A. R, et al., "Autologous whole plasma fibrin gel. Intraoperative procurement", Arch Surg 127, (Mar. 1992), 357-359.
Hattori, et al., "Osteogenic Potential of Human Adipose Tissue-Derived Stromal Cells as an Alternative Stem Cell Source", Cells Tissues Organs, (2004), 2-12.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hennis, H L, et al., "Infectious disease risks of fibrin glue [letter]", Ophthalmic Sura 23, (Sep. 1992), 1 pg.
Hernigou, et al., "Percutaneous Autologous Bone-Marrow Grafting for Nonunions. Influence of the Number and Concentration of Progenitor Cells", Journal of Bone & Joint Surgery, (Jul. 2005), 1430-1437.
Hiromasa, Mitsuhata, et al., "An Anaphylactic Reaction to Topical Fibrin Glue", Anesthesiology, vol. 81, No. 4, (Oct. 1994), 1074-1077.
Hom, D, et al., "Promoting Healing with Recombinant Human Platelet-Derived Growth Factor-BB in a Previously Irradiated Problem Wound", The Laryngoscope, vol. 113, (Sep. 2003), 1566-1571.
Honore, Prisca, et al., "Interleukin-1aB gene-deficient mice show reduced nociceptive sensitivity in models of inflammatory and neuropathic pain but not post-operative pain", Behavioral Brain Research, (2006), 355-364.
Hood, Andrew G, et al., "Perioperative Autologous Sequestration III: A New Physiologic Glue with Wound Healing Properties", (Jan. 1993), 126-129.
Hou, W H, et al., "Microftuidic Devices for Blood Fractionation", Micromachines, (2011), 319-343.
Ishida, et al., "Platelet-Rich Plasma With Biodegradable Gelatin Hydrogel Promotes Rabbit Meniscal Tissue Regeneration", 52nd Annual Meeting of the Orthopaedic Research Society Paper No. 1035, (2006), 1 pg.
Jackson, C M, et al., "Blood coagulation", Annu Rev Biochem 49: 765-811, (1980), 22 pgs.
Jayadev, Suprya, "Trypsinization of Adherent Cells", (Aug. 8, 1991), 1 pg.
Johnstone, et al., "Autologous Mesenchymal Progenitor Cells in Articular Cartilage Repair", Clinical Orthopaedics and Related Research 367S:, (Oct. 1999), S156-S162.
Jones, D K, et al., "Confidence mapping in diffusion ensor magnetic resonance imaging tractography using a bootstrap approach", Magnetic Resonance in Medicine Wiley USA, vol. 53 , No. 5, (May 2005), 1143-1149.
Jorgensen, et al., "Stem Cells for Repair of Cartilage and Bone: The Next Challenge in Osteoarthritis and Rheumatoid Arthritis", Annals of Rheumatic Diseases, (Aug. 2000), 5 pgs.
Juge-Aubry, C, et al., "Adipose Tissue is a Major Source of Interleukin-1 Receptor Antagonist: Upregulation in Obesity and Inflammation", Diabetes, vol. 52, (May 2004), 1104-1110.
Juge-Aubry, C, et al., "Regulatory Effects of Interleukin (IL)-1, Interferon-β. and IL-4 on the Production of IL-1 Receptor Antagonist by Human Adipose Tissue", The Journal of Clinical Endocrinology & Metabolism, vol. 89, No. 6, (Jun. 2004), 2652-2658.
Karpatkin, S., "Heterogeneity of Human Platelets. VI., Correlation of Platelet Function with Platelet Volume", Blood, vol. 51, No. 2, (Feb. 1978), 307-316.
Kaufman, A, et al., "Human macrophage response to UHMWPE, TiAIV, Coer, and alumina particles: Analysis of multiple cytokines using protein arrays", Journal of Biomedical Materials Research Part A, published online in Wiley InterScience, (Jul. 2007), 464-474.
Kim, Seon Hee, et al., "Ex Vivo Gene Delivery of Il-Lra and Soluble Tnf Receptor Confers a Distal Synergistic Therapeutic Effect in Antigen-Induced Arthritis", Molecular Therapy, Nature Publishing Group, GB, vol. 6, No. 5, (Nov. 1, 2002), 591-600.
Kim, Seon Hee, et al., "Ex vivo gene delivery of Il-1 Ra and soluble TNF receptor confers a distal synergistic therapeutic effect in antigen-induced arthritis", Molecular Therapy, vol. 6, No. 5, (Nov. 1, 2002), 591-600.
Kim, Sun Jin, et al., "Development of a novel sustained release formulation of recombinant human growth homrone using sodium hyaluronate microparticles", Journal of Controlled Release, 2005, vol. 104,, (2005), 323-335.
Kimble, Robert B, et al., "Simultaneous block of interleukin-1 and tumor necrosis factor is required to completely prevent bone loss in the early postovariectomy period", Endocrinology, The Endocrine Society, US, vol. 136, No. 7—Abstract, (Jul. 1, 1995), 1 pg.
King, William, et al., "A Simple Method to Correlate the Concentration of an Anti-Inflammatory Cytokine with White Blood Cells in an Autologous Protein Solution", [Online]. Retrieved from the Internet: <URL:http://prgmobileapps.com/AppUpdates/ors/Abstracts/abs391.html>, (Feb. 24, 2014).
Kitazawa, R, et al., "Interleukin-1 Receptor Antagonist and Tumor Necrosis Factor Binding Protein Decrease Osteoclast Formation and Bone Resorption in Ovariectomized Mice", Journal of Clinical Investigation, American Society for Clinical Investigation, US, vol. 94, No. 6, (Dec. 1, 1994), 2397-2406.
Kjaergard, H. K, et al., "A simple method of preparation of autologous fibrin glue by means of ethanol", Surg Gynecol Obstet 175, (1992), 72-3.
Kjaergard, H. K, "Preparation of autologous fibrin glue from pericardial Blood", Ann Thorac Sur 55, (1993), 543-4.
Klingenberg, et al., "Treating inflammation in Atherosclerotic Cardiovascular Disease: Emerging Therapies", European Heart Journal., vol. 30, No. 23, (Dec. 2009), 2838-2844.
Kohsaka, Hitoshi, "Gene Transfer Therapy for Rheumatoid Arthritis", Japanese Journal of Clinical Medicine, No. 63, No. 9, (2005), 8 pgs.
Kuderma, H, et al., "Die klinische Anwendung der Klebung van Nervenanastomosen mit Gerinnungssubstanzen bei der Rekonstruction verletzter peripherer Nerven", Wein Klin Wochenschr 87—Not in English, (Aug. 15, 1975), 6 pgs.
Kumar, Vijay, et al., "Autologous Thrombin: Intraoperative Production From Whole Blood", Journal of American Society of Extra-Corporeal Technology. JECT, 40, (2008), 94-98.
Kumar, Vijay, et al., "Stability of Human Thrombin Produced From 11 ml of Plasma Using the Thrombin Processing Device", Journal of American Society of Extra-Corporeal Technology JECT, 37, (Mar. 2005), 390-395.
Kumar, Vijay, et al., "Whole Blood Thrombin: Development of a Process for Intra-Operative Production of Human Thrombin", Journal of American Society of Extra-Corporeal Technology JECT, 39, (Jan. 1, 2007), 18-23.
Kwon, Young-Bae, et al., "Topical application of epidermal growth factor accelerates wound healing by myofibroblast proliferation and collagen synthesis in rat", Journal of Vetrinary Science 7(2), (2006), 105-109 pgs.
Kyosti Laitakari, M D, et al., "Autologous and Homologous Fibrinogen Sealants: Adhesive Strength", Laryngoscope vol. 99, (Sep. 1989), 974-976.
Laplante, Ben L, et al., "Spine osteoarthritis", PM&R, vol. 4, (2012), S28-S36.
Lasher, Lisa, "My Experience with PRP", PowerPoint presentation, <http://www.cellfactortech.com/global_products.cfm>, (Sep. 16, 2005), 35 pgs.
Lavi, Galia, et al., "Sustained delivery of IL-1 Ra from biodegradable microspheres reduces the number of murine 816 melanoma lung metastases", Journal of Controlled Release, 123, (2007), 123-130.
Lendeckel, Stefan, et al., "Autologous stem cells (adipose) and fibrin glue used to treat widespread traumatic calvarial defects: case report", Journal of Cranio-Maxillofacial Surgery (2004) European Association for Cranio-Maxillofacial Surgery, (2004), 370-373.
Lerner, R, et al., "Current status of surgical adhesives", J Surg Res 48, (Feb. 1990), 165-80.

(56) References Cited

OTHER PUBLICATIONS

Longas, Maria O, "An Improved Method for the Purification of Human Fibrinogen", J. Biochem vol. 11, (1980), 559-564.

Lori, N F, et al., "Diffusion tensor fiber tracking of human brain connectivity: acquisition methods, reliability analysis and biological results", NMR in Biomedicine Wiley UK, vol. 15, No. 7-8, (Nov. 2002), 493-515.

Lu, X, et al., "Bone Marrow Mesenchymal Stem Cells: Progress in Bone/Cartilage Defect Repair", 19(1) Abstract, (Jan. 2002), 2 pgs.

Lucarelli, E, et al., "Platelet-derived growth factors enhance proliferation of human stromal stem cells", Biomaterials, vol. 24, (2003), 3095-3100.

Marx, Gerard, et al., "Heat Denaturation of Fibrinogen to Develop a Biomedical Matrix", Journal of Biomedical Materials Research Part B: Applied Biomaterials, (Apr. 2007), 49-57.

Masri, Marwan A, et al., "Isolation of Human Fibrinogen of High Purity and in High Yield Using Polyethylene Glycol 1000", Thromb Haemostas (Stuttgart) vol. 49 (2), (1983), 116-119.

Matras, Helene, "Fibrin Seal: The State of the Art", Journal of Oral Maxillofacial Surgery, vol. 43, (1985), 605-611.

Matthews, J, et al., "Comparison of the response of primary human peripheral blood mononuclear phagocytes from different donors to challenge with model polyethylene particles of known size and dose", Biomaterials, vol. 21, (2000), 2033-2044.

Matuska, et al., "Autologous Solution Protects Bovine Cartilage Explants from IL-1a and STFa-Induced Cartilage Degradation", Journal of Orthopaedic Research, (Jul. 16, 2013), 7 pgs.

Mehmet, C, et al., "Autologous Fibrin Glue From Intraoperatively Collected Platelet-Rich Plasma", Ann Thorac Surg, vol. 53, (1992), 530-531.

Mehta, Sanjay, et al., "Gentamicin distribution from a collagen carrier", Journal of Orthopaedic Research, vol. 14, No. 5—Abstract, (Sep. 1, 1996), 749-754.

Meijer, H, et al., "The production of antiinflammatory cytokines in whole blood by physico-chemical induction", Inftamm. Res. vol. 52, (Oct. 2003), 404-407.

Molnar, Amy, "Stem Cells from Muscles Can Repair Cartilage, Study Finds Genetically Engineered Muscle-Derived Stem Cells Improved Cartilage Repair in Rats", American College of Rheumatology, (2005), 2 pgs.

Moretz, W., et al., "A simple autologous fibrinogen glue for otologic surgery", Otolarvnaol Head Neck Surg 95, (Jul. 1986), 122-4.

Morizaki, et al., "The Effects of Platelet-Rich Plasma on Bone Marrow Stromal Cell Transplants for Tendon Healing in Vitro", J. Hand Surg. Am., vol. 35, No. 11, (Nov. 2010), 1833-1841.

Murphy, Michael P, et al., "Autologous Bone Marrow Mononuclear Cell Therapy Is Safe and Promotes Amputation-Free Survival in Patients With Critical Limb Ischemia", Journal of Vascular Surgery, C.V. Mosby Co., St. Louis, MO, US, vol. 53, No. 6, (Jan. 28, 2011), 1565-1574.

Muzio, M, et al., "Interleukin-13 Induces the Production of Interleukin-1 Receptor Antagonist (IL-1ra) and the Expression of the mRNA for the Intracellular (Keratinocyte) Form of IL-1ra in Human Myelomonocylic Cells", Blood, vol. 83, No. 7, (Apr. 1994), 1738-1743.

Nakagami, Hironori, et al., "Novel Autologous Cell Therapy in Ischemic Limb Disease Through Growth Factor Secretion by Cultured Adipose Tissue-Derived Stromal Cells", Angiogenesis by Adipose Tissue-Derived Cells, American Heart Association, Inc., (Dec. 2005), 2542-2547.

Nalamachu, Srinivas, "An Overview of Pain Management: The Clinical Efficacy and Value of Treatment", Am. J. Manag. Care. 19, (2013), 261-266.

Nathan, Suresh, et al., "Cell-Based Therapy in the Repair of Osteochondral Defects: A Novel Use for Adipose Tissue", Tissue Engineering, vol. 9, No. 4, Mary Ann Liebert, Inc., (2003), 733-744.

Nilsson, et al., "Bone Repair Induced by Bone Morphogenetic Protein in Ulnar Defects in Dogs", The Journal of Bone and Joint Surgery, vol. 68 B., No. 4, (Aug. 1986), 635-642.

Nursen, Duzgun, et al., "Cytokine inhibitors: soluble tumor necrosis factor receptor 1 and interleukin-1 receptor antagonist in Behcet's disease", Rheumatology International ; Clinical and Experimental Investigations, Springer, Berlin, DEvol. 25, No. 1,, (Jan. 2005), 1-5.

Obata, Shuji, et al., "Effect of autologous platelet-rich plasma-releasate on intervertebral disc degeneration in the rabbit anular puncture model: a preclinical study", Arthritis Research & Therapy. vol. 14 http://arthritis-research.com/content/14/6/R241, (2012), 12 pgs.

Okamoto, Y, et al., "Determination of soluble tumor necrosis factor-alpha receptor type (TNFRI) and II (TNFRII) in the urine of healthy Japanese subjects", Journal of Immunoassay and Immunochemistry, 2011, vol. 32,, (2011), 145-155.

Okunishi, K, et al., "Hepatocyte Growth Factor Significantly Suppresses Collagen-Induced Arthritis in Mice", The Journal of Immunology, vol. 179, No. 8, (Oct. 15, 2007), 15 pgs.

Orphardt, Charles E, "Denaturation of Proteins", Virtual Chembook, Elmhurst College, <http://www.elmhurst.edu/chm/vchembook/568denaturation.html> (web accessed Mar. 9, 2011), (2003), 3 pgs.

O'Shaughnessey, Krista, et al., "Autologous Protein Solution Prepared From the Blood of Osteoarthritic Patients Contains an Enhanced Profile of Anti-Inflammatory Cytokines and Anabolic Growth Factors", Journal of Orthopaedic Research, (Jun. 1, 2014), 1349-1355 pgs.

O'Shaughnessey, Krista M, et al., "Blood-derived anti-inflammatory protein solution blocks the effect of IL-1 beta on human macrophages in vitro", Imflammation Research, vol. 60, No. 10,, (Oct. 1, 2011), 929-936.

Parchment, et al., "Roles for in vitro myelotoxicity tests in preclincial drug development and clinical trial planning, Toxicology Pathology, Society of Toxicological Pathologists", vol. 21, No. 2, (1993), 241-250.

Parker, Anna M, et al., "Adipose-derived stem cells for the regeneration of damaged tissues", Expert Opinion, Cell- & Tissue-based Therapy, Expert Opin. Bioi. Ther., Informa UK Ltd, (2006), 567-578.

Planat-Benard, V., et al., "Spontaneous Cardiomyocyte Differentiation From Adipose Tissue Stroma Cells", Adipose-Derived Cell Cardiomyocyte, American Heart Association, Inc., (Feb. 6, 2004), 223-229.

Pommer, et al., "Dielectrophoretic separation of platelets from whole blood in microfluidic channels", Electrophoresis, (2008), 1213-1218.

Ponticiello, Michael S, "A Rapid Technique for the Isolation and Concentration of Stem Cells from Human Bone Marrow", Cell Factor Technologies, Inc., (2006), 1 pg.

Rader, C, et al., "Cytokine Response of Human Macrophage-like Cells After Contact With Polyethylene and Pure Titanium Particles", The Journal of Arthroplasty, vol. 14, No. 7, (Oct. 1999), 840-848.

Rader, Christoph, et al., "Phage display of combinatorial antibody libraries", Curr Opin Biotechnol., 8(4), (Aug. 1997), 503-8.

Rangappa, Sunil, et al., "Transformation of Adult Mesenchymal Stem Cells Isolated From the Fatty Tissue Into Cardiomyocytes", Adult Stem Cells Transformed into Cardiomyoctyes, Ann Thorac Surg, (2003), 775-779.

Ravi Kumar, H. S., et al., "Autologous Conditioned Serum as a Novel Alternative Option in the Treatment of Unilateral Lumbar Radiculopathy: A Prospective Study", Asian Spine Journal; 9(6), (2015), 916-922.

Re, Fabio, et al., "Expression of interleukin-1 receptor antagonist (IL-ra) by human circulating polymorphonuclear cells", European Journal of Immunology, 23, (1993), 570-573 pgs.

Rigotti, M D, et al., "Clinical Treatment of Radiotherapy Tissue Damage by Lipoaspirate Transplant: A Healing Process Mediated by Adipose-Derived Adult Stem Cells", Plastic and Reconstructive Surgery, Breast, PRS Journal vol. 119, No. 5, Stem Cell Therapy for Angiogenesis, (Apr. 15, 2007), 1409-1422.

Robert, Quigley L, et al., "Intraoperative Procurement of Autologous Fibrin Glue", Ann Thorac Surg, vol. 56, (1993), 387-389.

Rubin, M. D., et al., "Clinical Treatment of Radiotherapy Tissue Damage by Lipoaspirate Transplant: A Healing Process Mediated

(56) References Cited

OTHER PUBLICATIONS by Adipose-Derived Adult Stem Cells", Plastic and Reconstructive Surgery, Discussion vol. 119, No. 5, Stem Cell Therapy for Angiogenesis, (Apr. 15, 2007), 1423-1424.
Sadeghi, M, et al., "Strikingly higher interleukin (IL)-1a, IL-1b and soluble interleukin-1 receptor antagonist (sIL-1RA) but similar IL-2, sIl-2R, IL-3, IL-4, IL-6, sIl-6R, IL-10, tumour necrosis factor (TNF)-a, transforming growth factor (TGF)-B2, (cont.)", (Title cont. "transforming growth factor (TGF)-(32 and interferon IFN-y urine Levels in healthy females compared to healthy males: protection against urinary tract injury?") Clinical and Experimental Immunology, vol. 142, (2005), 312-317.
Sampson, Steven, et al., "Platelet rich plasma injection grafts for musculoskeletal injuries: a review", Curr Rev Musculoskelet Med, vol. 1, (Jul. 16, 2008), 165-174.
Sanal, M, et al., "Does fibrin glue cause foreign body reactions?", Eu r J Pediatr Sura 2, (1992), 285-6.
Sarzi-Puttini, Piercarlo, et al., "The Appropriate Treatment of Chronic Pain", Clin. Drug Investig. 32, (2012), 21-33.
Schaffler, Andreas, et al., "Concise Review: Adipose Tissue-Derived Stromal Cells-Basic and Clinical Implications for Novel Cell-Based Therapies", Tissue-Specific Stem Cells, Stem Cells®, (Apr. 10, 2007), 12 pgs.
Schmidt, K G, "Labelling of Human and Rabbit Platelets with Indium-Oxine Complex", (1979), 97-106.
Schmidt, K G, et al., "Preparation of Platelet Suspensions from Whole Blood in Buffer", Scand. J. Hoemato, 23, (1979), 88-96.
Semple, Elisabeth, et al., "Quality of Thrombin Produced From the Patient's Own Plasma Using the TPD™, a New Thrombin-Processing Device", Journal of American Society of Extra-Corporeal Technology, 37(2), (2005), 196-200.
Sevenoaks, Martin J., et al., "Chronic Obstructive Pulmonary Disease, inflammation and co-morbidity—a common inflammatory phenotype?", respiratory Research vol. 7:70, (2006), 1-9.
Shiozawa, Kazuko, et al., "Gene Therapy, Is a total therapy for rheumatoid arthritis possible?", Pharma Medica, vol. 17, No. 10 w/ partial English Translation, (1999), 16 pgs.
Shrivastava, Abha, et al., "Effects of Electromagnetic Forces of Earth on Human Biological System", Indian J. Prev. Soc. Med, Retrieved from the Internet: <URL:http://medind.nic.in/ibl/t09/i3/iblt09i3p162.pdf>, (Jan. 1, 2009), 162-167.
Shu-Li, Lin, et al., "Static magnetic field attenuates mortality rate of mice by increasing the production of IL-1 receptor antagonist", Int. J. Radiat. Biol. 2009, 85(7), (Jul. 31, 2009), 633-640.
Siedentop, Karl H, et al., "Autologous Fibrin Tissue Adhesive", Laryngoscope, vol. 95, (Sep. 1985), 1074-1076.
Siedentop, Karl H, et al., "Extended Experimental and Preliminary Surgical Findings with Autologous Fibrin Tissue Adhesive Made from Patient's Own Blood", Laryngoscope, vol. 96, (Oct. 1986), 1062-1064.
Sierra, D H, "Fibrin sealant adhesive systems: a review of their chemistry, material properties and clinical applications", J Biomater Appl 7, (Apr. 1993), 309-52.
Silver, Frederick H, et al., "Review Preparation and use of fibrin glue in surgery", Biomaterials 16 (1995), (1995), 891-903.
Solchaga, Luis A., et al., "Hyaluronic Acid-Based Polymers As Cell Carriers for Tissue-Engineered Repair of Bone and Cartilage", Journal of Orthopaedic Research, Orthopaedic Research Society, US, vol. 17, (Jan. 1, 1999), 205-213.
Solem, Jan Otto, et al., "Hemoconcentration by Ultrafiltration During Open-Heart Surgery", Scand J Thor Cardiovasc Surg 22, (1988), 271-274.
Sorbera, L A, "Pegsunercept. Pegylated Soluble Tumor Necrosis Factor Receptor Type 1 Peg-Stnf-RI", Drugs of the Future, Prous Science, ES, vol. 28, No. 12, (Jan. 1, 2003), 1182-1188.
Spotnitz, William D, et al., "Successful Use of Fibrin Glue During 2 Years of Surgery at a University Medical Center", The American Surgeon, vol. 55,, (Mar. 1989), 166-168.
Sutton, Robin G, et al., "Comparison of Three Blood-Processing Techniques During and After Cardiopulmonary Bypass", Ann Thorac Surg (1993) vol. 56, (1993), 6 pgs.
Swift, M, et al., "Characterization of Growth Factors in Platelet Rich Plasma", 1-Cell Factor Technologies, [Online]. Retrieved from the Internet: <http://www.cellfactortech.com/global_products.cfm>, (Sep. 16, 2005), 1 pg.
Takahashi, Kazutoshi, et al., "Induction of Pluripotent Stem Cells from Adult Human Fibroblasts by Defined Factors", Cell, Elsevier Inc., (Nov. 30, 2007), 1-12.
Tateishi-Yuyama, E, et al., "Therapuetic angiogenesis for patients with limb ischaemia by autologous transplantation of bone-barrow cells: a pilot study and randomised controlled trial", The Lancet, (2002), 427-435.
Tawes, Jr., Roy L, et al., "Autologous Fibrin Glue: The Last Step in Operative Hemostatis", The American Journal of Surgery, vol. 168, (Aug. 1994), 120-122.
Thompson, et al., "Fibrin Glue: A Review of Its Preparation, Efficacy, and Adverse Effects as a Topical Hemostat", Drug Intelligence and Clinical Pharmacy, vol. 22, (Dec. 1988), 946-952.
Tiaka, Elisavet K., et al., "Epidermal Growth Factor in the Treatment of Diabetic Foot Ulcers: An Update", Perspectives in Vascular Surgery and Endovascular Therapy 24(1), (2012), p. 37-44.
Toriumi, Dean M, et al., "Surgical Tissue Adhesives in Otolaryngology—Head and Neck Surgery", Otolaryngologic Clinics of North America, vol. 27, No. 1, (Feb. 1994), 203-209.
Ulich, Thomas R, et al., "Intratrachael Administration of Endotoxin and Cytokines: IV. The Soluble Tumor Necrosis Factor Receptor Type 1 Inhibits Acute Inflammation", American Journal of Pathology; vol. 142, No. 5, (May 1993).
Vangsness, Thomas, et al., "Stimulation of IL-1ra production from platelet-rich plasma", Poster No. 488 presented at 54th Annual Meeting of the Orthopedic Research Society, (Mar. 2-5, 2008), 1 pg.
Wang, "Cell separation by dielectrophoretic field-flow-fractionation", Analytical Chemistry, (2000), 832-839.
Weis-Fogh, U S, "Fibrinogen prepared from small blood samples for autologous use in a tissue adhesive system", Eur Surg Res 20, (1988), 381-9.
Weisman, M D, "Biochemical Characterization of Autologous Fibrinogen Adhesive", Laryngoscope 97, (Oct. 1987), 1186-1190.
Wiseman, David M, et al., "Wound Dressings: Design and Use", In Wound Healing: Biochemical & Clinical Aspects 1st ed., vol., (1992), 562-580.
Woodell-May, J, et al., "Effect of Incubation Time on Production of IL-1ra and sTNF-RI from Platelet-Rich Plasma", Paper No. 200, 55th Annual Meeting of the Orthopaedic Research Society, (Feb. 2009).
Woodell-May, J, et al., "Elution of IL-1ra from a concentrated-plasma matrix—An in vitro study", Poster Presentation at 8th World Congress of the International Cartilage Repair Society, (May 2009), 1 pg.
Woodell-May, J, et al., "Producing Accurate Platelet Counts for Platelet Rich Plasma: Validation of a Hematology Analyzer and Preparation Techniques for Counting", Scientific Foundation. Journal of Carniofacial Surgery, vol. 16, No. 5, (Sep. 2005), 749-756.
Woodell-May, Jennifer, et al., "Autologous Protein Solution Inhibits Mmp-13 Production by Il-L[Beta] and Tnf[Alpha]-Stimulated Human Articular Chondrocytes", Journal of Orthopaedic Research, vol. 29, No. 9, (Sep. 1, 2011), 1320-1326.
Wright-Carpenter, T, "Treatment of Muscle Injuries by Local Administration of Autologous Conditioned Serum: A Pilot Study on Sportsmen with Muscle Strains", Int J Sports Med, vol. 25, (Oct. 2004), 588-593.
Yang, et al., "Protective effects of IL-1Ra or vIL-10 gene transfer on a murine model of wear debris-included osteolysis", Gene Therapy 11, (2004), 483-491.
Yang, T, et al., "Recent Applications of Polyacrylamide as Biomaterials", Recent Patents on Materials Science, vol. 1, (2008), 29-40.
Yoon, Eulsik, et al., "In Vivo Osteogenic Potential of Human Adipose-Derived Stem Cells/Poly Lactide-Co-Glycolic Acid Constructs for Bone Regnration in a Rat Critical-Sized Calvarial Defect Model", Tissue Engineering, vol. 13, No. 3, (2007), 619-627.

(56) References Cited

OTHER PUBLICATIONS

Yoshida, S, et al., "Elevation of serum soluble tumour necrosis factor (TNF) receptor and IL-1 receptor antagonist levels in bronchial asthma", Clinical and Experimental Immunology, Wiley-Blackwell Publishing Ltd. vol. 106, No. 1, (Oct. 1, 1996), 73-78.
Younger, Jarred, et al., "Pain Outcomes: A Brief Review of Instruments and Techniques", Curr Pain Headache Rep. 13(1), (Feb. 2009), p. 39-43.
Zhang, et al., "IL-1ra alleviates inflammatory hyperalgesia through preventing phosphorylation of NMDA receptor NR-1 subunit in rats", Pain, vol. 135, No. 3, (Mar. 5, 2008), 232-239.
Zhang, et al., "Nanosecond pulse electric field (nanopulse): A novel non-ligand agonist for platelet activation", Archives of Biochemistry and Biophysics, Academic Press, US, vol. 471, No. 2, (Dec. 23, 2007), 240-248.
Zhang, Duan-Zhen, et al., "Transplantation of autologous adipose-derived stem cells ameliorates cardiac function in rabbits with myocardial infarction", Chinese Medical Journal, vol. 120, No. 4 General Hospital of Shenyang Military Region, (2007), 300-307.
Zuk, P. A, et al., "Multilineage cells from human adipose tissue: Implications for cellbased therapies", Tissue Engineering, 7(2), XP00219871 0, ISSN: 1076-3279, (Apr. 1, 2001), 211-228.
"U.S. Appl. No. 13/839,280, Notice of Allowability dated Oct. 31, 2018", 9 pgs.
"U.S. Appl. No. 14/803,414, Response filed Dec. 20, 2018 to Non Final Office Action dated Oct. 4, 2018", 14 pgs.
"U.S. Appl. No. 14/973,913, Non Final Office Action dated Jan. 2, 2019", 9 pgs.
"U.S. Appl. No. 14/973,913, Response filed Nov. 9, 2018 to Final Office Action dated Aug. 9, 2018", 17 pgs.
"U.S. Appl. No. 15/836,249, Non Final Office Action dated Nov. 2, 2018", 11 pgs.
"U.S. Appl. No. 15/836,249, Response filed Feb. 4, 2019 to Non Final Office action dated Nov. 2, 2018", 9 pgs.
"Canadian Application Serial No. 2,906,310, Response Filed Feb. 7, 2019 to Examiner's Rule 30(2) Requisition dated Aug. 30, 2018", 9 pgs.
"Canadian Application Serial No. 2,916,080, Response Filed Feb. 5, 2019 to Office Action dated Sep. 6, 2018", 6 pgs.
"Chinese Application Serial No. 201480027178.3, Decision of Rejection dated Dec. 4, 2018", W/English Translation, 8 pgs.
"Chinese Application Serial No. 201480027408.6, Response filed Nov. 6, 2018 Office Action dated Jul. 24, 2018", w/ English claims, 13 pgs.
"Chinese Application Serial No. 201480027655.6, Decision of Rejection dated Sep. 20, 2018", W/ English Translation, 8 pgs.
"Chinese Application Serial No. 201480027655.6, Response filed May 10, 2018 to Office Action dated Feb. 23, 2018", w/ English claims, 16 pgs.
"Chinese Application Serial No. 201480028053.2, Response filed Nov. 19, 2018 to Office Action dated Jul. 3, 2018", w/ English claims, 12 pgs.
"European Application Serial No. 10754613.7, Response filed Oct. 24, 2018 to Communication Pursuant to Article 94(3) EPC dated Jun. 26, 2018", 10 pgs.
"European Application Serial No. 14707069.2, Summons to Attend Oral Proceedings mailed Oct. 10, 2018", 9 pgs.
"European Application Serial No. 14729994.5, Communication Pursuant to Article 94(3) EPC Jan. 4, 2019", 5 pgs.
"European Application Serial No. 18160602.1, Response filed Jan. 25, 2019 to Extended European Search Report dated Apr. 30, 2018", 7 pgs.
Gabay, Cem, et al., "IL-1 pathways in inflammation and human diseases", Nat. Rev. Rheumatol. 6, 232-241, (2010), 10 pgs.
Smith, "Immunity", vol. 18, (2003), .87-96.

METHODS AND COMPOSITIONS FOR DELIVERING INTERLEUKIN-1 RECEPTOR ANTAGONIST

CROSS-REFERENCE TO RELATED APPLICATIONS

This application claims the benefit of U.S. Provisional Application No. 61/031,803 filed Feb. 27, 2008, U.S. Provisional Application No. 61/116,940 filed Nov. 21, 2008, and U.S. Provisional Application No. 61/155,048 filed Feb. 24, 2009. The entire disclosures of each of the above applications are incorporated herein by reference.

INTRODUCTION

The present technology relates to compositions comprising interleukin-1 receptor antagonist, and methods for generating, isolating, and delivering such compositions.

Interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005 In addition, methods for producing IL-1ra from body fluids, including the use of autologous fluids, are described in U.S. Pat. No. 6,623,472, Reincke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Compositions and methods using IL-1ra are known in the art. For example, IL-1ra has been delivered as part of a composition with hyaluronic acid, as described in U.S. Pat. No. 6,096,728, Collins et al., issued Aug. 1, 2000. However, many such methods and compositions are associated with issues regarding stability and half-life of IL-1ra as well as the amount and rate of IL-1ra provided. Accordingly, improved methods of delivering IL-1ra are desirable and would be useful in treating conditions and pathologies mediated by the interleukin-1 receptor, including the management of inflammation.

SUMMARY

The present technology provides methods for generating solutions rich in interleukin-1 receptor antagonist and for administering such solutions to the site of inflammation in a human or animal subject. Methods for generating such solutions include incubating a liquid volume of white blood cells and, optionally, platelets with polyacrylamide beads. The beads are then separated from the liquid volume, thereby isolating a solution rich in interleukin-1 receptor antagonist. The liquid volume of white blood cells may be whole blood and/or platelet-rich plasma.

Methods of treating a condition mediated by the interleukin-1 receptor in a human or animal subject, such as inflammation, include co-administering a solution rich in interleukin-1 receptor antagonist and fibrinogen. In various embodiments, such methods further comprise administration of thrombin and calcium chloride to the subject. The site of inflammation may be associated, for example, with arthritis, e.g., osteoarthritis. Preferably, the solution of IL-1ra is autologous.

BRIEF DESCRIPTION OF THE DRAWINGS

The present technology will become more fully understood from the detailed description and the accompanying drawings, wherein.

It should be noted that the figures set forth herein are intended to exemplify the general characteristics of materials and methods among those of the present technology, for the purpose of the description of certain embodiments.

These figures may not precisely reflect the characteristics of any given embodiment, and are not necessarily intended to define or limit specific embodiments within the scope of this technology.

DESCRIPTION

The description of the following technology is merely exemplary in nature of the subject matter, manufacture, and use of the technology disclosed herein, and is not intended to limit the scope, application, or uses of any specific invention claimed in this application, or in such other applications as may be filed claiming priority to this application, or patents issuing therefrom.

Figure 1:
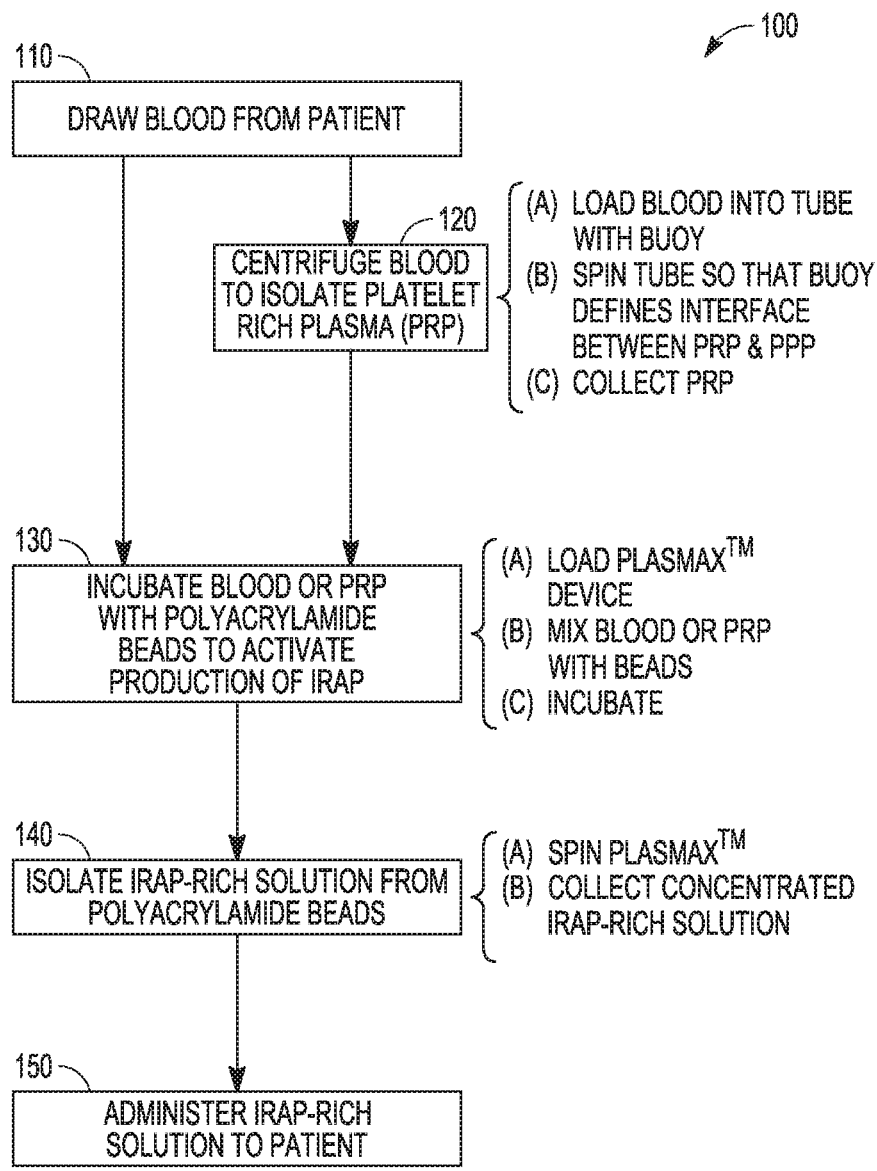
FIG. 1 is a diagrammatic illustration of a first method to produce a solution of IL-1ra according to an embodiment of the present technology.

FIG. 1 depicts a first method 100 for generating a solution rich in IL-1ra. Blood is drawn from a human subject at step 110. As discussed below, this blood may be used directly in step 130, or may be processed to create a blood fraction in step 120.

Figure 2:
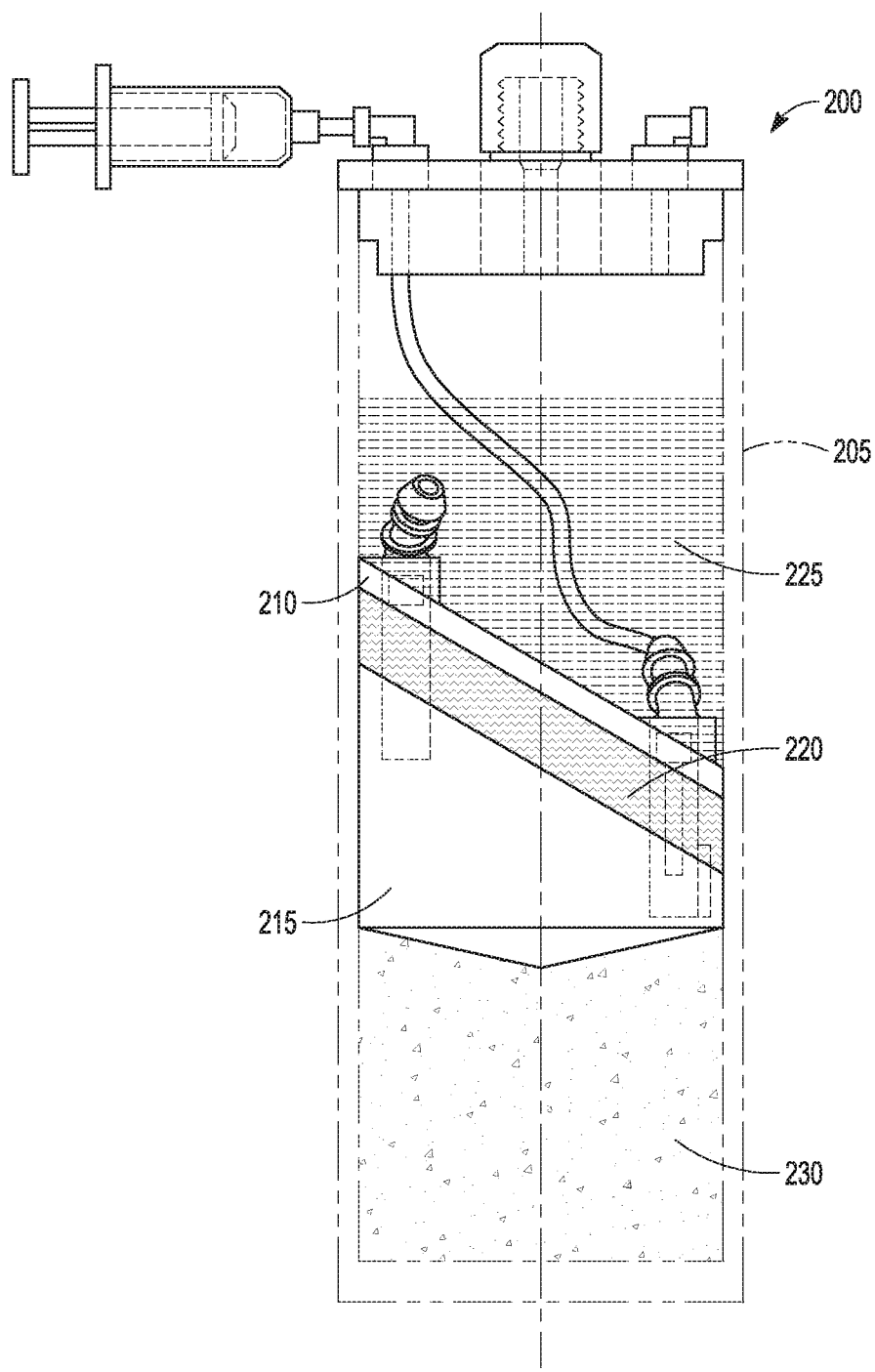
FIG. 2 is a partial cross-sectional view of a representative device used for isolating a liquid volume of white blood cells and platelets according to one embodiment of the present technology.

For example, as shown in step 120, the blood can be centrifuged to isolate platelet-rich plasma (PRP) containing white blood cells and platelets, which may be located in the buffy coat layer following sedimentation. One example of a device that may be used for isolating platelet-rich plasma at step 120 is shown in FIG. 2. In this regard, the device 200 includes a container 205, such as a tube, that is placed in a centrifuge after being filled with blood. The container 205 includes a buoy system having an isolator 210 and a buoy 215. The buoy 215 has a selected density which is tuned to reach a selected equilibrium position upon centrifugation; this position lies between a more dense blood fraction and a less dense blood fraction. During centrifugation, the buoy 215 separates the blood within the container 205 into at least two fractions, without substantially commingling the fractions, by sedimenting to a position between the two fractions. In this regard, the isolator 210 and the buoy 215 define a layer comprising platelet-rich plasma 220, while less dense platelet-poor plasma 225 generally fractionates above the isolator 210, and more dense red blood cells 230 generally fractionate below the buoy 215. Following centrifugation, a syringe or tube may then be interconnected with a portion of the buoy system to extract the platelet-rich plasma, containing white blood cells. In various embodiments, such devices may be used to generate platelet-rich plasma that includes a platelet concentration up to about 8-fold higher than whole blood and a white blood cell concentration up to about 5-fold higher than whole blood. The platelet rich plasma may comprise from about 80% to about 90% of the white blood cells present in the whole blood. Such devices that are commercially available include the GPS® II Platelet Concentrate System, from Biomet Biologics, LLC (Warsaw, Ind., USA) and GPS® III Platelet Separation System, from Biomet Biologics, LLC (Warsaw, Ind., USA).

Devices that may be used to isolate platelet-rich plasma at step 120 are also described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Application Publication No. 2004/0251217, Leach et al., published Dec. 16, 2004 (incorporated by reference herein); U.S. Application Publication No. 2005/0109716, Leach et al., published May 26, 2005 (incorporated by reference herein); U.S. Application Publication No. 2005/0196874, Dorian et al., published Sep. 8, 2005 (incorporated by reference herein); and U.S. Application Publication No. 2006/0175242, Dorian et al., published Aug. 10, 2006 (incorporated by reference herein).

Other methods may be used to isolate platelet-rich plasma in step 120. For example, whole blood can be centrifuged without using a buoy system, whole blood may be centrifuged in multiple stages, continuous-flow centrifugation can be used, and filtration can also be used. In addition, a blood component including platelet-rich plasma can be produced by separating plasma from red blood cells using a slow speed centrifugation step to prevent pelleting of the platelets. In other embodiments, the buffy coat fraction formed from centrifuged blood can be separated from remaining plasma and resuspended to form platelet-rich plasma.

In addition to the GPS® Platelet Concentrate and Separation Systems, a variety of other commercially available devices may be used to isolate platelet-rich plasma at step 120, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); DePuy (Warsaw, Ind., USA); the AutoloGel™ Process, commercially available from Cytomedix, Inc. (Rockville, Md., USA); the GenesisCS System, commercially available from EmCyte Corporation (Fort Myers, Fla., USA); and the PCCS System, commercially available from Biomet 3i, Inc. (Palm Beach Gardens, Fla., USA).

Referring again to FIG. 1, the blood drawn from the subject at step 110 may be mixed with an anticoagulant prior to subsequent use in steps 120 or 130. Suitable anticoagulants include heparin, citrate phosphate dextrose (CPD), ethylenediaminetetraacetic acid (EDTA), anticoagulant citrate dextrose solution (ACD), and mixtures thereof. The anticoagulant may be placed in the syringe used for drawing blood from the subject, or may be mixed with the blood after it is drawn.

As shown at step 130 of FIG. 1, the platelet-rich plasma containing white blood cells and platelets from step 120 is contacted with polyacrylamide beads. In some embodiments, the platelet-rich plasma is incubated with the polyacrylamide beads for a time effective to remove a portion of the liquid in the liquid volume of white blood cells and platelets. The incubation may be carried out over a period from about 30 seconds to about 72 hours and may be carried out at a temperature from about 20° C. to about 41° C. For example, the incubation may be from about one minute to about 48 hours, from about 5 minutes to about 12 hours, or from about 10 minutes to about 6 hours. In some embodiments, the incubation is conducted at about 37° C. In some embodiments the platelet rich plasma is not incubated, but is contacted with the polyacrylamide beads for only so long as necessary to perform subsequent processing. The contacting may occur at ambient conditions, e.g., at a temperature of about 20-25° C.

Polyacrylamide beads used in step 130 can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 μm up to about 180 μm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads may be used to absorb a portion of a liquid volume, including solutes smaller than the bead pore size, and can serve to concentrate the IL-1ra produced by the white blood cells. For example, combining dry polyacrylamide beads with the blood and/or platelet-rich plasma in step 130 activates production of IL-1ra by the white blood cells and also reduces the total liquid volume as the dry beads rehydrate and swell.

Alternatively, or in addition, blood from step 110 that is not subjected to centrifugation in step 120 can be combined with polyacrylamide beads in step 130 and incubated. This option is illustrated in FIG. 1 by the arrow running directly from step 110 to step 130. In this case, the polyacrylamide beads activate production of IL-1ra in the blood, but the concentration of IL-1ra may be lower compared to using platelet-rich plasma containing white blood cells or platelets or another liquid volume of white blood cells where the cells have been concentrated relative to whole blood.

White blood cells for use in step 130 may also be prepared using other methods known in the art. For example, white blood cells may be prepared from whole blood by lysing red blood cells or by centrifugation of whole blood utilizing a density gradient where the white blood cells sediment to the bottom of a centrifuge tube. An example of density centrifugation includes the Ficoll-Paque™ Plus (GE Healthcare Bio-Sciences, Piscataway, N.J., USA). In some cases, a density gradient may be used to further separate mononuclear and polymorphonuclear cells. White blood cells may also be prepared from whole blood using filtration; an example includes the Acelere™MNC Harvest System (Pall Life Sciences, Ann Arbor, Mich., USA).

Without limiting the mechanism, utility or function of the present technology, the polyacrylamide beads may serve as an activator of IL-1ra production by the white blood cells. Therefore, in the case of dry polyacrylamide beads, not only is liquid being absorbed from the volume of white blood cells, thereby concentrating the IL-1ra formed, but the beads further serve as a surface to stimulate IL-1ra production by the white blood cells. For example, IL-1ra collected using platelet-rich plasma (containing white blood cells) obtained using a device according to FIG. 2, such as the GPS® II system, may yield about a 5-fold increase in IL-1ra concentration versus whole blood. The concentration of IL-1ra may then be increased about 40-fold or more to a final concentration increase of about 200-fold upon incubation and isolation of the IL-1ra-rich solution using a device according to FIG. 3, such as a Plasmax™ device, as described further below. Thus, the increase in the amount of IL-1ra may not be due to simply increasing the concentration by reducing the volume of the sample, but may also be due to activation of the white blood cells and other growth factors from platelets by the polyacrylamide beads to increase production and/or release of IL-1ra during the incubation.

Referring again to FIG. 1, following incubation with the polyacrymide beads, an IL-1ra-rich solution is isolated from the beads, as indicated at step 140. Isolation may be accomplished by drawing off the liquid volume and leaving the beads. In some cases, the beads may be sedimented by centrifugation prior to drawing off the IL-1ra-rich solution. Isolation may also be performed by filtration, where the polyacrylamide beads are retained by a filter and the IL-1ra-rich solution passes through the filter using centrifugal force or by using vacuum, for example. If the incubation with polyacrylamide beads at step 130 utilizes dry polyacrylamide beads, the liquid volume may be reduced as the beads swell upon rehydration, thereby concentrating the resulting IL-1ra-rich solution. To maintain the increased concentration, care should be taken in the isolation step 140 so as to avoid compressing the beads or drawing liquid out from the swollen beads. For example, high centrifugal force or high vacuum may collapse the beads and/or draw liquid out of the internal volume of the beads.

Figure 3A:
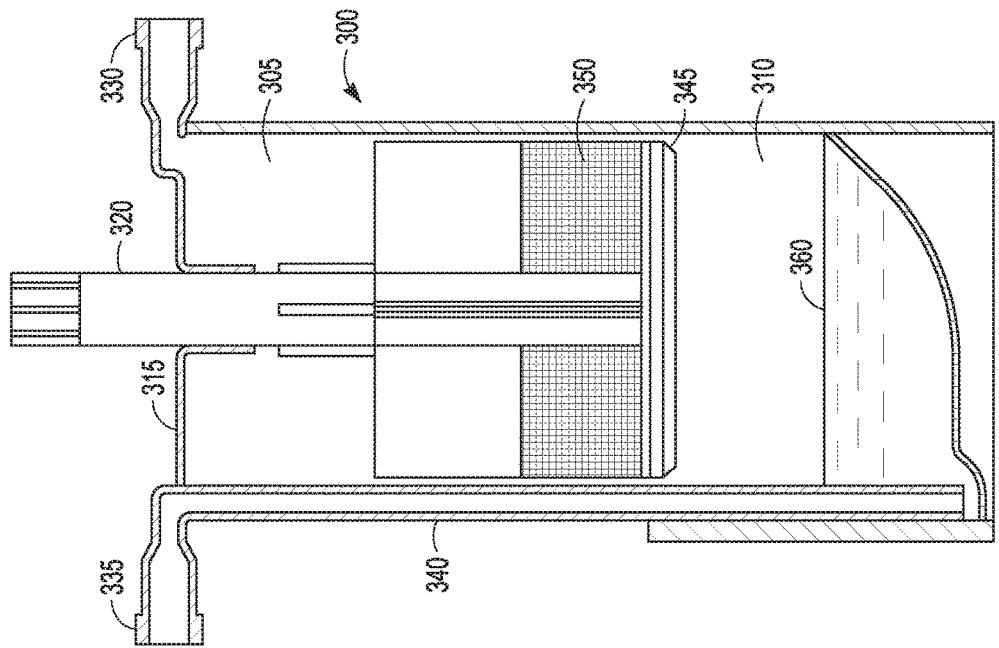
FIGS. 3A and 3B are cross-sectional views of a representative device for incubating a volume of white blood cells and platelets with polyacrylamide beads according to one embodiment of the present technology.
Figure 3B:
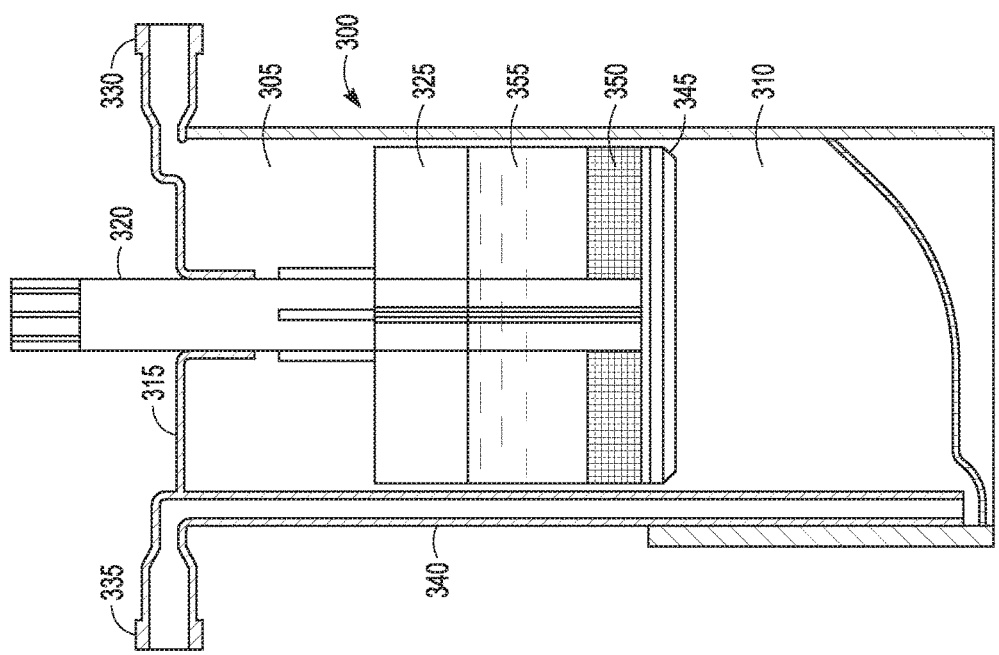

In some cases, the incubation with polyacrylamide beads, as per step 130, and the isolation of the resulting IL-1ra-rich solution, as per step 140, may be performed using a single device. An example of a device for incubating white blood cells and platelets with polyacrylamide beads is shown in FIGS. 3A and 3B. In this regard, the device 300 has an upper chamber 305 and a lower chamber 310. The upper chamber 305 has an end wall 315 through which the agitator stem 320 of a gel bead agitator 325 extends. The device 300 also has an inlet port 330 that extends through the end wall 315 and into the upper chamber 305. The device 300 also includes an outlet port 335 that communicates with a plasma concentrate conduit 340. The floor of upper chamber 305 includes a filter 345, the upper surface of which supports desiccated concentrating polyacrylamide beads 350.

During use, a fluid 355 containing white blood cells and platelets is injected to the upper chamber 305 via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then incubated for the desired time at the desired temperature. The device 300 is then centrifuged so that liquid passes to the lower chamber 310 while the polyacrylamide beads 350 are retained by a filter 345, thereby separating the polyacrylamide beads 350 from the resulting solution 360 of IL-1ra that collects in the lower chamber 310. The solution 360 may be removed from the device via outlet port 335.

Exemplary devices of FIG. 3 are disclosed in U.S. Application Publication 2006/0175268, Dorian et al., published Aug. 10, 2006; and U.S. Application Publication 2006/0243676, Swift et al., published Nov. 2, 2006; both of which are incorporated by reference herein. Such a device is commercially available as Plasmax™ Plus Plasma Concentrator, from Biomet Biologics, LLC (Warsaw, Ind., USA).

Referring again to FIG. 1, in step 150 the IL-1ra-rich solution is administered to a human or animal subject (patient). The patient receiving the IL-1ra-rich solution may be the same patient from which the blood in step 110 is derived. In this case, the method provides an autologous preparation of IL-1ra. Administration may be performed using various means, such as by injection of the IL-1ra-rich solution using a syringe, surgical application, or application concomitant with another surgical procedure. It should be understood, however, that step 150 may comprise any biomedically acceptable process or procedure by which the IL-1ra-rich solution is implanted, injected, or otherwise administered in or in proximity to a site in order to mediate effects related to stimulation of the interleukin-1 receptor, such as inflammation. For example, for treating inflammation caused by arthritis, an autologous IL-1ra-rich solution may be administered to the patient via injection. Injection may be located at or into the synovial space of an inflamed joint, or otherwise at or near the joint.

Figure 4:
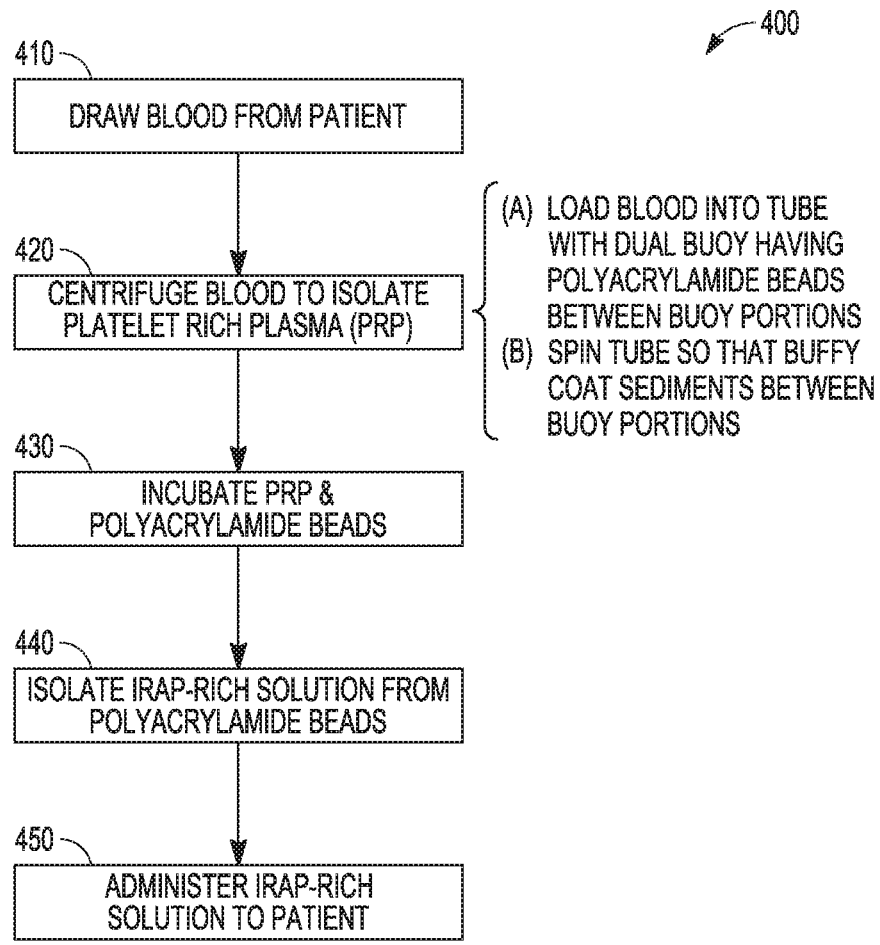
FIG. 4 is a diagrammatic illustration of a second method to produce a solution of IL-1ra according to an embodiment of the present technology.

Referring to FIG. 4, a second method 400 for generating a solution rich in IL-1ra is shown. In this case, blood is first drawn from a patient in step 410. Proceeding to step 420, the blood is centrifuged, to isolate platelet-rich plasma. As with the method of FIG. 1, the platelet-rich plasma may be isolated with a device according to FIG. 2, or any other suitable device such as described regarding the method of FIG. 1. In this method, the dual buoy mechanism includes polyacrylamide beads between the buoy 215 and isolator 210. The polyacrylamide beads may be dry or hydrated, as described in reference to step 130 for FIG. 1.

During centrifugation in step 420, platelet-rich plasma collects between the buoy 215 and isolator 210 and comes in contact with the polyacrylamide beads. The less dense platelet-poor plasma component forms above the platelet-rich plasma and the denser red blood cell component forms below. Once centrifugation is completed, the tube containing the separated blood components may be incubated for the desired time and at the desired temperature, indicated by step 430. In this manner, IL-1ra is generated by the white blood cells within the mixture of platelet-rich plasma and polyacrylamide beads located between the buoy and isolator.

In cases where dry polyacrylamide beads are used, once centrifugation is complete in step 420, the upper platelet-poor plasma component and the lower red blood cell component may be removed from the tube prior to incubation, leaving the platelet-rich plasma and polyacrylamide bead mixture between the two buoy portions. Alternatively, the mixture of platelet-rich plasma and polyacrylamide beads may be removed from the tube. In either case, separation of the platelet-rich plasma and polyacrylamide bead mixture from fluid contact with the platelet-poor plasma and the red blood cell component allows subsequent swelling and rehydrating of dry polyacrylamide beads to effectively reduce the liquid volume of the platelet-rich plasma, further concentrating the resulting IL-1ra solution.

As shown at step 440, the IL-1ra-rich solution is isolated from the polyacrylamide beads. Separation of the IL-1ra-rich solution from the beads may be accomplished using various means, such as those described in reference to step 140 in FIG. 1. As shown at step 450, the IL-1ra-rich solution is then administered to a patient. Administration may be performed using various means, such as those described in reference to step 150 in FIG. 1.

Figure 5:
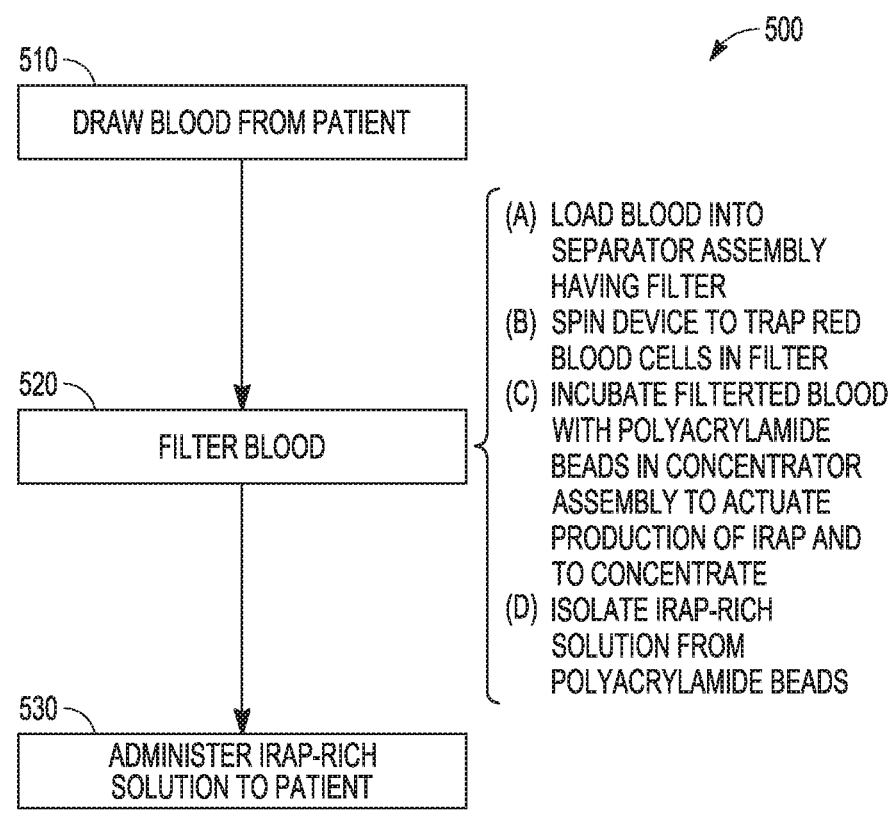
FIG. 5 is a diagrammatic illustration of a third method to produce a solution of IL-1ra according to an embodiment of the present technology.

Referring to FIG. 5, a third method 500 for generating a solution rich in IL-1ra is shown. Blood is drawn from the patient in step 510. A large volume concentration device is used to filter the blood and effectively remove some of the blood components, as shown at step 520, in order to produce platelet-rich plasma containing white blood cells and platelets.

A suitable device for use in step 520 includes a separator assembly and a concentrator assembly. The separator assembly captures red blood cells in a filter, such as a felt filter. The filter has pores and passageways that are sized to receive and entrap red blood cells during centrifugation. The device captures the red blood cells by rotating blood at speeds in a balanced cylindrical separation chamber that is lined with the filter, where the separation chamber and filter are segmented by radially extending plates into separation zones. The rotational speed of the separation chamber allows separation of platelet-rich plasma, including white blood cells, in the separation zones.

The concentrator assembly can concentrate the platelet-rich plasma by absorbing liquid in the platelet-rich plasma using dry polyacrylamide beads, as described in reference to step 130 in FIG. 1. The platelet-rich plasma is contacted in a rotating concentrating chamber with the polyacrylamide beads to produce a platelet-rich plasma concentrate while the beads are stirred. The platelet-rich plasma and polyacrylamide bead mixture can then be incubated in the concentrator assembly to allow for the generation of IL-1ra, including any additional concentration of the solution due to swelling and absorption of liquid by the beads. The resulting IL-1ra-rich solution is collected by rotating the concentration chamber at a speed to separate platelet-rich plasma concentrate from the beads. Such devices include the Vortech™ Concentration System (Biomet Biologics, LLC, Warsaw, Ind., USA), and are disclosed in U.S. Application Publication 2006/0175244, Dorian et al., published Aug. 10, 2006 and U.S. Application Publication 2006/0175242, Dorian et al., published Aug. 10, 2006, which are hereby incorporated by reference. These devices may be used in lieu of or in addition to using the tube having a buoy described in reference to step 120 in FIG. 1 to prepare platelet-rich plasma including white blood cells and platelets.

As shown at step 530, the IL-1ra-rich solution is then administered to a patient. Administration may be performed using various means, such as those described in reference to step 150 in FIG. 1.

Figure 6:
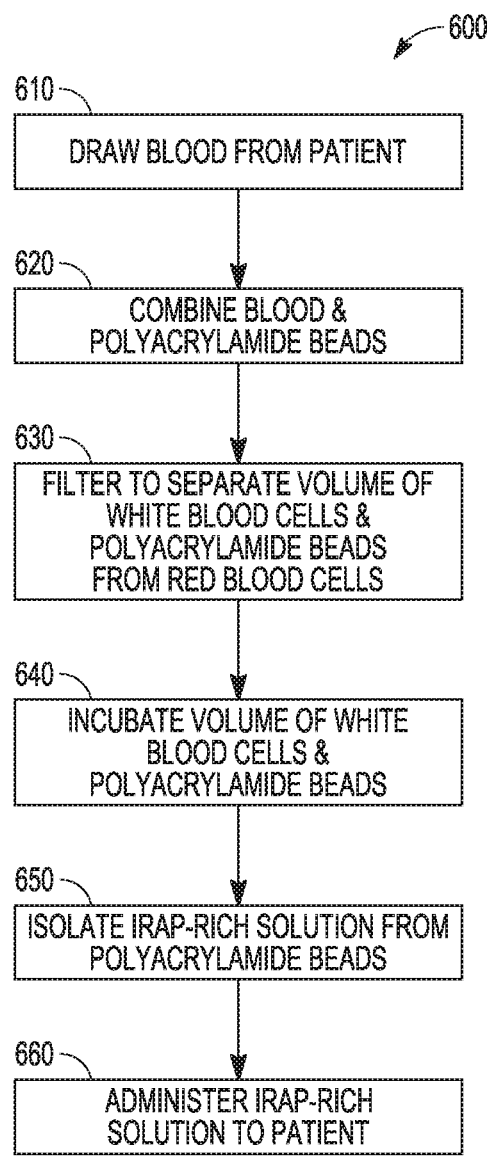
FIG. 6 is a diagrammatic illustration of a fourth method to produce a solution of IL-1ra according to an embodiment of the present technology.

Referring to FIG. 6, a fourth method 600 for generating a solution rich in IL-1ra is shown. Blood is drawn from the patient, as shown at step 610, and combined with polyacrylamide beads, as shown at step 620. The polyacrylamide beads may be dry or hydrated, as described in reference to step 130 in FIG. 1. Filtration is then used in step 630 to separate a volume of white blood cells and the polyacrylamide beads from red blood cells. Filtration may be accomplished using a single filter or a series of size exclusion filters to capture the white blood cells and the beads, while other blood components, such as red blood cells, pass with one or more filtrates. Once the filtration is complete, the volume of white blood cells and polyacrylamide beads is incubated, as shown at step 640, in order to activate the production of IL-1ra and further reduce the liquid volume if dry polyacrylamide beads are used. Platelets may also be added to the volume of white blood cells during the incubation in step 640.

The IL-1ra-rich solution is isolated from the polyacrylamide beads in step 650. Various means of isolation may be used, such as by drawing off the liquid volume and leaving the beads. In some cases, the beads are sedimented by centrifugation prior to drawing off the IL-1ra-rich solution. Isolation may also be performed by filtration, where the polyacrylamide beads are retained by a filter and the IL-1ra-rich solution passes through the filter using force generated by a centrifuge or by using vacuum, for example. In some cases, the IL-1ra-rich solution is isolated from the polyacrylamide beads by drawing the solution through the same filter or series of filters used in step 630. The IL-1ra-rich solution may be drawn into a fresh collection chamber, or into a previously used filtrate collection chamber where the one or more earlier filtrates have been removed. The IL-1ra-rich solution is then administered to the patient, as shown at step 660.

The various preparations of IL-1ra-rich solutions produced by the present technology may be sterilized by including a sterile filter to process the final isolated IL-1ra product. Similarly, an antibiotic may be included in the polyacrylamide beads during incubation or added at one or more of the various steps in the methods described herein.

The present technology provides improved methods for preparing solutions rich in IL-1ra, including autologous IL-1ra-rich concentrated plasma solutions, that reduce and/or substantially eliminate immunological issues that may arise when using non-autologous material or recombinant material. In addition, since the IL-1ra is produced by the patient's cells, natural post-translational modifications, such as glycosylation, are already present. This is not the case with most recombinant proteins since they are produced in prokaryotic hosts. Solutions, e.g., concentrated plasma solutions, rich in IL-1ra of the present technology can be characterized as comprising viable whole blood cells, and having increased concentrations of IL-1ra, serum tumor necrosis factor R1 (sTNF-r1), plasma proteins, and growth factors relative to whole blood. It is understood, however, the concentrations present in any given solution may vary depending on the initial levels of components present in the whole blood or plasma used in the present methods, and that increases in concentration are relative to those initial levels. In general, IL-1ra is present in the solutions at concentrations of at least about 10,000 pg/ml, at least about 25,000 pg/ml, or at least about 30,000 pg/ml. Plasma protein levels are typically present at concentrations of at least about 50 mg/ml, at least about 80 mg/ml, at least about 100 mg/ml, at least about 200 mg/ml, or at least about 250 mg/ml. In particular, albumin is present at a concentration of about 40 mg/ml, or at least about 100 mg/ml; and fibrinogen is present at a concentration of at least about 2 mg/ml or at least about 4 mg/ml. sTNF-r1 is typically present at concentrations greater than whole blood (about 960 pg/ml), such as at least about 1000 pg/ml, or greater than 1500 pg/ml, or greater than about 2500 pg/ml. Increased concentrations of growth factors include: platelet-derived growth factor PGDF-AB, at concentrations of greater than 50,000 pg/ml, or greater than 70,000 pg/ml; transforming growth factor TGF-β1, at concentrations greater than 150,000 pg/ml, or greater than 190,000 pg/ml; insulin-like growth factor IGF-1, at concentrations greater than about 140,000 pg/ml, or greater than 160,000 pg/ml; basic fibroblast growth factor bFGF, at concentrations greater than 150,000 pg/ml, or greater than 170,000 pg/ml; and vascular endothelial growth factor VEGF, at concentrations greater than 1,200 pg/ml, or greater than 1,400 pg/ml. Concentrations of inflammatory cytokines (e.g., interleukin 1α, interleukin 1β, tumor necrosis factor-α and interleukin 10) are generally not significantly greater than whole blood, and may be lower. Exemplary specific levels of components are set forth in Table 1, below.

TABLE 1

Exemplary Composition Components

| Component | Concentration |
| --- | --- |
| plasma proteins - total | 286 mg/ml |
| albumin | 109 mg/ml |
| fibrinogen | 4.9 mg/ml |
| IL-1ra | 34,000-108,000 pg/ml (whole blood = 200-800 pg/ml) |
| sTNF-RI | 270-3,450 pg/ml (whole blood = 960 pg/ml) |
| IL-1α | below detection limit |
| IL-1β | 22 pg/ml (whole blood = below detection limit) |
| TNF-α | below detection limit |
| IL-10 | 1.6-9.06 pg/ml (whole blood = 4.53 pg/ml) |
| Growth factors | |
| PDGF-AB | 73,201 pg/ml |
| TGF-β1 | 194,076 pg/ml |
| IGF-1 | 160,000 pg/ml |
| bFGF | 176 pg/ml |
| VEGF | 1,464 pg/ml |

The IL-1ra-rich solutions may be administered to mediate effects of IL-1 and attenuate signaling via the interleukin-1 receptor. The IL-1ra-rich solution may be used to block the biologic activity of naturally occurring IL-1, including inflammation and cartilage degradation associated with arthritis, by competitively inhibiting the binding of IL-1 to the interleukin-1 type receptor, which is expressed in many tissues and organs. For example, bone resorption and tissue damage such as cartilage degradation as a result of loss of proteoglycans due to IL-1 may be treated by administration of the IL-1ra-rich solution. In patients with arthritis, endogenous IL-1ra may not be found in effective concentrations in synovium and synovial fluid to counteract IL-1 concentrations in these patients, and hence the present IL-1ra-rich solution may be administered to treat these conditions and these sites. Dosing, administration, and frequency of treatment may be modified based on established medical practices to achieve effective treatment.

The present technology further provides methods for delivering IL-1ra. Such delivery methods provide a solution of IL-1ra and fibrinogen where the fibrinogen is activated to form a fibrin matrix that protects and retains the IL-1ra at a treatment site. The fibrin matrix can be formed in situ upon delivery of the IL-1ra.

Fibrinogen can be cross-linked into a three-dimensional matrix by activation with a clotting agent and calcium. Suitable clotting agents include thrombin (e.g., bovine, recombinant human, pooled human, or autologous), autologous clotting protein, and polyethylene glycol. Calcium may be in the form of a calcium salt, such as calcium chloride.

Figure 7:
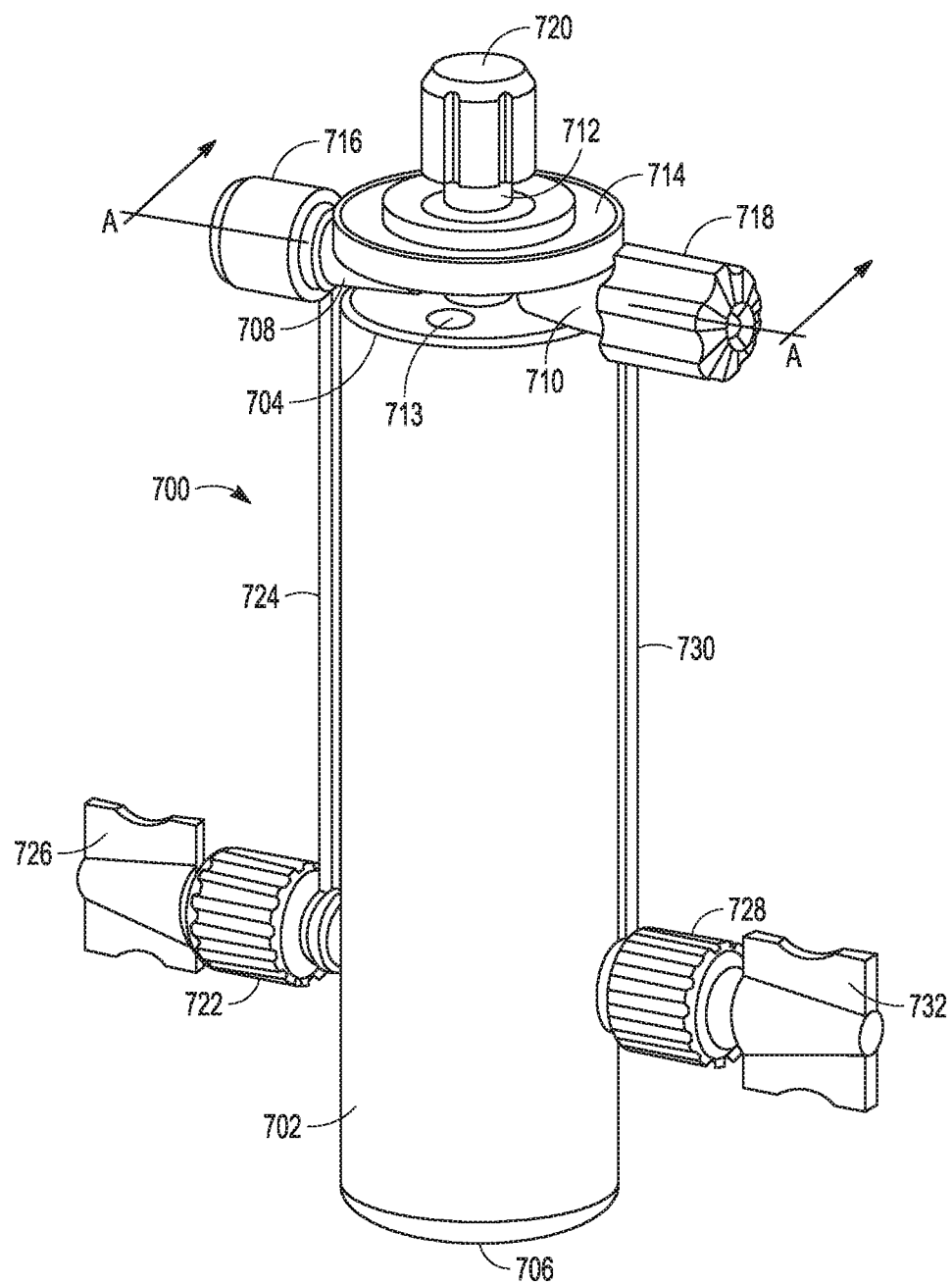
FIG. 7 is blood component isolation device which may be used in methods of the present technology.
Figure 8:
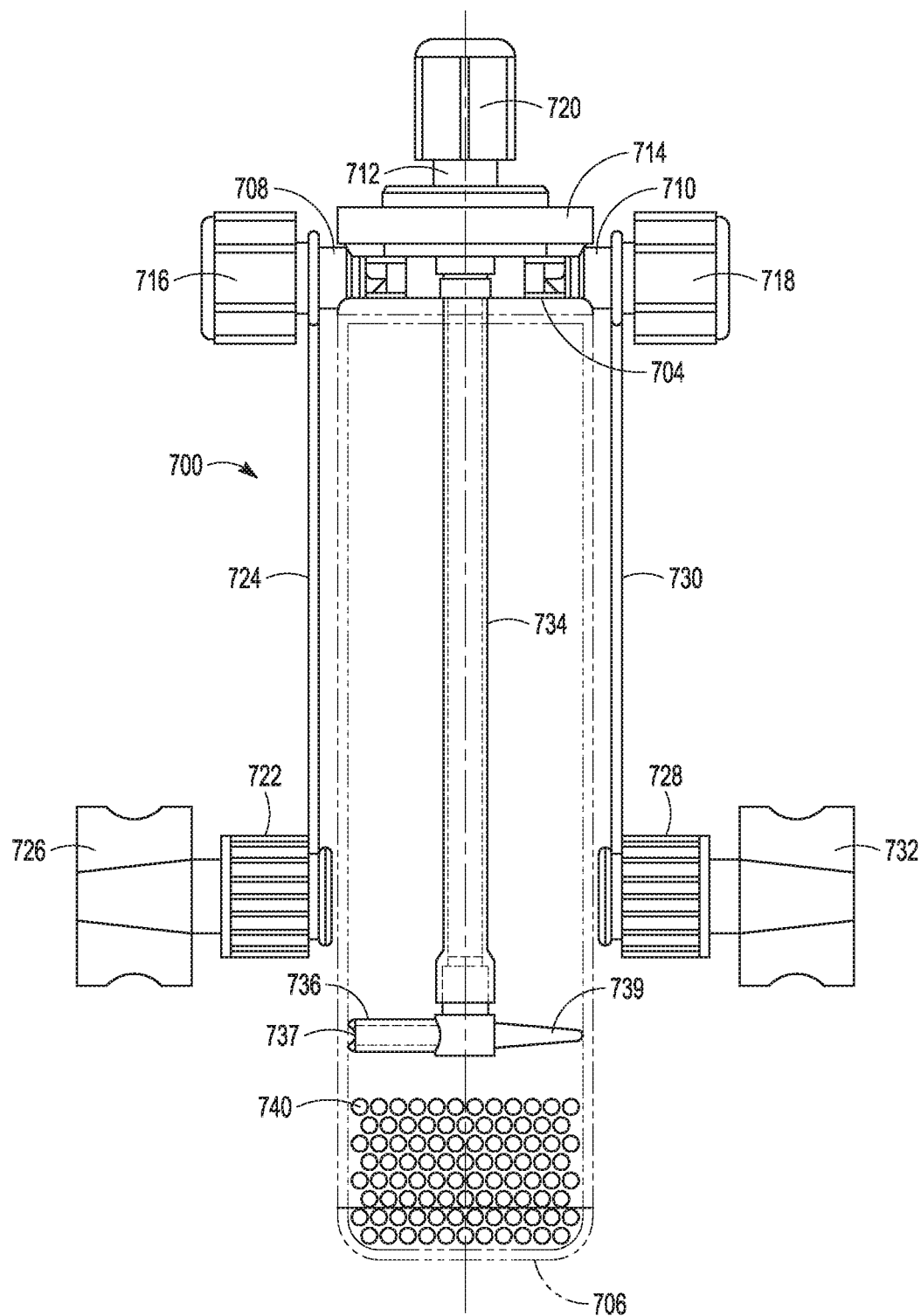
FIG. 8 is a side view of the blood component isolation device of FIG. 7, illustrating an interior portion of a main chamber of the device.

In some embodiments, the clotting agent comprises an autologous clotting protein, as a clotting fraction or composition derived from a blood obtained from the subject to be treated. A suitable clotting fraction can be obtained by a process of: loading whole blood or plasma with a calcium solution (e.g., calcium chloride in ethanol) into a blood isolation device; heating the whole blood or plasma for at least about 20 minutes, at a temperature of at least about 20° C.; and isolating the clotting fraction. The isolating may be performed by centrifuging the heated whole blood or plasma. A suitable isolation device is depicted in FIGS. 7 and 8. Such a device is commercially available as the Clotalyst™ Autologous Thrombin Collection System, sold by Biomet Biologics LLC, Warsaw, Ind., USA.

With reference to FIGS. 7 and 8, the blood separation device 700 generally includes a body having a cylindrical wall along with a first end 704 and a second end 706 that define a main chamber 702. At the first end 704 is a first port 708, a second port 710, a third port 712, a vent 713, and a filter 714. Each of the first port 708, the second port 710, the third port 712, and the vent 713 extend through the first end 704 and permit fluid communication between an exterior of the device 700 and the main chamber 702. The first port 708 can be covered with a first cap 716, the second port 710 can be covered with a second cap 718, and the third port 712 can be covered with a third cap 720. A first replacement cap 722 for the first port 708 can be attached to the first port 708 with a first tether 724. A first cover 726 can be secured to the first replacement cap 722 when the first replacement cap 722 is not in use. A second replacement cap 728 for the second port 710 can be attached to the second port 710 with a second tether 730. A second cover 732 can be secured to the second replacement cap 728 when the second replacement cap 128 is not in use.

The first port 708 and the second port 710 each include a stop valve to prevent materials, such as glass beads 740, from exiting the main chamber 702 through the first and the second ports 708 and 710. The valves can be any suitable valve, such as a duck-billed valve.

With particular reference to FIG. 8, the third port 712 includes an elongated tube portion 734 that extends within the main chamber 702. The elongated portion 734 extends from the first end 704 to a depth within the main chamber 702 to permit withdrawal of select materials, such as thrombin and other blood clotting factors, from within the main chamber 702. For example and as further described below, where the main chamber 702 includes whole blood, reagents (e.g., a calcium solution comprising calcium compound dissolved in ethanol or other suitable solvent), anticoagulant, and glass beads, incubation and centrifugation of this mixture forms a clotted mass of about including red blood cells, blood plasma, and glass beads at the second end 706 of the main chamber 702. On top of the clotted mass, at the side of the clotted mass nearest the first end 704, an effluent is formed comprising thrombin and various other clotting factors. The clotted mass at the second end 706 can be visually distinguished from the effluent. In order to extract thrombin and the other clotting factors using the elongated tube portion 734, the elongated tube portion 734 extends to a depth within the main chamber 702 that is approximately level with the portion of the effluent closest to the clotted mass.

A tip 736 is provided at a distal end of the elongated portion 734. The tip 736 extends from the elongated portion 734 at about a right angle. The tip includes a recess or notch 737. Two support posts 739 extend radially from the elongated portion 734 approximately at the tip 736 to contact an interior of the main chamber 702. The support posts 739 bias the tip 736 against the interior of the main chamber 702 to retain the tip 736 at a constant position in the main chamber 702. While the tip 736 contacts the interior of the main chamber 702, the notch 737 provides an opening or clearance between the interior wall of the main chamber 702 and the tip 736 to permit the passage of material through the notch 737 and into the tip 736. The tip 736 helps to maximize the amount of materials withdrawn through the elongated portion 734, particularly when the main chamber 702 is tilted to bring additional materials surrounding the tip 736 to the notch 737. The two support posts 739 and the tip 736 help center the elongated portion 734 in the main chamber 702.

The ports 708, 710, and 712 are sized to cooperate with a suitable fluid delivery or transport device, such as a syringe. For example, the first port 708 can be sized to cooperate with a reagent syringe to permit passage of reagent through the first port 708 and into the main chamber 702; the second port 710 can be sized to cooperate with a blood syringe to permit passage of blood through the second port 710 and into the main chamber 702; and the third port 712 can be sized to cooperate with a syringe to permit withdrawal of blood components, such as thrombin and other clotting factors, from within the main chamber 702.

The filter 714 can be any suitable filter for filtering materials as they are withdrawn from within the main chamber 702 through the third port 712. The filter 714 includes a polyester screen that is mounted atop the first port 708 and the second port 710. The polyester screen includes openings that are in the range of about 15 microns to about 25 microns in size. For example, the openings can be about 17 microns in size. In place of or in addition to, the filter 714, a filter similar to the filter 714 can be provided in the elongated portion 734 or at the tip 736.

The main chamber 702 further includes an activator, such as glass beads 740. The negatively charged surface of the glass beads activates clotting and the release of blood clotting factors, which form the clotted mass at the second end 706 of the main chamber 702. The glass beads 740 can be any suitable type of glass beads, such as boro-silicate beads.

An exemplary procedure for producing a clotting agent using the device of FIG. 7 begins injection of a reagent comprising calcium chloride and ethanol into the main chamber 702 through the first port 708. After the reagent has been injected, the first port 708 is closed using the first replacement cap 722. Blood with anticoagulant is injected into the main chamber 702 through the second port 710. After the blood has been injected, the second port 710 is closed using the second replacement cap 728. Optionally, the syringes and blood separation device 700 are pre-heated to a temperature of about 25° C.

The contents of the blood component separation device 700 are mixed by repeatedly inverting the device 700, e.g. about twelve times, so as to contact the blood with the glass beads. After mixing, the device is incubated The incubation process can be at a temperature and for a duration that will permit the contents of the device 700 to be heated at about 25° C. for about 15 minutes. Upon completion of the incubation period, a clotted mass of red blood cells, blood plasma, and glass beads forms at the second end 706 of the main chamber 702. After incubation is complete, the device 700 is shaken enough to dislodge and break-up any gel that may be present. The device 700 is then placed in a suitable centrifuge and spun at about 3200 RPM's for about 15 minutes to separate thrombin from the remaining blood components. After centrifugation, an effluent of thrombin and other clotting factors separates from the clotted mass. After centrifugation is complete, the third cap 720 is removed and a suitable extraction device, such a syringe, is used to remove the effluent of thrombin and other clotting factors from within the main chamber 702 by way of the third port 712, the elongated portion 734, and the tip 736.

Thus, the delivery method of the present technology may include administration of IL-1ra, fibrinogen, thrombin, and calcium to form a fibrin matrix at the treatment site. Exogenous fibrinogen may be added to a solution of IL-1ra, for example such as bovine thrombin, preferably at 1000 U/mL. Or, the IL-1ra solution may already have an adequate amount of endogenous fibrinogen. In the case where the solution of IL-1ra and/or fibrinogen or preparation thereof includes an anticoagulant, such as ACD-A (anticoagulant citrate dextrose solution), the addition of calcium (with thrombin) to activate the fibrinogen should exceed the effective amount of any chelator in the anticoagulant.

The IL-1ra-rich solutions prepared using the present methods can provide an increased concentration of endogenous fibrinogen relative to whole blood. For example, output of the above methods employing polyacrylamide beads and the device illustrated in FIG. 3 results in a solution rich in both IL-1ra and fibrinogen relative to whole blood. Such a device is commercially available as the Plasmax™ Plus Plasma Concentrator, from Biomet Biologics, LLC (Warsaw, Ind., USA) and includes those devices and methods of use described in U.S. Application Publication 2006/0175268, Dorian et al., published Aug. 10, 2006; and U.S. Application Publication 2006/0243676, Swift et al., published Nov. 2, 2006; both of which are incorporated by reference herein. This IL-1ra-rich and fibrinogen-rich solution may be used to treat the subject from which the original whole blood was derived; i.e., autologous treatment.

An IL-1ra-rich and fibrinogen-rich solution, prepared using the above methods using polyacrylamide beads with the Plasmax™ Plus Plasma Concentrator, provides a solution having about a 3-fold (3×) increase in fibrinogen concentration relative to whole blood. The fibrin matrix/clot formed from the 3× higher concentration of fibrinogen is more substantial than a fibrin clot made from baseline fibrinogen levels and is more resistant to breakdown and resorption.

Figure 9:
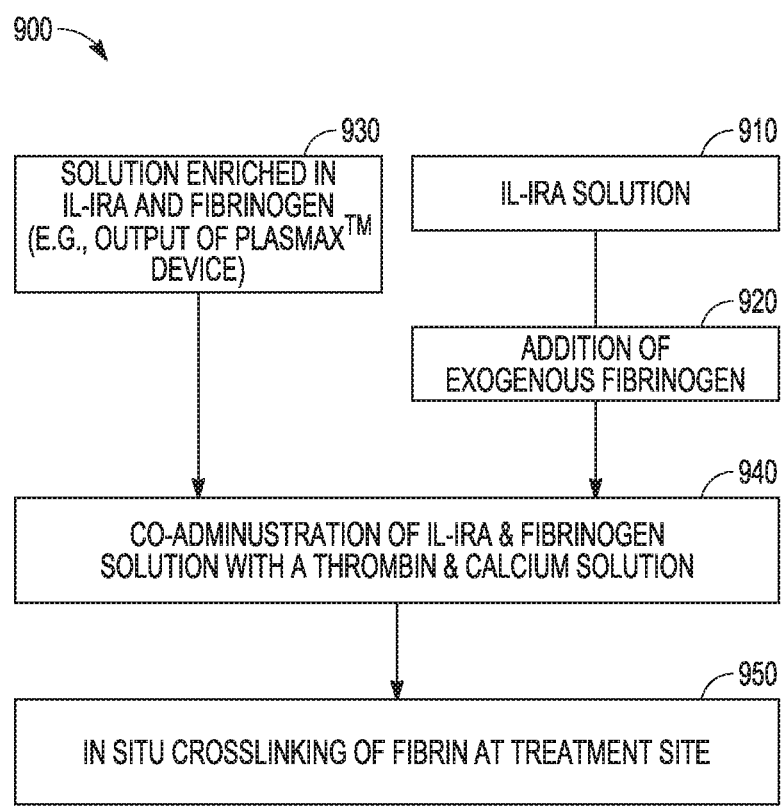
FIG. 9 is a diagrammatic illustration of a method for delivering IL-1ra according to an embodiment of the present technology.

Referring to FIG. 9, a diagrammatic illustration for delivering IL-1ra 900 is shown. At step 910, a solution of IL-1ra (IL-1ra) is provided. The IL-1ra (IL-1ra) solution may be prepared using the methods described in the present disclosure. Exogenous fibrinogen is added to the IL-1ra (IL-1ra) solution in step 920. The exogenous fibrinogen may be prepared from a different source than the IL-1ra (IL-1ra) solution, such as a different patient, or may be bovine in origin. Or, the exogenous fibrinogen may be prepared from different starting material than the IL-1ra (IL-1ra) solution, but still from the same source or patient. For example, the IL-1ra (IL-1ra) solution and the exogenous fibrinogen may be prepared from different blood samples taken from the same patient. Alternatively, as shown in step 930, a solution that is enriched in both IL-1ra (IL-1ra) and fibrinogen is prepared, for example, by using polyacrylamide beads and the Plasmax™ device, as described herein. A solution of thrombin and calcium is provided in step 940 and is co-administered with the solution of IL-1ra (IL-1ra) to a treatment site. Thereafter, as shown in step 950, the fibrin in the combined solutions cross-links in situ, forming a matrix at the treatment site that serves to protect, retain, and slow release of the IL-1ra (IL-1ra).

Delivery of IL-1ra may include co-administering a first solution of IL-1ra and fibrinogen and a second solution of thrombin and calcium to a subject. In such embodiments, the first solution and second solution are kept separate until administered so that the fibrinogen does not form a fibrin matrix until after the solutions are mixed and injected into a treatment site. The solutions may be mixed just before delivery to the treatment site or may be mixed at the treatment site.

Figure 10:
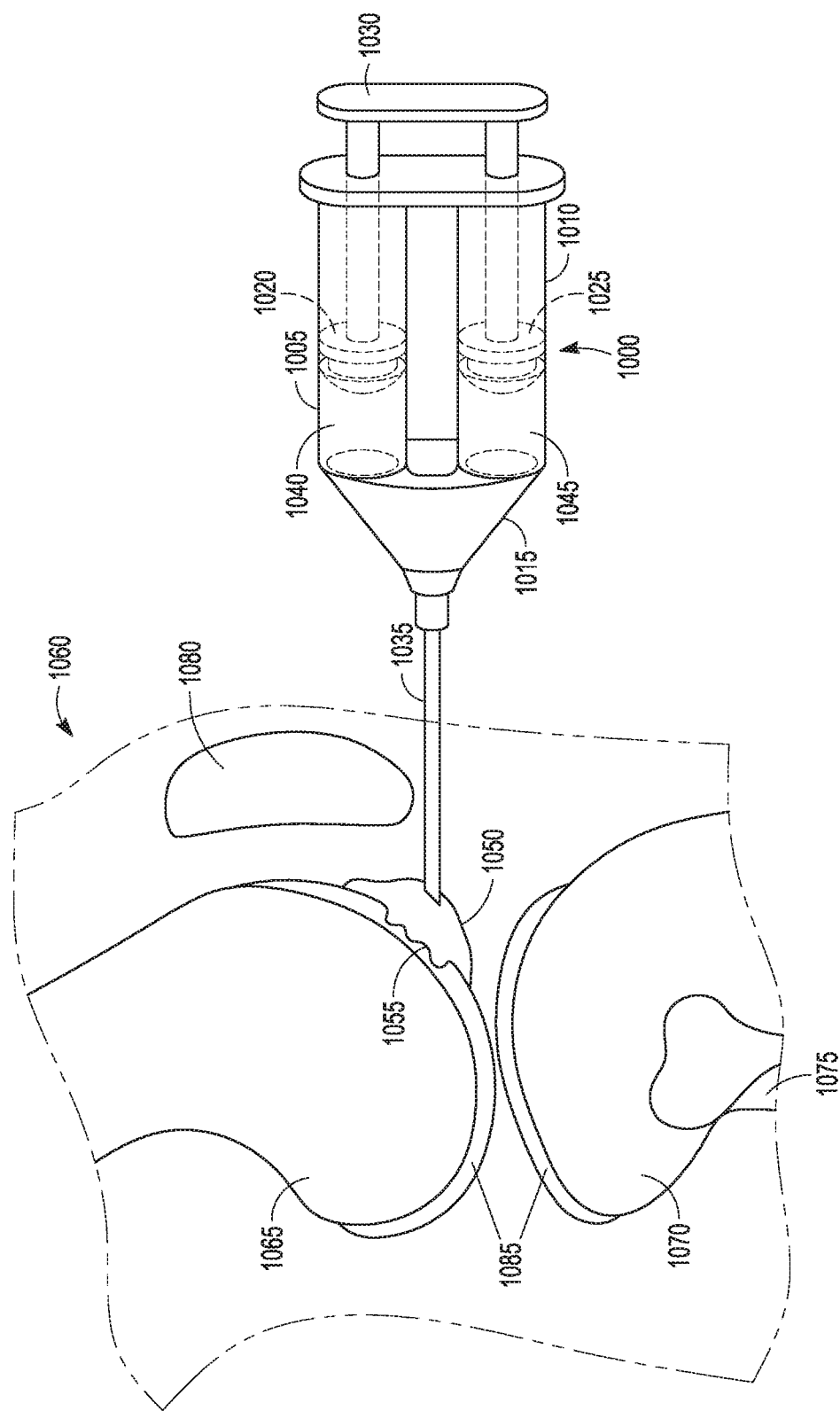
FIG. 10 is a partial cross-sectional view of a representative device for delivering IL-1ra according to one embodiment of the present technology.

Referring to FIG. 10, a dual syringe device 1000 may be employed in a medically appropriate procedure. The dual syringe device 1000 includes a first barrel 1005 and a second barrel 1010, both of which are connected to a mixing chamber 1015. A first plunger 1020 is inserted into the first barrel 1005 and a second plunger 1025 is inserted into the second barrel 1010. The first plunger 1020 and the second plunger 1025 are connected by a member 1030. The mixing chamber 1015 connects to a cannula 1035. The dual syringe device 1000 contains a first solution 1040 of IL-1ra and fibrinogen in the first barrel 1005, and a second solution 1045 of thrombin and calcium in the second barrel 1010. During co-administration, member 1030 is pushed toward the mixing chamber 1015 such that the contents of both the first barrel 1005 and the second barrel 1010 are pushed into the mixing chamber 1015. The mixed first solution 1040 and second solution 1045 travel through the cannula 1035 and form a fibrin-matrix 1050 at the treatment site 1055 within a patient's joint 1060.

In the embodiment shown in FIG. 10, the patient's joint 1060 is a knee joint that includes a femur 1065, a tibia 1070, a fibula 1075, a patella 1080, and cartilage 1085. It should be understood, however, that the treatment site 1055 may be in any joint of a human patient or animal, including shoulders, elbows, wrists, ankles, hips, and the spinal column. In addition, the present methods may be used to treat inflammation in sites within other tissues, such as muscle and tendon.

In some embodiments, the dual syringe device 1000 is used to pierce soft tissue of the patient's joint 1060 to administer the mixed first solution 1040 and second solution 1045. For example, the cannula 1035 may be a hollow needle such as a hypodermic needle. Alternatively, an incision may be made in the patient's joint 1060 to allow entry of the cannula 1035 so that the dual syringe device 800 may enter the treatment site 1055.

In some embodiments, which are not shown, the dual syringe device 1000 does not have a mixing chamber 1015 and instead includes two cannulas 1035, one leading from each barrel to the treatment site 1055. In this case, the first solution 1040 and second solution 1045 travel through the separate cannulas 1035 and mix together at the treatment site 1055 to form a fibrin-matrix 1050. In some embodiments, two separate single-barreled syringe devices are employed in place of a dual syringe device.

The fibrin matrix formed in the present delivery methods can reside at the treatment site without increasing inflammation. The IL-1ra within the fibrin matrix is protected from enzymatic degradation and may bind to the fibrin matrix so that is it slowly released from the matrix over time. The methods consequently can provide sustained delivery of IL-1ra as compared to injection of IL-1ra without the fibrin-matrix carrier.

The following specific examples are provided for illustrative purposes of how to make and use the compositions and methods of this technology and, unless explicitly stated otherwise, are not intended to be a representation that given embodiments of this technology have, or have not, been made or tested.

EXAMPLE 1

Stimulation of IL-1ra Production from Platelet-Rich Plasma

An IL-1ra-rich solution is created as follows. Whole blood (70 mL) anticoagulated (10%) with ACD-A (Braintree, Mass., USA) is drawn from 5 healthy volunteers. A portion (10 mL) is reserved for a whole blood measurement. Platelet-rich plasma (PRP) (6 mL) is produced using the GPS® II System (Biomet Biologics, LLC, Warsaw, Ind., USA). Complete blood counts (CBC) are collected for the whole blood and PRP samples following a validated procedure, as described in Woodell-May J E, Ridderman D N, Swift M J, Higgins J. "Producing Accurate Platelet Counts for Platelet Rich Plasma: Validation of a Hematology Analyzer and Preparation Techniques for Counting" J Craniofac Surg (2005) Sep. 16(5):749-56. Following the PRP production, 5 mL of the PRP is added to a modified plasma concentration device (Plasmax™, Biomet Biologics LLC, Warsaw, Ind., USA) and incubated with polyacrylamide desiccating beads in the device for 24 hours at room temperature. Following incubation, the plasma concentration device is centrifuged to separate the serum fraction.

To analyze baseline IL-1ra levels at time zero, the whole blood and PRP samples are activated with 50 µL of thrombin and 10% $CaCl_2$ (1,000 units/mL). A blood clot is formed and incubated for 30 minutes at room temperature. Following incubation, the clot is centrifuged for 5 minutes at 3,000 rpm. Serum is collected from the clots and retained for ELISA analysis. The serum fraction from the plasma concentrator does not require activation by thrombin, and is tested directly. All samples are analyzed for IL-1ra using an ELISA kit (IL-1ra Quantikine™ Kit, R&D Systems, Minneapolis, Minn., USA).

Illustrative data is presented as mean±standard deviation. Statistical significance is evaluated with a Student's t-test (a=0.05). A correlation analysis is used to compare IL-1ra output and complete blood counts (CBC) data.

Illustrative results are as follows. IL-1ra release from whole blood, PRP, and the concentrated serum are compared, with the data shown in Table 2. The whole blood and PRP IL-1ra are collected from serum following thrombin activation. The plasma concentration device is used to produce blood serum without the addition of thrombin.

TABLE 2

IL-1ra values measured by ELISA from five human donors

| Donor | Whole blood (pg/mL) | PRP (pg/mL) | Serum fraction from plasma concentrator (pg/mL) |
|---|---|---|---|
| 1 | 317 | 1,233 | 40,825 |
| 2 | 153 | 600 | 36,944 |
| 3 | 183 | 569 | 20,967 |
| 4 | 324 | 742 | 39,827 |
| 5 | 110 | 1,073 | 40,438 |
| Mean: | 217 ± 98 | 843 ± 295 | 35,800 ± 8,432 |
| Fold increase: | | 4.6X | 195X |

The PRP samples result in an 8.1-fold increase in platelets, 5.2-fold increase in total white blood cells (WBCs), an 8.7-fold increase in the monocyte fraction of the WBCs, and a 2.6-fold increase in the PMN fraction of the WBCs, as shown in Table 3. The IL-1ra production in the whole blood and PRP samples is correlated most closely to the WBC concentration ($R^2$=0.82). The 4.6-fold increase in the PRP is probably due to the increase in WBCs, and both the whole blood and PRP IL-1ra values can be considered baseline IL-1ra content. This is in contrast to the 195-fold increase in IL-1ra following the 24-hour incubation in the plasma concentrator. This plasma concentration device typically results in a 3-fold increase in plasma protein concentration due to a volume reduction caused by the desiccation process. This 3-fold decrease in volume does not account for the levels of increase seen in the amount of IL-1ra. Therefore, this level of increase indicates stimulation of WBCs to produce IL-1ra during the 24-hour incubation period.

TABLE 3

Average CBC values for blood and PRP

| Sample | Platelets (K/µL) | WBC (K/µL) | Monocytes (K/µL) | PMN (K/µL) |
|---|---|---|---|---|
| Whole blood | 200 ± 28 | 5.5 ± 1.5 | 0.4 ± 0.008 | 3.1 ± 1.3 |
| PRP | 1630 ± 210 | 28.5 ± 4.8 | 3.8 ± 1.3 | 8.0 ± 2.4 |
| Fold increase | 8.1X | 5.2X | 8.7X | 2.6X |
| $R^2$ | 0.57 | 0.82 | 0.68 | 0.77 |

Increased levels of IL-1ra are detected in PRP samples. Further processing of the PRP in a plasma concentration device can result in even greater increased levels in IL-1ra. The baseline serum values of IL-1ra (217±98 pg/mL) are similar to results found in another study (73±4.8 pg/mL), described in Meijer H, Reinecke J, Becker C, Tholen G, Wehling P. "The production of anti-inflammatory cytokines in whole blood by physico-chemical induction" *Inflamm. Res.* 2003 October; 52(10):404-7, even though significant variability between donors can exist. The IL-1ra serum levels are statistically higher in the PRP and serum output of the plasma concentrator than in the baseline serum levels. The 24-hour incubation of the PRP in the plasma concentration device results in a dose of IL-1ra (35,800±8,432 pg/mL) that is higher than the previously reported data from the 24-hour incubation in the ACS device (10,254±165 pg/mL).

Correlation analysis demonstrates that IL-1ra production is more closely correlated with the increase in WBCs than the platelet content. The IL-1ra levels do not correlate as closely with the monocytes population in the PRP. This is not surprising since the monocytes are not activated, and the serum is collected by thrombin activation of the plasma. However, it is probable that the monocytes, once activated in the plasma concentration device, participate in the significant production of IL-1ra seen.

EXAMPLE 2

Elution of IL-1ra (IL-1ra) from a Concentrated-Plasma Matrix

Anticoagulated blood (120 cc) is collected from 5 human donors. Platelet-rich plasma (PRP) is prepared using GPS®III disposables (Biomet Biologics LLC, Warsaw, Ind., USA). PRP is loaded into modified plasma concentration devices (Plasmax®, Biomet Biologics LLC, Warsaw, Ind., USA) and processed. The output is divided into 4 groups; IL-1ra in concentrated plasma with and without thrombin activation (1000 U/ml in 1M $CaCl_2$), or cell-free IL-1ra with and without thrombin activation. IL-1ra is measured using ELISA (R&D Systems) over time.

Unclotted APS produces an average of 47.1±2.1 ng over 24 hrs (p=0.34). The cell-free samples produce 33.7±1.5 ng without changing over 24 hrs (p=0.38). Once clotted, the elution of IL-1ra is slowed, with only 28% being eluted after 10 hours. Release in the cell-free samples is also delayed, but eluted 100% of available IL-1ra after 10 hours.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A method for generating a solution rich in interleukin-1 receptor antagonist, comprising contacting a liquid volume comprising white blood cells with a concentrating material, the liquid volume having a concentration of white blood cells at least equal to the concentration of white blood cells in whole blood.

2. The method of claim 1, wherein the liquid volume comprises whole blood, platelet-rich plasma, bone marrow aspirate, a bone marrow concentrate, a white blood cell fraction, a buffy coat fraction, a white blood cell isolate, or a combination thereof.

3. The method of claim 1, wherein the contacting includes incubating the liquid volume with the concentrating material for a period of time from about 30 seconds to about 24 hours.

4. The method of claim 1, wherein the concentrating material comprises a porous material, an absorptive material, a desiccating material, a filter, or a combination thereof.

5. The method of claim 1, wherein the concentrating material comprises polyacrylamide beads.

6. The method of claim 1, wherein the contacting generates a solution having an interleukin-1 receptor antagonist concentration of at least about 10,000 pg/ml.

7. The method of claim 1, wherein the solution comprises soluble tumor necrosis factor receptor 1 (sTNF-R1) at a concentration greater than the concentration of the sTNF-R1 present in whole blood or plasma.

8. A method of making a solution rich in interleukin-1 receptor antagonist, comprising contacting a liquid volume of white blood cells with a solid activator configured to activate white blood cells to generate interleukin-1 receptor antagonist, the liquid volume having a concentration of white blood cells greater than or equal to a concentration of white blood cells in whole blood.

9. The method of claim 6, wherein the solution has a concentration of interleukin-1 receptor antagonist of at least about 30,000 pg/ml.

10. The method of claim 6, wherein the solid activator comprises a porous material, a desiccating material, an absorptive material, a filter, or a combination thereof.

11. The method of claim 6, wherein the solid activator comprises polyacrylamide beads.

12. The method of claim 6, wherein the liquid volume comprises a platelet-rich plasma, a bone marrow aspirate, a bone marrow concentrate, a white blood cell fraction, a buffy coat fraction, a white blood cell isolate, or a combination thereof.

13. The method of claim 6, wherein the contacting comprises incubating the liquid volume with the solid activator for a period of time from about 30 seconds to about 24 hours.

* * * * *

UNITED STATES PATENT AND TRADEMARK OFFICE
CERTIFICATE OF CORRECTION

PATENT NO. : 10,400,017 B2
APPLICATION NO. : 15/616548
DATED : September 3, 2019
INVENTOR(S) : Higgins et al.

Page 1 of 3

It is certified that error appears in the above-identified patent and that said Letters Patent is hereby corrected as shown below:

On page 8, in Column 2, under "Other Publications", Line 22, delete "o" and insert --of-- therefor On page 9, in Column 1, under "Other Publications", Line 24, delete "NF-kB" and insert --NF-κB-- therefor On page 9, in Column 1, under "Other Publications", Line 27, delete "TNF-a," and insert --TNF-α,-- therefor On page 9, in Column 1, under "Other Publications", Line 31, delete "a/β" and insert --α/β-- therefor On page 9, in Column 1, under "Other Publications", Line 36, delete "(PET STNF-RI)" and insert --(PET sTNF-RI)-- therefor On page 15, in Column 2, under "Other Publications", Line 7, delete "TGFb1" and insert --TGFβ1-- therefor On page 15, in Column 2, under "Other Publications", Line 16, delete "Factor-?1" and insert --Factor-β1-- therefor On page 15, in Column 2, under "Other Publications", Line 67, delete "toher acive" and insert --other active-- therefor On page 16, in Column 1, under "Other Publications", Line 42, delete "(IL-IRa)" and insert --(IL-1Ra)-- therefor On page 16, in Column 2, under "Other Publications", Line 55, delete "Protofibral" and insert --Protofibril-- therefor On page 17, in Column 1, under "Other Publications", Line 25, delete ""Interleukin-1ab" and insert --"Interleukin-1αβ-- therefor Signed and Sealed this
Sixteenth Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,400,017 B2

On page 17, in Column 1, under "Other Publications", Line 32, delete ""Microftuidic" and insert --"Microfluidic-- therefor On page 17, in Column 1, under "Other Publications", Line 45, delete "ensor" and insert --tensor-- therefor On page 17, in Column 1, under "Other Publications", Line 63, delete "TiAIV, Coer," and insert --TiAIV, CoCr,-- therefor On page 17, in Column 1, under "Other Publications", Line 67, delete "II-Lra" and insert --IL-1Ra-- therefor On page 17, in Column 2, under "Other Publications", Line 8, delete "homrone" and insert --hormone-- therefor On page 18, in Column 1, under "Other Publications", Line 25, delete "IL-1a and STFa-Induced" and insert --IL-1α and TNFα-Induced-- therefor On page 18, in Column 1, under "Other Publications", Line 53, delete "Myleomonocylic" and insert --Myleomonocytic-- therefor On page 18, in Column 2, under "Other Publications", Line 29, delete "preclincial" and insert --preclinical-- therefor On page 18, in Column 2, under "Other Publications", Line 62, delete "(IL-ra)" and insert --(IL-1Ra)-- therefor On page 19, in Column 1, under "Other Publications", Line 4, delete "(IL)-1a, IL-1b" and insert --(IL)-1α, IL-1β-- therefor On page 19, in Column 1, under "Other Publications", Line 7, delete "(TNF)-a," and insert --(TNF)-α,-- therefor On page 19, in Column 1, under "Other Publications", Line 7, delete "(TGF)-B2," and insert --(TGF)-β2,-- therefor On page 19, in Column 1, under "Other Publications", Line 8, delete "(TGF)-(32" and insert --(TGF)-β2-- therefor On page 19, in Column 1, under "Other Publications", Line 8, delete "IFN-y" and insert --IFN-γ-- therefor On page 19, in Column 2, under "Other Publications", Line 11, delete ""Therapuetic" and insert --"Therapeutic-- therefor On page 19, in Column 2, under "Other Publications", Line 27, delete ""Intratrachael" and insert --"Intratracheal-- therefor On page 19, in Column 2, under "Other Publications", Line 57, delete "II-L[Beta] and Tnf[Alpha]-Stimulated" and insert --IL-1β and Tnfα-Stimulated-- therefor On page 19, in Column 2, under "Other Publications", Line 71, delete "Regneration" and insert --Regeneration-- therefor In Column 18, Line 10, in Claim 9, delete "6," and insert --8,-- therefor In Column 18, Line 13, in Claim 10, delete "6," and insert --8,-- therefor In Column 18, Line 16, in Claim 11, delete "6," and insert --8,-- therefor In Column 18, Line 18, in Claim 12, delete "6," and insert --8,-- therefor In Column 18, Line 13, in Claim 23, delete "6," and insert --8,-- therefor